(12) United States Patent
Almen et al.

(10) Patent No.: US 6,448,442 B1
(45) Date of Patent: Sep. 10, 2002

(54) CONTRAST MEDIA

(75) Inventors: Torsten Almen, Falsterbo; Fredrik Ek, Lund, both of (SE)

(73) Assignee: Amersham Health AS, Oslo (NO)

(*) Notice: Subject to any disclaimer, the term of this patent is extended or adjusted under 35 U.S.C. 154(b) by 0 days.

(21) Appl. No.: 09/560,142

(22) Filed: Apr. 28, 2000

Related U.S. Application Data

(60) Provisional application No. 60/135,947, filed on May 25, 1999.

(30) Foreign Application Priority Data

Apr. 30, 1999 (GB) .............................. 9910146
Dec. 20, 1999 (GB) .............................. 9930074

(51) Int. Cl.$^7$ ...................... C07C 233/03; A61K 49/00
(52) U.S. Cl. ................ 564/153; 424/9.452; 514/546; 514/751; 514/754; 560/130; 560/141; 560/142
(58) Field of Search ..................... 424/9.452; 564/153; 514/546, 751, 754; 560/130, 141, 142

(56) References Cited

U.S. PATENT DOCUMENTS

| | | | | |
|---|---|---|---|---|
| 5,047,228 A | * | 9/1991 | Gries et al. ..................... 424/5 |
| 5,308,607 A | * | 5/1994 | Josef et al. ..................... 424/5 |
| 5,616,798 A | * | 4/1997 | Dugast-Zrihen et al. .... 564/153 |
| 5,882,628 A | * | 3/1999 | Almen et al. ............ 424/9.452 |
| 5,993,780 A | * | 11/1999 | Almen et al. ............ 424/9.452 |

* cited by examiner

*Primary Examiner*—Shailendra Kumar
(74) *Attorney, Agent, or Firm*—Bacon & Thomas

(57) ABSTRACT

The invention provides low viscosity iodinated aryl compounds, useful as X-ray contrast agents of formula I

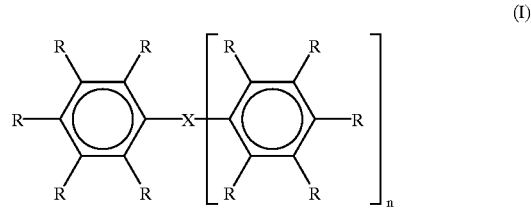

wherein n is 0 or 1, and where n is 1 each $C_6R_5$ moiety may be the same or different; X denotes a bond or a group providing a 1 to 7 atom chain linking two $C_6R_5$ moieties or, where n is 0, X denotes a group R; each group R is a hydrogen atom, an iodine atom or a hydrophilic moiety M or $M_1$, two or three non-adjacent R groups in each $C_6R_5$ moiety being iodine and at least one R group in each $C_6R_5$ moiety being an M or $M_1$ moiety; each M which may be the same or different, is a non-ionic hydrophilic moiety; and each $M_1$ independently represents a —$CHOHCON(R_1)_2$ group wherein each $R_1$, which may be the same or different, is a hydrogen atom, an OH group or a $C_{1-6}$ alkoxy or optionally hydroxylated $C_{1-5}$ alkyl group; at least one R group in the molecule being an $M_1$ moiety; and isomers thereof.

25 Claims, No Drawings

CONTRAST MEDIA

RELATED APPLICATIONS

This application claims benefit under 35 U.S.C. 119(e) of provisional application Ser. No. 60/135,947, filed May 25, 1999.

FIELD OF THE INVENTION

This invention relates to improvements in and relating to contrast media, and in particular iodinated X-ray contrast media.

BACKGROUND OF THE INVENTION

Contrast media may be administered in medical imaging procedures, for example X-ray, magnetic resonance and ultrasound imaging, to enhance the image contrast in images of a subject, generally a human or non-human animal body. The resulting enhanced contrast enables different organs, tissue types or body compartments to be more clearly observed or identified. In X-ray imaging, the contrast media function by modifying the X-ray absorption characteristics of the body sites into which they distribute.

Clearly however the utility of a material as a contrast medium is governed largely by its toxicity, by its diagnostic efficacy, by other adverse effects it may have on the subject to which it is administered, and by its ease of storage and ease of administration.

Since such media are conventionally used for diagnostic purposes rather than to achieve a direct therapeutic effect, when developing new contrast media there is a general desire to develop media having as little as possible an effect on the various biological mechanisms of the cells or the body as this will generally lead to lower animal toxicity and lower adverse clinical effects.

The toxicity and adverse biological effects of a contrast medium are contributed to by the components of the medium, e.g. the solvent or carrier as well as the contrast agent and its components (e.g. ions where it is ionic) and metabolites.

The following major contributing factors to contrast media toxicity and adverse effects have been identified:
the chemotoxicity of the contrast agent,
the osmolality of the contrast medium, and
the ionic composition (or lack thereof) of the contrast medium.

In coronary angiography, for example, injection into the circulatory system of contrast media has been associated with several serious effects on cardiac function. These effects are sufficiently severe as to place limitations on the use in angiography of certain contrast media.

In this procedure, for a short period of time a bolus of contrast medium rather than blood flows through the circulatory system and differences in the chemical and physico-chemical nature of the contrast medium and the blood that it temporarily replaces can give rise to undesirable effects, e.g. arrhythmias, QT-prolongation, and, especially, reduction in cardiac contractile force and occurrence of ventricular fibrillation. There have been many investigations into these negative effects on cardiac function of infusion of contrast media into the circulatory system, e.g. during angiography, and means for reducing or eliminating these effects have been widely sought.

Early injectable ionic x-ray contrast agents, based on triiodophenylcarboxylate salts, were particularly associated with osmotoxic effects deriving from the hypertonicity of the contrast media injected.

This hypertonicity causes osmotic effects such as the draining out of water from red-blood cells, endothelial cells, and heart and blood vessel muscle cells. Loss of water makes red blood cells stiff and hypertonicity, chemotoxicity and non-optimal ionic make-up separately or together reduce the contractile force of the muscle cells and cause dilation of small blood vessels and a resultant decrease in blood pressure.

The osmotoxicity problem was addressed by the development of the non-ionic triiodophenyl monomers, such as iohexol, which allowed the same contrast effective iodine concentrations to be attained with greatly reduced attendant osmotoxicity effects.

The drive towards reduced osmotoxicity led in due course to the development of the non-ionic bis(triiodophenyl) dimers, such as iodixanol, which reduce osmotoxicity associated problems still further allowing contrast effective iodine concentrations to be achieved with hypotonic solutions.

This ability to achieve contrast effective iodine concentrations without taking solution osmolality up to isotonic levels (about 300 mOsm/kg $H_2O$) further enabled the contribution to toxicity of ionic imbalance to be addressed by the inclusion of various plasma cations, as discussed for example in WO-90/01194 and WO-91/13636 of Nycomed Imaging AS.

However X-ray contrast media, at commercial high iodine concentrations of about 300 mgI/mL have relatively high viscosities, ranging from about 15 to about 60 mPas at ambient temperature with the dimeric media generally being more viscous than the monomeric media. Such viscosities pose problems to the administrator of the contrast medium, requiring relatively large bore needles or high applied pressure, and are particularly pronounced in paediatric radiography and in radiographic techniques which require rapid, bolus administration, e.g. in angiography.

In practice, viscosities in excess of 30 mPas at body temperature (37° C.) are unacceptably high for routine X-ray investigations, and especially for paediatric investigations Accordingly, the maximum practical iodine concentration achievable with available non-ionic iodinated X-ray contrast agents is generally about 300–350 mgI/mL. Higher iodine concentrations, if accessible at acceptable viscosities, would increase the diagnostic efficacy of contrast enhanced images. Alternatively viewed, lower contrast medium viscosities for any given iodine concentration would increase ease of administration and the range of investigations and patients for which the contrast media could be used.

SUMMARY OF THE INVENTION

The present invention addresses the viscosity problem encountered with the prior art materials and thus viewed from one aspect the invention provides iodinated aryl compounds, useful as X-ray contrast agents, of formula I

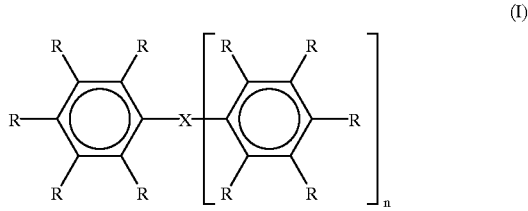

(wherein n is 0 or 1, and where n is 1 each $C_6R_5$ moiety may be the same or different; each group R is a hydrogen atom, an iodine atom or a hydrophilic moiety M or $M_1$, two or three non-adjacent R groups in each $C_6R_5$ moiety being iodine and at least one, and preferably two or three, R groups in each $C_6R_5$ moiety being M or $M_1$ moieties; X denotes a bond or a group providing a 1 to 7, for example 1, 2, 3 or 4 atom chain linking two $C_6R_5$ moieties or, where n is 0, X denotes a group R; each M independently is a non-ionic hydrophilic moiety; and each $M_1$ independently represents a $C_{1-4}$alkyl group substituted by at least one hydroxyl group and optionally linked to the phenyl ring via a carbonyl, sulphone or sulphoxide group, at least one R group, preferably at least two R groups and especially preferably at least one R group in each $C_6R_5$ moiety, being an $M_1$ moiety; with the proviso that where n is zero either at least one $M_1$ group other than a hydroxymethyl or 1,2-dihydroxyethyl (and optionally other than any hydroxyethyl) group is present or then if one hydroxymethyl or 1,2-dihydroxyethyl $M_1$ group (and optionally any hydroxyethyl group) is present at least one nitrogen-attached hydroxylated alkyl (preferably $C_{1-4}$-alkyl) moiety-containing M group is also present) and isomers, especially stereoisomers and rotamers, thereof.

It has also been found, surprisingly, that mandelic amides combine low viscosity and high hydrophilicity and a further aspect of the present invention provides iodinated aryl compounds, useful as X-ray contrast agents of formula I

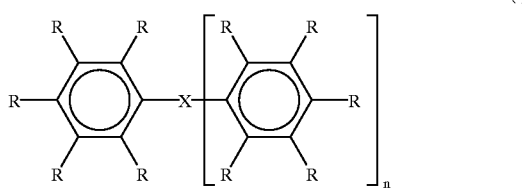

(I)

wherein n is 0 or 1, preferably 0, and where n is 1 each $C_6R_5$ moiety may be the same or different; X denotes a bond or a group providing a 1 to 7, for example 1, 2, 3 or 4 atom chain linking two $C_6R_5$ moieties or, where n is 0, X denotes a group R; each group R is a hydrogen atom, an iodine atom or a hydrophilic moiety M or $M_1$, two or three non-adjacent R groups in each $C_6R_5$ moiety being iodine and at least one, and preferably two, more preferably three, R groups in each $C_6R_5$ moiety being M or $M_1$ moieties; each M which may be the same or different, preferably being different, is a non-ionic hydrophilic moiety; and each $M_1$ independently represents a —CHOHCON($R_1$)$_2$ group wherein each $R_1$, which may be the same or different, is a hydrogen atom, an OR group or a $C_{1-6}$ alkoxy or optionally hydroxylated $C_{1-5}$ alkyl group, preferably a hydrogen atom, at least one R group in the whole molecule and where n=1, preferably at least one R group in each $C_6R_5$ moiety, being an $M_1$ moiety; and isomers thereof.

In a further aspect the invention provides a compound of formula $C_6R_6$ wherein three non-adjacent R groups are iodine and the remaining R groups are non-ionic, hydrophilic moieties, said compound being water soluble at 20° C. to a concentration of at least 350 mgI/ml and which in aqueous solution at 20° C. at a concentration of 350 mg I/ml has a viscosity no greater than 13.8 mPas.

In a yet further aspect, the invention provides a compound of formula $C_6R_6$ wherein three non-adjacent R groups are iodine and the remaining R groups are non-ionic, hydrophilic moieties, said compound being water soluble at 20° C. to a concentration of at least 400 mgI/ml and which in aqueous solution at 20° C. at a concentration of 400 mg I/ml has a viscosity no greater than 30.0 mPas.

DETAILED DESCRIPTION OF THE INVENTION

It is found that the compounds of the invention exhibit advantageously low viscosity in aqueous solution; this is thought to derive from the presence of $M_1$ groups on the phenyl groups, from compound asymmetry and, in the dimer compounds, from the nature of the linker X (especially where X provides a linkage less than 5 atoms in length).

The α-hydroxyamide side chains are thought to contribute particularly to the low viscosity of compounds of the invention. These compounds of the invention have advantageously low viscosities as compared to current commercially available products for use as X-ray contrast agents. Low viscosity is a generally highly desirable property for X-ray contrast media, particularly so when the compounds are to be administered to children. These compounds of the invention will preferably have a viscosity of less than 20 more preferably less than 18, especially no more than 15 mPas in aqueous solution at 20° C. and a concentration of 350 mgI/ml.

These compounds of the invention also exhibit an advantageously high hydrophilicity, and it is this combination of low viscosity and high hydrophilicity that makes the compounds of the invention so desirable for use in contrast media.

Thus for example all of the water-soluble monomer compounds according to the invention that have been tested have exhibited viscosities lower than that of iohexal.

The compounds of formula I are preferably asymmetric. For the monomer compounds (where n=0) this may be achieved by asymmetric substitution of the phenyl ring. For the dimers this can be achieved by the use of an asymmetric 2 or more atom chain-forming group X and/or by selection of non-identical $C_6R_5$ groups, i.e. by non-identical substitution of the iodophenyl end groups. Asymmetric molecules are preferred as they have been found to have better water-solubility.

Such non-identical substitution of the phenyl end groups, the $C_6R_5$ moieties, may be achieved by having different numbers or positions of iodine substitution and/or by different numbers, positions or identities of M or $M_1$ substitution. To maximize iodine loading, triodophenyl end groups, i.e. groups of formula

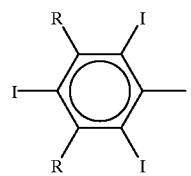

are preferred, and in these the two R groups may be the same or different, although preferably both represent M or $M_1$ groups.

Where a phenyl end group is disubstituted by iodine, it is preferably of formula

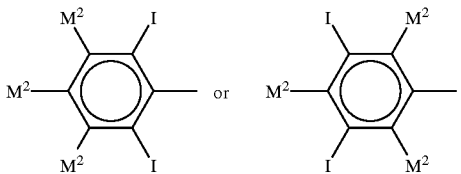

(where each $M^2$ may be the same or different and represents an $M_1$ or M group, at least one on each ring preferably representing an $M_1$ group).

Generally, diiodophenyl-diiodophenyl dimers will be less preferred than the diiodophenyl-triiodophenyl or triiodophenyl-triiodophenyl diners, due primarily to their reduced iodine loading, i.e. 4 rather than 5 or 6 iodines per diner molecule. Indeed the triiodophenyl-triiodophenyl diners are generally preferred due to their higher iodine loading.

For the monomers, the triiodophenyl compounds are again preferred.

The solubilizing groups M may be any of the non-ionizing groups conventionally used to enhance water solubility. Suitable groups include for example a straight chain or branched $C_{1-10}$-alkyl group, preferably a $C_{1-5}$ group, optionally with one or more $CH_2$ or CH moieties replaced by oxygen or nitrogen atoms and optionally substituted by one or more groups selected from oxo, hydroxy, amino, carboxyl derivative, and oxo substituted sulphur and phosphorus atoms. Particular examples include polyhydroxyalkyl, hydroxyalkoxyalkyl and hydroxypolyalkoxyalkyl and such groups attached to the phenyl group via an amide linkage such as hydroxyalkylaminocarbonyl, N-alkyl-hydroxyalkylaminocarbonyl and bis-hydroxyalkylaminocarbonyl groups. Preferred among such groups are those containing 1, 2, 3, 4, 5 or 6, especially 1, 2 or 3, hydroxy groups, e.g.

—CONH—$CH_2CH_2OH$
—CONH—$CH_2CHOHCH_2OH$
—CONH—CH$(CH_2OH)_2$
—CON$(CH_2CH_2OH)_2$ as well as other groups such as

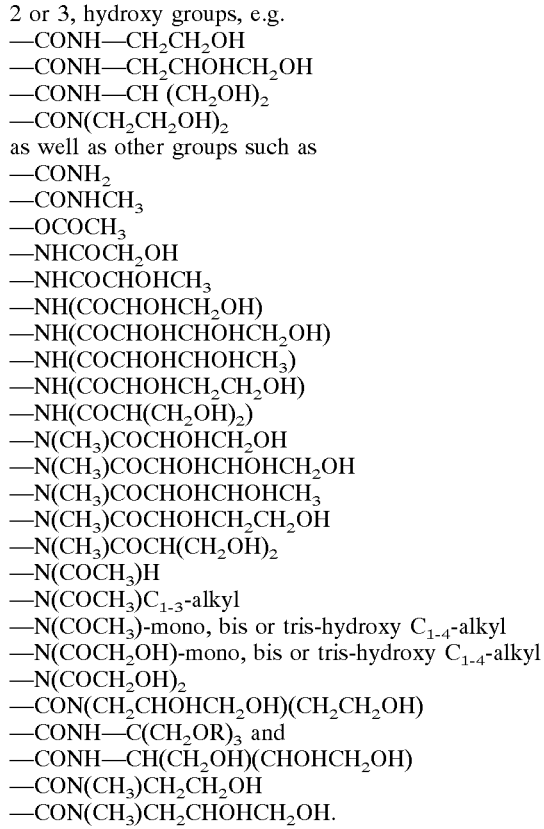

—$CONH_2$
—$CONHCH_3$
—$OCOCH_3$
—$NHCOCH_2OH$
—$NHCOCHOHCH_3$
—NH(COCHOHCH$_2$OH)
—NH(COCHOHCHOHCH$_2$OH)
—NH(COCHOHCHOHCH$_3$)
—NH(COCHOHCH$_2$CH$_2$OH)
—NH(COCH(CH$_2$OH)$_2$)
—N(CH$_3$)COCHOHCH$_2$OH
—N(CH$_3$)COCHOHCHOHCH$_2$OH
—N(CH$_3$)COCHOHCHOHCH$_3$
—N(CH$_3$)COCHOHCH$_2$CH$_2$OH
—N(CH$_3$)COCH(CH$_2$OH)$_2$
—N(COCH$_3$)H
—N(COCH$_3$)C$_{1-3}$-alkyl
—N(COCH$_3$)-mono, bis or tris-hydroxy C$_{1-4}$-alkyl
—N(COCH$_2$OH)-mono, bis or tris-hydroxy C$_{1-4}$-alkyl
—N(COCH$_2$OH)$_2$
—CON(CH$_2$CHOHCH$_2$OH)(CH$_2$CH$_2$OH)
—CONH—C(CH$_2$OR)$_3$ and
—CONH—CH(CH$_2$OH)(CHOHCH$_2$OH)
—CON(CH$_3$)CH$_2$CH$_2$OH
—CON(CH$_3$)CH$_2$CHOHCH$_2$OH.

In general, the M groups will preferably each comprise a mono-or polyhydroxy $C_{1-4}$-alkyl group such as 1,3-dihydroxyprop-2-yl or 2,3-dihydroxyprop-1-yl, attached to a primary amide group, wherein the primary amide group is linked to the phenyl ring by either the carbon atom in the carbonyl group or by the nitrogen.

For those compounds of the invention wherein $M_1$ represents a —CHOHCON(R$_1$)$_2$ group as previously is defined, one or more of the M groups may be a $C_{1-4}$ alkyl group substituted by at least one hydroxyl group and optionally linked to the phenyl ring via a carbonyl group, preferably —$CH_2OH$ or a propanediol.

Other such M groups as are conventional within the field of triiodophenyl X-ray contrast agents may also be used and the introduction of M groups onto iodophenyl structures may be achieved by conventional techniques.

Typically, the monomers of the present invention will contain one $M_1$ group though they may contain two or three $M_1$ groups, similarly the dimers will typically contain one $M_1$ group per $C_6R_5$ moiety but each $C_6R_5$ moiety may have two or three $M_1$ groups.

For the compounds of the invention first described, $M_1$ groups preferably comprise $C_{1-4}$-alkyl groups substituted by 1, 2, 3 or 4 hydroxy groups (e.g. hydroxymethyl, 2-hydroxyethyl, 2,3-bishydroxy-propyl, 1,3-bishysdroxyprop-2-yl, 2,3,4-trihydroxybutyl, and 1,2,4-trihydroxybut-2-yl) optionally connected to the phenyl ring via a CO, SO or $SO_2$ group (e.g. $COCH_2OH$ or $SO_2CH_2OH$).

In the dimeric compounds of the invention, the linker group X is conveniently a bond or a 1 to 7, e.g. 1, 2, 3 or 4, membered chain comprising carbon, nitrogen, oxygen or sulphur atoms, e.g.

a bond, a O, S, N or C one atom chain, a NN, NC, NS, CC or CO two atom chain, or a NCN, OCN, CNC, OCO, NSN, CSN, COC, OCC or CCC three atom chain, for example:

an oxygen atom or a group NR$^1$, CO, SO$_2$ or CR$_2^1$;

a group COCO, CONR$^1$, COCR$_2^1$, SOCR$_2^1$, SO$_2$NR$^1$, CR$_2^1$CR$_2^1$, CR$_2^1$NR$^1$ or CR$^1_2$O;

a group NR$^1$CONR$^1$, OCONR$^1$, CONR$^1$CO, CONR$^1$CR$^1_2$, OCOO, CR$^1_2$OCR$^1_2$, OCR$^1_2$CO, CR$^1_2$CONR$^1$, CR$^1_2$CR$^1_2$CR$^1_2$, COCR$^1$R$^1$CO, CR$^1_2$NR$^1$CR$^1_2$, CR$^1_2$SO$_2$NR$^1$, CR$^1_2$OCO or NR$^1$SO$_2$NR$^1$;

where R$^1$ is hydrogen or a $C_{1-6}$-alkyl or alkoxy group optionally substituted by hydroxy, alkoxy, oxa or oxo (e.g. a polyhydroxyalkyl, formyl, acetyl, hydroxyl, alkoxy or hydroxyalkoxy group) and where it is attached to a carbon atom R$^1$ may also be a hydroxyl group.

Where X is a 2–7 membered chain it is preferably non-symmetric.

When X provides a 4–7 atom linkage, conventional linker groups, such as for example those suggested by Justesa in WO-93/10078 or Bracco in U.S. Pat. No. 4,348,377 and WO-94/14478 may be used.

In general such linkages will comprise optionally aza or oxa substituted alkylene chains optionally carrying R$^1$ substituents, especially such groups terminating with imine nitrogen or, more preferably, carbonyl carbon atoms, preferably belonging to aminocarbonyl functional units within the chain. Hydroxylated chains, such as are found in iodixanol are particularly preferred.

Examples of such chains are NCCN, NCCCN, CNCCCNC, and CNCCN, eg.

—NR$^1$COCONR$^1$—
—NR$^1$COCR$^1_2$CONR$^1$—
—NR$^1$CR$^1_2$CR$^1$OHCR$^1_2$NR$^1$—
—CONR$^1$CR$^1_2$CONR$^1$— and
—N(COR$^1$)CR$^1_2$CR$^1$OHN(COR$^1$)—, e.g. as found in iotrolan, iofratol, ioxaglic acid and iodixanol, or as otherwise indicated in WO-94/14478.

Advantageously, in the diner compounds the X group is not symmetrical. This may be achieved for example by asymmetrical substitution of a symmetrical chain (e.g. N—C—N substituted as NHCONR$^1$) or by selection of an asymmetric chain (e.g. OCN substituted as OCONR$^1$). In particular, it is preferred that the linker group X should be polar and also that it should be hydrophilic.

Thus examples of preferred structures according to the intention include:

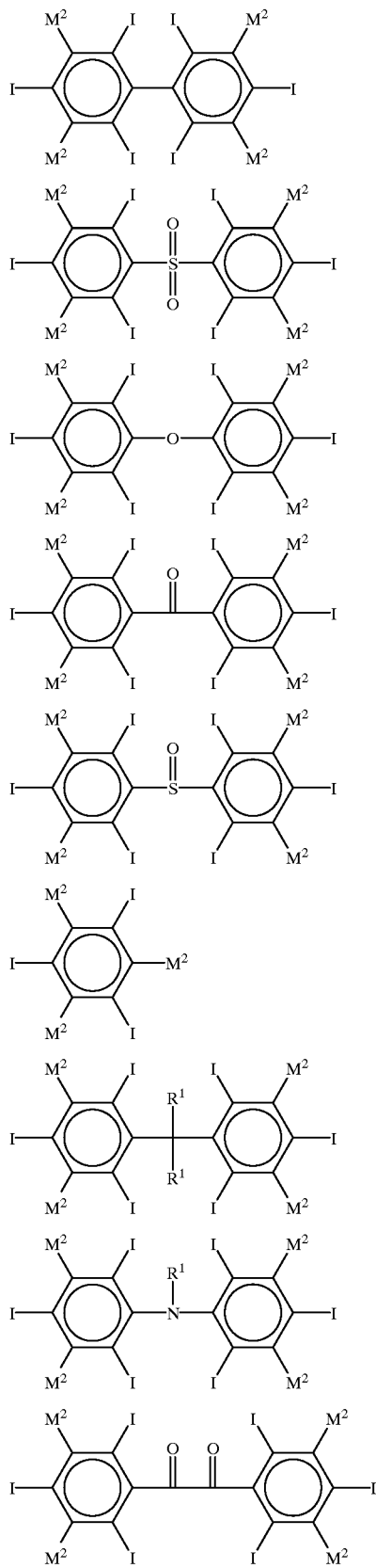
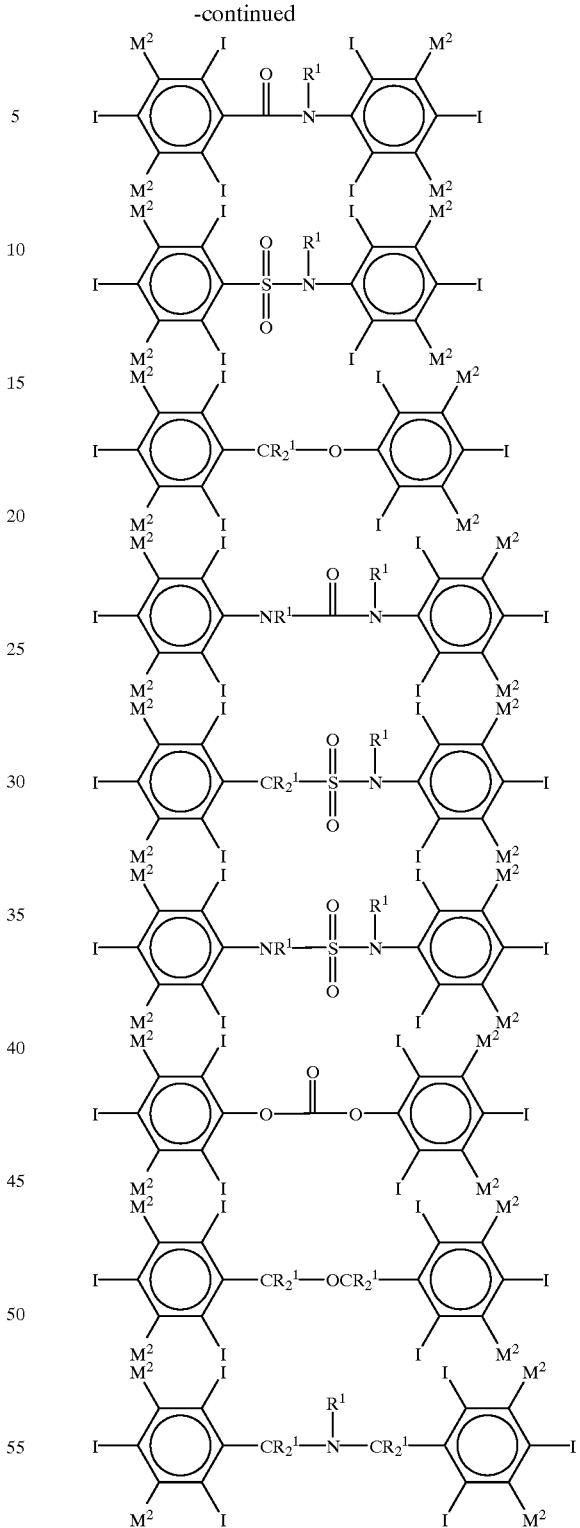

where each $M^2$ is $M_1$ or M, at least one in each compound (and preferably on each ring) being $M_1$, especially where at least one $M^2$ is a $C_{1-4}$-alkyl group substituted by 1, 2, 3 or 4 hydroxy groups (e.g. hydroxymethyl, 2-hydroxyethyl, 2,3-bishydroxy-propyl, 1,3-bishydroxyprop-2-yl, 2,3,4-trihydroxybutyl, and 1,2,4-trihydroxybut-2-yl) optionally connected to the phenyl ring via a CO, SO or $SO_2$ group (e.g. $COCH_2OH$ or $SO_2CH_2OH$), e.g. a hydroxyalkyl or hydroxyalkylcarbonyl group, in particular a hydroxymethyl, hydroxymethylcarbonyl, 2-hydroxyethyl or 2-hydroxyethylcarbonyl group, and where R¹ is hydrogen, hydroxyl, hydroxyalkyl (eg. 2-hydroxyethyl), acetyl or hydroxyalkylcarbonyl.

Particular preferred compounds are those of formula

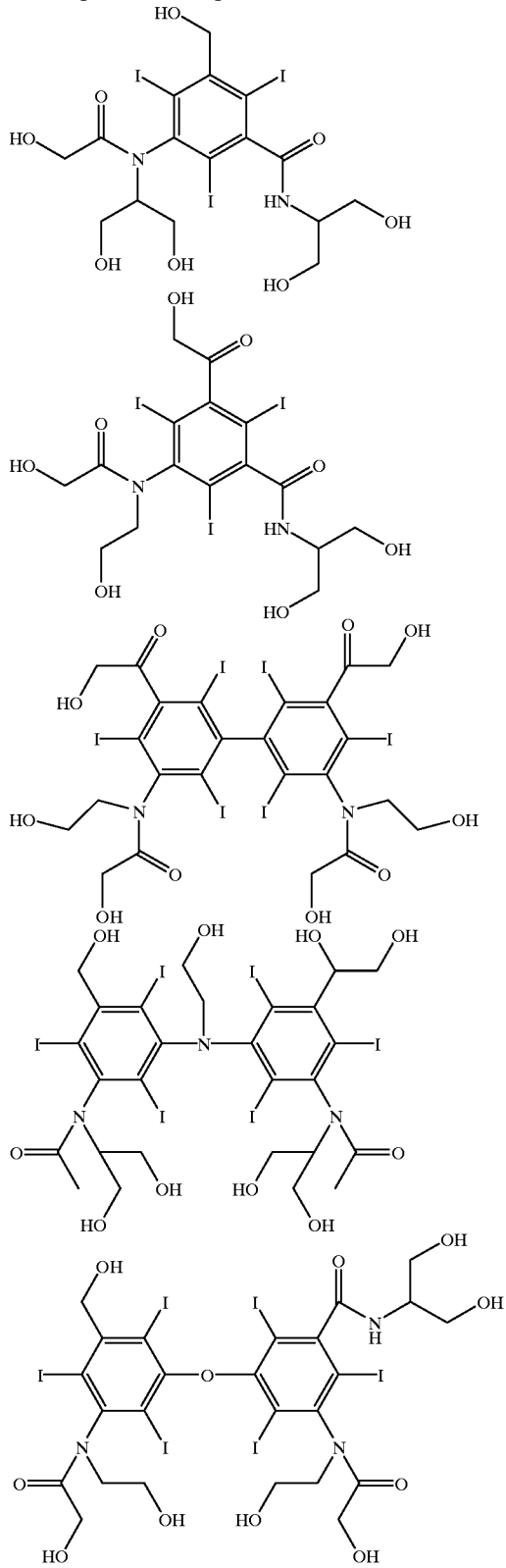

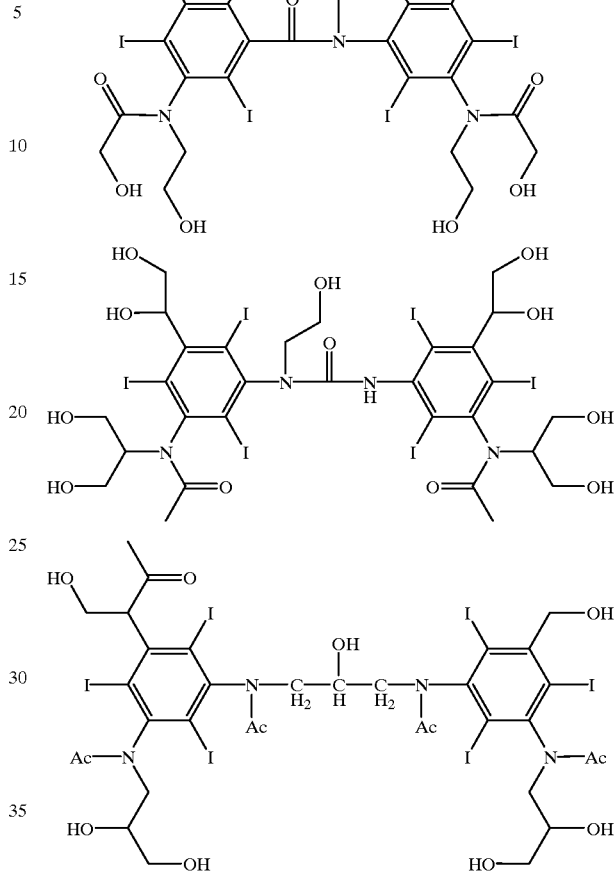

It is especially preferred that a hydroxymethyl $M_1$ group be present in the compounds of the invention and in particular that the compounds be hydroxymethyl substituted monomers Thus viewed from a further aspect the invention provides compounds of formula II (II)

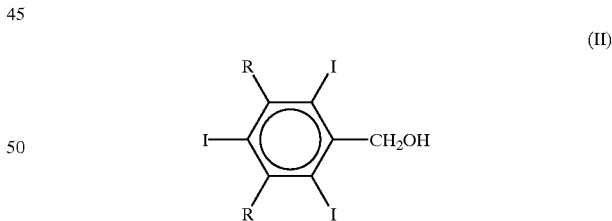

where each R group, which may be the same or different, is a non-ionic hydrophilic moiety (e.g. as defined above, preferably a group containing up to 10, more preferably 1 to 6, especially 2 to 4 hydroxyl groups), or one R group may be a second non-ionic triiodophenyl group, attached directly or via a non-ionic organic linker moiety.

Preferably the compounds of formula II are monomeric and especially preferably the two R groups are hydroxylated alkylcarbonylamino or hydroxylated alkylaminocarbonyl groups wherein the alkyl moieties contain 1 to 6 carbons and the amide nitrogens are optionally alkylated by optionally hydroxylated $C_{1-6}$ groups.

It has surprisingly been found that where the triiodophenyl ring carries a hydroxymethyl substituent, i.e. a small mono-hydroxylated group, especially high iodine concentrations can be achieved at relatively low or acceptable viscosities.

Thus viewed from a further aspect the invention provides a non-ionic iodinated X-ray contrast agent compound comprising a 1-hydroxymethyl-2,4,6-triiodobenzene ring structure, having a water solubility of at least 400 mgI/mL at 20° C., and having a viscosity of less than 30 mPas in aqueous solution at 20° C. and a concentration of 400 mgI/mL, preferably having a viscosity of less than 30 mPas in aqueous solution at 20° C. and a concentration of 450 mgI/mL.

Particularly preferably, the compounds have viscosities at 400 mgI/mL aqueous solution at 20° C. of less than 20 mPas.

Viewed from a further aspect the invention provides non-ionic 2,4,5-triiodobenzyl alcohols having a nitrogen attached substituent, preferably a hydroxylated substituent, at at least one of the 3- and 5-positions.

Particularly preferably the compounds of the invention have the formula III

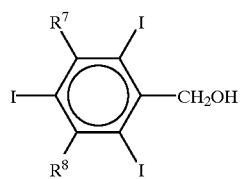

(III)

where $R^7$ and $R^8$, which may be the same or different, are $CH_2OH$, $R^{10}CONR^9$ or $R^{10}CONR^9$; each $R^9$, which may be the same or different, is hydrogen or a linear or branched hydroxylated $C_{1-6}$ alkyl; and each $R^{10}$ which may be the same or different is a linear or branched hydroxylated $C_{1-6}$ alkyl.

Examples of suitable $R^9$ and $R^{10}$ groups include H, $CH_2OH$, $CHOHCH_3$, $CH_2CH_2OH$, $CHOHCH_2OH$, $C(CH_3)(CH_2OH)_2$, $C(CH_2OH)_2$, $CH_2CHOHCH_2OH$ and $CH(CH_2OH)CHOHCH_2OH$.

Examples of suitable $R^{10}CONR^9$ groups include $HOCH_2CON(CH_2CHOHCH_2OH)$, $HOCH_2CONH$, $HOCH_2CON(CH_2CH_2OH)$, $CH_3CHOHCONH$, $CH_3CHOHCON(CH_2CH_2OH)$, $CH_3CHOHCON(CH_2CHOHCH_2OH)$, $HOCH_2CHOHCONH$, $HOCH_2CHOHCON(CH_2CH_2OH)$, $OHCH_2CHOHCON(CH_2CHOHCH_2OH)$, $(CH_2OH)_2(CH_3)CCONH$, $(CH_2OH)_2CHCONH$, $HOCH_2CH_2CONH$, $(CH_2OH)_3CCONH$, $HOCH_2CON(CH_2CHOHCH_2OH)$, and $HOCH_2CHOHCHOHCONH$.

Examples of particularly suitable $R^{10}N(R^9)CO$ groups include $HOCH_2CHOHCH_2NHCO$ and, $HOCH_2CHOHCH(CH_2OH)NHCO$, $(HOCH_2CH_2)_2NCO$, $HOCH_2CHOHCH_2N(CH_3)CO$, $(HOCH_2)_2CHNHCO$, $HOCH_2CH_2NHCO$, and $(HOCH_2)_3CNHCO$.

Further preferred compounds include those of formula IV

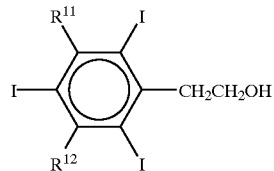

(IV)

wherein $R^{11}$ and $R^{12}$, which may be the same or different are groups $R^{10}CONR^9$ or $R^{10}NR^9CO$ as defined above with the proviso that at least one is a group $R^{10}CONR^9$.

In the compounds of formulae III and IV, and indeed in all the compounds according to the invention, the triiodophenyl ring substituents preferably carry a total of 4 to 7 hydroxyl groups.

In the compounds of formula III, conveniently: (i) one of $R^7$ and $R^8$ is N attached (and the other is CO attached) and the $R^{10}CO$ group is hydroxylated; (ii) both $R^7$ and $R^8$ are CO attached; or (iii) both $R^7$ and $R^8$ are nitrogen attached and at least one $R^{10}$ is other than $HOCH_2$, $HOCH_2CHOH$ or $CH_3CHOH$.

Preferably the compounds of the invention are monomers, i.e. n=0, and preferred among the mandelic amide compounds of the invention are those of formula II'

(II')

wherein each group R' is a hydrogen atom or a hydrophilic moiety M or $M_1$ as previously defined and $R_1$ is as previously defined. Preferably each group R' is an M or $M_1$ moiety.

Particularly preferred among the mandelic amide compounds of the invention are compounds of formulae III', IV' and V'.

(III')

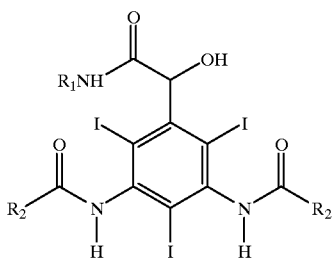

(IV')

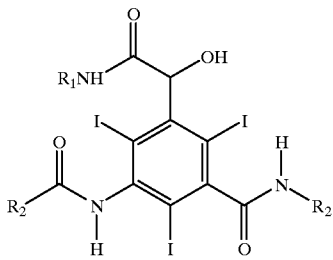

(V')

wherein R₁ is as previously defined and each R₂ which may be the same or different is a $C_{1-4}$ hydroxyalkyl group, preferably at least one R₂ group is a $C_{2-4}$ polyhydroxyalkyl group.

The two R₂ groups between them will preferably contain 3 to 5, more preferably 4 hydroxyl groups. The preferred number of hydroxyl groups will typically depend on the contribution to water solubility of the R₁ group and can therefore be adjusted accordingly.

In the compounds of formula V', the R₂ groups preferably each contain an even number of hydroxyl groups.

In the compounds of formula IV', the R₂ groups are preferably different.

Especially preferred compounds of the invention include,
(N,N'-bis(hydroxyacetyl)-3,5-diamino-2,4,6-triiodomandeloamide),
(N-(2,3-dihydroxypropionyl)-N'-hydroxyacetyl-3,5-diamino-2,4,6-triiodomandeloamide);
(N,N'-bis(2,3-dihydroxypropionyl)-3,5-diamino-2,4,6-triiodomandeloamide),
(N-(2,3,4-trihydroxybutyryl)-N'-hydroxyacetyl-3,5-diamino-2,4,6-triiodomandeloamide), particularly (N-(2R,3S,4-trihydroxybutyryl)-N'-hydroxyacetyl-3,5-diamino-2,4,6-triiodomandeloamide) and (N-(2R,3R,4-trihydroxybutyryl)-N'-hydroxyacetyl-3,5-diamino-2,4,6-triiodomandeloamide),
(N,N'-bis(2,3-dihydroxybutyryl)-3,5-diamino-2,4,6-triiodomandeloamide),
(N,N'-bis(2,4-dihydroxybutyryl)-3,5-diamino-2,4,6-triiodomandeloamide),
(N,N'-bis(2,2-bis(hydroxymethyl)-acetyl)-3,5-diamino-2,4,6-triiodomandeloamide),
(N,N'-bis(2,3,4-trihydroxybutyryl)-3,5-diamino-2,4,6-triiodomandeloamide), particularly (N,N'-bis(2R,3S,4-trihydroxybutyryl)-3,5-diamino-2,4,6-triiodomandeloamide), and
(5-(2,3-dihydroxypropionyl)amino-3-N-(2,3-dihydroxypropyl)carbamido-2,4,6-triiodomandeloamide).

An especially preferred compound is N-(2R,3S,4-trihydroxybutyryl)-N'-hydroxyacetyl-3,5-diamino-2,4,6-triiodomandelamide.

It should be appreciated that the invention relates to all stereoisomeric forms of a given compound of formula I as defined herein The M₁ group of the mandelic amides as defined herein contains one chiral center and M groups may also have chiral centers, giving rise to different diastereomers and enantiomers. In general, the physical and biological properties of the different stereoisomers do not differ widely and a is particular contrast medium may contain a mixture of isomers of the active ingredient. In certain circumstances, e.g. relating to obtaining regulatory approval, it may be more convenient to prepare a contrast agent which contains a limited number of stereoisomers. Restrictions on the stereoisomers present in the final contrast medium may typically be a result of the chosen starting material which may be readily available in enantiomerically pure form.

The compounds of the invention may be prepared by any of the methods of synthesis of organic molecules known in the art and described in the literature. Advantageously, where appropriate, the compounds may be prepared by initial formation of a mandelic amide, then iodination of the phenyl ring and finally substitution of the phenyl ring with the solubilising groups M. Where desired the linker group X may be produced by modification, e.g. substitution, oxidation or reduction, of a precursor linker, e.g. in a precursor monomer.

The compounds of the invention may be prepared by removal of a hydroxy or amino protecting group from a compound of formula I which additionally incorporates such a protecting group. Such a method of preparation constitutes a further aspect of the present invention.

A typical reaction scheme for the preparation of a compound according to the invention is shown below

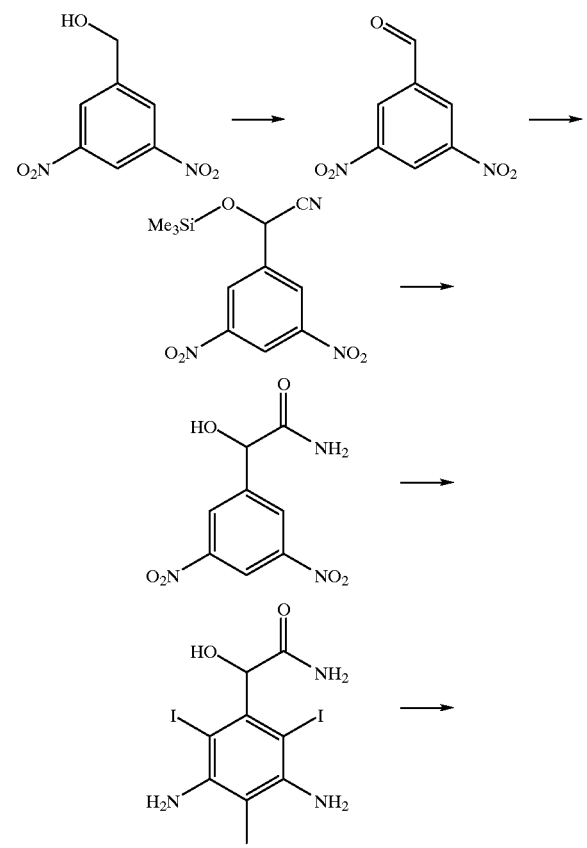

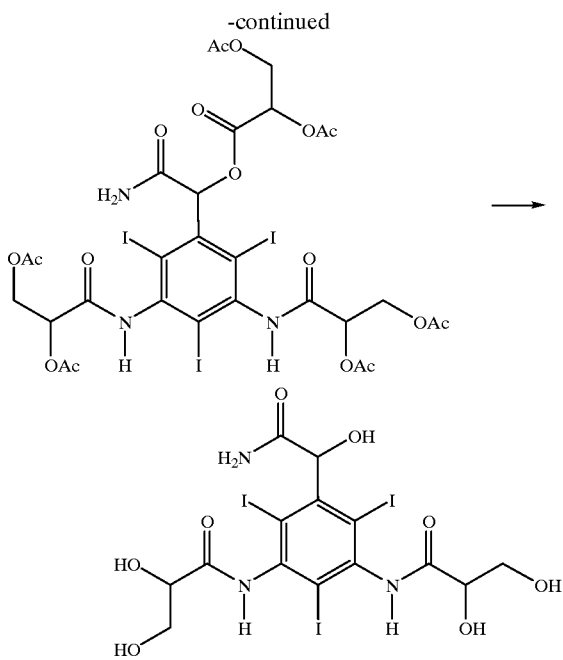

The compounds of the invention may in general be prepared in two or three stages: (a) dimer formation (where necessary), (b) iodination of phenyl groups and (c) substitution of phenyl groups and/or optionally linker moieties by solubilizing moieties.

While, in theory, stages (a), (b) and (c) can be performed in any order, it will generally be preferred to perform the dimer formation step before the iodination step and, for reasons of economy, it will be preferred to perform the iodination step at as late a stage in the synthesis as is feasible so as to reduce iodine wastage. The diner formation stage may itself be a multi-step procedure with an appropriate activated linker first being attached to one monomer before the resulting linker-monomer conjugate is reacted with a second monomer. Alternatively, dimer formation may be by way of reaction of similarly or cooperatively substituted monomers with the conjugation of the monomers leading to diner formation.

Where desired the linker group X may be produced by modification, e.g. substitution, oxidation or reduction, of a precursor linker, e.g. in a precursor monomer.

For the monomer compounds, especially those where ring substitution is asymmetric, iodine loading will generally be effected before or after partial substitution of the phenyl ring with R groups.

In all cases, conventional synthetic routes well known in the literature (eg methods analogous to those used and described for the production of the compounds referred to in WO-94/14478) may be used.

The compounds of the invention may be used as X-ray contrast agents and to this end they may be formulated with conventional carriers and excipients to produce diagnostic contrast media.

Thus viewed from a further aspect the invention provides a diagnostic composition comprising a compound of formula I together with at least one physiologically tolerable carrier or excipient, e.g. in aqueous solution in water for injections optionally together with added plasma ions or dissolved oxygen.

The contrast agent compositions of the invention may be at ready-to-use concentrations or may be formulated in concentrate form for dilution prior to administration. Generally compositions in ready-to-use form will have iodine concentrations of at least 100 mgI/ml, preferably at least 150 mgI/ml, with concentrations of at least 300 mgI/ml, e.g. 320 to 600 mgI/ml or 400 to 550 mgI/ml being generally preferred. The higher the iodine concentration the higher the diagnostic value but equally the higher the solution's viscosity and osmolality. Normally the maximum iodine concentration for a given compound will be determined by its solubility, and by the upper tolerable limits for viscosity and osmolality.

For contrast media which are administered by injection, the desirable upper limit for solution viscosity at ambient temperature (20° C.) is 30 mPas; however viscosities of up to 50 or even up to 60 mPas can be tolerated although their use in paediatric radiography will then generally be contraindicated. For contrast media which are to be given by bolus injection, e.g. in angiographic procedures, osmotoxic effects must be considered and preferably osmolality should be below 1 Osm/kg $H_2O$, especially below 850 mOsm/kg $H_2O$.

With the compounds of the invention, such viscosity, osmolality and iodine concentration targets can readily be met. It may however be desirable to include plasma cations for their cardioprotective effect. Such cations will desirably be included in the ranges suggested in WO-90/01194 and WO-91/13636.

Preferred plasma cation contents for the contrast media of the invention, especially contrast media for angiography, are as follows:

sodium 2 to 100, especially 15 to 75, particularly 20 to 70, more particularly 25 to 35 mM calcium up to 3.0, preferably 0.05 to 1.6, especially 0.1 to 1.2, particularly 0.15 to 0.7 mM potassium up to 2, preferably 0.2 to 1.5, especially 0.3 to 1.2, particularly 0.4 to 0.9 mM magnesium up to 0.8, preferably 0.05 to 0.6, especially 0.1 to 0.5, particularly 0.1 to 0.25 mM The plasma cations may be presented, in whole or in part, as counterions in ionic contrast agents. Otherwise they will generally be provided in the form of salts with physiologically tolerable counteranions, e.g. chloride, sulphate, phosphate, hydrogen carbonate, etc., with plasma anions especially preferably being used.

Besides plasma cations, the contrast media may contain other counterions where the compound of formula I is ionic and such counterions will of course preferably be physiologically tolerable. Examples of such ions include alkali and alkaline earth metal ions, ammonium, meglumine, ethanolamine, diethanolamine, chloride, phosphate, and hydrogen carbonate. Other counterions conventional in pharmaceutical formulation may also be used. The compositions moreover may contain further components conventional in X-ray contrast media, e.g. buffers, etc.

Viewed from a still further aspect the present invention provides a method of generating an enhanced image of at least part of a human or non-human animal body which comprises administering to said body a compound of formula I and generating an image of at least part of said body to which said compound distributes.

In a yet further aspect, the invention provides the use of a compound of formula I for the manufacture of a diagnostic composition for use in a method of diagnosis which involves generating an image.

Publications referred to herein are incorporated herein by reference.

The invention will now be described further with reference to the following non-limiting Examples. Stereochemistry has been given for some examples but this should not be regarded in any way as limiting the compounds of the invention.

EXAMPLE 1

1,3,5-Triiodo-2,4-di(1,2,3-trihydroxy-1-propyl)-6-(3-hydroxy-1-propen-1-yl)benzene a, 1,3,5-Triiodo-2,4,6-trimethylbenzene Iodine (19.0 g, 75 mmol) was dissolved in carbon tetrachloride (75 ml). Mesitylene (7.0 ml, 50 mmol) and bis(trifluoroacetoxy)phenyl iodide (35.5 g, 82 mmol) were added and the solution was stirred at ambient temperature for 2 hours. The precipitate, which was collected by filtration, was washed with cold carbon tetrachloride and dried. Yield: 20.5 g (82%).

$^1$H NMR (CDCl$_3$): 3.31 (s).

b. 1,3,5-Triiodo-2,4,6-triacetoxymethylbenzene

Triiodomesitylene (19.5 g, 39 mmol) was added to glacial acetic acid (200 ml) containing acetic anhydride (400 ml) and concentrated sulfuric acid (40 ml). Solid potassium permanganate (24.6 g, 156 mmol) was then added in small portions over a period of 3 h. After stirring for 16 h, the solvent was evaporated and water (200 ml) is was added. The aqueous suspension was extracted with dichloromethane (250 ml) and the organic phase was washed with water (3×50 ml), dried (MgSO$_4$) and evaporated. The solid residue was suspended in acetone and the white crystalline product was collected by filtration. Yield: 9.3 g (35%).

$^1$H NMR (CDCl$_3$): 566 (s, 6H), 2.20 (s, 9H).

c. 1,3,5-Triiodo-2,4,6-trihydroxymethylbenzene 1,3,5-Triiodo-2,4,6-triacetoxymethylbenzene (9.3 g, 13.8 mmol) was suspended in methanol (120 ml) and K$_2$CO$_3$ (0.32 g, 2.3 mmol) was added. The mixture was stirred at ambient temperature for 16 h, and, after neutralization of the solution with 2M aqueous HCl, the organic solvent was evaporated. The residue was suspended in water and the white solid was collected by filtration and washed with water, methanol and ether. Yield: 7.1 g (94%).

$^1$H NMR (DMSO-d$_6$): 5.08 (s, 6H), 3.35 (br, 3H).

d. 1,3,5-Triiodobenzene-2,4,6-trialdehyde 1,3,5-Triiodo-2,4,6-trihydroxymethylbenzene (4.5 g, 8.2 mmol) was dissolved in DMSO (80 ml). Triethylamine (51.7 ml, 371 mmol) and pyridine.SO$_3$ (11.8 g, 74.2 mmol) were added and the mixture was stirred for two hours. The two phases were separated and the lower phase was cooled to 0° C., poured into water (150 ml) and stirred for 30 min at 0° C. The white solid was collected by filtration, washed with water and dried. Yield: 3.0 g (67%).

$^1$H NMR (DMSO-d$_6$): 9.64 (s).

e. 1,3,5-Triiodo-2,4,6-tris(2-prop-1-enoic acid)benzene methyl ester

Sodium hydride (194 mg 80% in mineral oil, 6.5 mmol) was dissolved in DMSO (13 ml) and triethylphosphonoacetate (1.16 ml, 5.80 mmol) was added. After stirring the solution for 30 min, 1,3,5-triiodobenzene-2,4,6-trialdehyde (700 mg, 1.30 mmol) was added and the reaction mixture was stirred for 16 h. Water (200 ml) was then added and the pH was adjusted to 1 with 2 M aqueous HCl. The slurry was extracted with dichloromethane (2×200 ml) and the combined organic phases were washed with water (3×50 ml), dried (MgSO$_4$) and evaporated. Purification by column chromatography (silica gel CH$_2$Cl$_2$-methanol 99:1) gave the pure product as a white solid. Yield: 426 mg (44%).

$^1$H NMR (CDCl$_3$): 7.48 (d, 3H, J 16.2 Hz), 5.95 (d, 3H, J 16.2 Hz), 4.30 (q, 6H, J 7.2 Hz), 1.36 (t, 9H, J 7.2 Hz).

f. 1,3,5-Triiodo-2,4,6-tris(1-hydroxyprop-en-3-yl)benzene 1,3,5-Triiodo-2,4,6-tris(2-prop-1-enoic acid)benzene methyl ester (650 mg, 0.87 mmol) was dissolved in toluene (10 ml) and diisobutylaluminium hydride (5.44 ml of a 1.2 M solution in toluene) was added at 0° C. After stirring for 40 min at 0° C., the solution was poured into methanol (50 ml) and the resulting slurry was stirred for another 45 minutes. The solids were filtered off and the solution was evaporated giving a white solid residue which was purified by trituration with diethyl ether. Yield: 510 mg (94%).

$^1$H NMR (CD$_3$OD): 6.44 (d, 3H, J 16.0 Hz), 5.57 (dt, 3H, J$_d$ 16.0 Hz, J$_t$ 5.8 Hz), 4.23 (m, 6H).

g. 1,3,5-Triiodo-2,4,6-tris(1-acetoxyprop-en-3-yl)benzene 1,3,5-Triiodo-2,4,6-tris(1-hydroxyprop-en-3-yl)benzene (560 mg, 0.90 mmol) was dissolved in a mixture of pyridine (8 ml) and acetic anhydride (8 ml). After stirring at ambient temperature for 16 hours, the solvent was evaporated and the residue was purified by preparative HPLC (RP-18, CH$_3$CN: H$_2$O 80:20). Yield 310 mg (46%).

$^1$H NMR (CDCl$_3$): 6.46 (dt, 3H, J$_d$ 16.2 Hz, J$_t$ 1.6 Hz), 5.68 (dt, 3H, J$_d$ 16.2 Hz, J$_t$ 5.6 Hz), 4.83 (dd, 6H, J$_1$ 5.6 Hz, J$_2$ 1.6 Hz), 2.12 (s, 9H).

$^{13}$CNMR (CDCl$_3$): 170.6, 146.3, 140.9, 131.5, 98.7, 63.5, 20.9.

h. 1,3,5-Triiodo-2,4-di(1,2,3-trihydroxy-1-propyl)-6-(3-hydroxy-1-propen-1-yl)benzene 1,3,5-Triiodo-2,4,6-tris(1-acetoxyprop-en-3-yl)benzene (100 mg, 0.133 mmol) was dissolved in formic acid (5 ml) containing hydrogen peroxide (0.054 ml). The mixture was stirred at ambient temperature for 21 hours and the solvent was evaporated. Methanol (5 ml) was added followed by solid K$_2$CO$_3$ (195 mg), and, after stirring for 1 hour, the solvent was evaporated. The product was purified by preparative HPLC (CH$_3$CN: H$_2$O 3:97).

$^1$H NMR (D$_2$O): 6.45 (d, 1H, J 16.0 Hz), 5.40–5.55 (m, 1H), 4.54–4.90 (m, 11H), 4.23–4.31 (m, 2H), 3.62–3.91 (m, 4H).

MS (ESP): 692 (M$^+$).

EXAMPLE 2

1,3,5-Triiodo-2,4,6-tri(1,2,3-trihydroxy-1-propyl) benzene 1,3,5-Triiodo-2,4,6-tris(1-acetoxyprop-en-3-yl)benzene (100 mg, 0.133 mmol, from Example 1g) was dissolved in formic acid (5 ml) containing hydrogen peroxide (0.081 ml). The mixture was stirred at room temperature for 40 hours and the solvent was evaporated. Methanol (5 ml) was added followed by solid K$_2$CO$_3$ (195 mg), an, after stirring for 1 h, the solvent was evaporated. The product was purified by preparative HPLC (CH$_3$CN:H$_2$O 3:97).

$^1$H NMR (CD$_3$OD): 4.57–4.94 (m, 15H), 3.62–3.99 (m, 6H).

MS (ESP): 744 (M+18).

EXAMPLE 3

N-Acetyl-3-hydroxymethyl-5-(2,3-dihydroxypropylaminocarbonyl)-N-(2,3-dihydroxypropyl)-2,4,6-triiodoaniline a. 1-Hydroxymethyl-3-nitro-5-benzoic acid methyl ester 1-Nitroisophthalic acid monomethyl ester (22.5 g, 100 mmol) was dissolved in dry THF (675 ml) and BF$_3$.Et$_2$O (25.2 ml, 200 mmol) was added. NaBH$_4$ (5.1 g, 135 mmol) was then added portionwise during 1 h. After stirring for 2 additional h, ethanol (20 ml) was added slowly followed by water (200 ml) and diethyl ether (400 ml). The phases were separated and the aqueous phase was extracted once with diethyl ether (100 ml). The combined organic phases were washed with a saturated aqueous solution of NaHCO$_3$, dried ($Na_2SO_4$) and evaporated. Yield: 20 g (96%). HPLC analysis indicated >95% purity of the product.

$^1$H NMR ($CDCl_3$): 8.72 (s, 1H), 8.42 (s, 1H), 8.32 (s, 1H), 4.86 (s, 2H), 3.97 (s, 3H), 2.37 (br s, 1H).

b. 1-Hydroxymethyl-3-nitro-5-(2,3-dihydroxypropylaminocarbonyl)benzene

The methyl ester from Example 3a (20.5 g, 97 mmol) was mixed with 2,3-dihydroxypropylamine (9.6 g, 106 mmol) and the mixture was heated to 90° C. After 45 min, the pressure was reduced to 200 mm Hg and heating was continued for 2 h. The crude product, which was >95% pure according to HPLC analysis, was used without further purification in the next step. Yield: 22.8 g(87%).

$^1$H NMR ($CD_3OD$): 8.57 (s, 1H) 8.38 (s, 1H), 8.19 (s, 1H), 4.77 (s, 2H), 3.81–3.88 (m, 1H), 3.39–3.63 (m, 4H).

c. 3-Hydroxymethyl-5-(2,3-dihydroxypropylaminocarbonyl)aniline

1-Hydroxymethyl-3-nitro-5-(2,3-dihydroxypropylaminocarbonyl)benzene (12.0 g, 44.4 mmol) was hydrogenated in methanol (150 ml) at 60 psi $H_2$ using Pd/C (10%, 100 mg) as the catalyst. The catalyst was removed by filtration and the residue was evaporated. Addition of methanol (10 ml) precipitated the product as a white solid which was filtered off and dried. Yield: 6.6 g (62%).

$^1$H NMR ($CD_3OD$): 7.05–7.09 (m, 1H), 6.98–7.03 (m, 1H), 6.83–6.87 (m, 1H), 4.53 (s, 2H), 3.77–3.85 (m, 1H), 3.8–3.59 (m, 4H), 3.32–3.42 (m, 1H)

MS (ESP, m/e): 241 ([M+1]$^+$, 100%).

d. 3-Hydroxymethyl-5-(2,3-dihydroxypropylaminocarbonyl)-2,4,6-triiodoaniline

3-Hydroxymethyl-5-(2,3-dihydroxypropylaminocarbonyl)aniline (500 mg, 2.1 mmol) was dissolved in water (175 ml) and an aqueous solution of $KICl_2$ (70%, w/w) was added in portions of 0.1 ml during 8 h. A total amount of 1.0 ml $KICl_2$ solution was added. After a total reaction time of 6 h, the solution was extracted with ethyl acetate (1000 ml) which was separated and washed with an aqueous solution of $Na_2S_2O_3$ (0.2M, 100 ml). Evaporation followed by purification by preparative HPLC gave 432 mg (33%) of the pure product.

$^1$H NMR ($CD_3OD$): 5.10 (s, 2H), 3.90–3.98 (m, 1H), 3.72 (ddd, $J_1$=0.7 Hz, $J_2$=4.2 Hz, $J_3$=11.4 Hz), 1H), 3.60 (dd, $J_1$=6.0 Hz, $J_2$=11.4 Hz, 1H), 3.49 (ddd, $J_1$=1.2 Hz, $J_2$=6.0 Hz, $J_3$=13.5 Hz, 1H), 3.37 (ddd, $J_1$=1.2 Hz, $J_2$=6.1 Hz, $J_3$=13.2 Hz, 1H), 2.62 (s, 1H), 2.28 and 2.34 (2s, 2H).

MS (ESP, m/e): 618 (M$^+$, 100%), 640 ([M+Na]$^+$, 55%).

e. N-acetyl-3-acetoxymethyl-5-(2,3-diacetoxypropylaminocarbonyl1)-2,4,6-triiodoaniline 3-Hydroxymethyl-5-(2,3-dihydroxypropylaminocarbonyl)-2,4,6-triiodoaniline (3.3 g, 5.3 mmol) was suspended in glacial acetic acid (12 ml) containing acetic anhydride (48 ml) and concentrated sulfuric acid (0.08 ml). The mixture was stirred at 60° C. for 3 h, allowed to cool to room temperature, and $CH_2Cl_2$ (100 ml) and water (100 ml) were added. The organic phase was washed with water (3×50 ml) and a saturated aqueous solution of $NaHCO_3$ (2×50 ml). After drying ($MgSO_4$) and evaporation, the residue was dissolved in a mixture of $CH_2Cl_2$ and methanol (9:1) and filtered through a short silica pad and evaporated. Yield: 3.0 g (71%).

$^1$H NMR ($CDCl_3$): 8.27–8.32 (m, 1H), 5.51 (s, 2H) 5.18–5.22 (m, 1H), 4.17–4.42 (m, 2H), 3.67–3.84 (m, 1H), 3.41–3.60 (m, 1H), 2.56 (s, 3H), 2.04–2.14 (8s, 12H).

MS (ESP, m/e): 786 (M$^+$, 100%), 809 ([M+Na]$^+$, 81%).

f. N-Acetyl-3-hydroxymethyl-5-(2,3-dihydroxypropylaminocarbonyl)-N-(2,3-dihydroxypropyl)-2,4,6-triiodoaniline N-acetyl-3-acetoxymethyl-5-(2,3-diacetoxypropylaminocarbonyl)-2,4,6-triiodoaniline (1.0 g, 1.27 mmol) was suspended in a mixture of methanol (6 ml) and water (30 ml) and pH was adjusted to 12.0 using a 2 M aqueous solution of NaOH. After stirring for 1 h, 1-bromo-2,3-propanediol (0.99 g, 6.4 mmol) was added and the pH was adjusted to 11.6 using a 2 M aqueous solution of HCl. 1-Bromo-2,3-propanediol (0.99 g, 6.4 mmol) was again added after 16 and 18 h and after 24 h, pH was adjusted to 6.5 using a 2 M aqueous solution of HCl. After evaporation, the residue was purified by preparative HPLC. Yield: 0.373 g (40%).

$^1$H NMR ($D_2O$): 5.20 (s, 2H), 3.23–3.99 (m, 12H) 1.79 (2s, 3H).

MS (ESP, m/e): 734 (M$^+$, 60%), 756 ([M+Na]$^+$, 100%).

EXAMPLE 4

N,N'-bis(hydroxyacetyl)-3,5-diamino-2,4,6-triiodobenzylalcohol a. 3,5-Diaminobenzylalcohol A solution of 3,5-dinitrobenzylalcohol (2.20 g, 11.1 mmol) in methanol (90 ml) and a Pd/C catalyst (10%, 100 mg) was hydrogenated in a Parr apparatus at 60 psi. The solution was filtered and the solvent was removed by evaporation. The crude product was used without purification in the next step.

$^1$H NMR ($CDCl_3$): 6.12–6.14 (m, 2H), 5.96–5.98 (m, 1H), 4.51 (s, 2H), 3.60 (br s, 4H).

b. 3,5-Diamino-2,4,6-triiodobenzylalcohol

The crude product from the previous example dissolved in a mixture of methanol (310 ml) and water (60 ml) and pH was adjusted to 1.5 using a 4 M aqueous solution of HCl. A solution of $KICl_2$ (70%, 11.2 g) was added dropwise at such a rate, that the color disappeared between each addition. After stirring for 5 additional min, the precipitate was filtered off and washed with water (3×50 ml), ether (3×50 ml) and dried. Yield: 4.50 g (80%).

$^1$H NMR (DMSO-$d_6$): 5.20 (s, 4H), 4.81–4.94 (m, 3H).

c. 3,5-Diamino-2,4,6-triiodobenzylacetate 3,5-Diamino-2,4,6-triiodobenzylalcohol (4.42 g, 8.56 mmol) was dissolved in a mixture of pyridine (50 ml) and acetic anhydride (2.5 ml) and the mixture was stirred at room temperature for 16 h. The solvents were evaporated and the residue was washed with ether (3×50 ml), water (3×50 ml) and dried. Yield: 4.52 g (95%).

$^1$H NMR (DMSO-$d_6$): 5.35 (s, 2H); 5.28 (s, 4H), 2.04 (s, 3H).

$^{13}$C NMR (DMSO-$d_6$): 170.5, 148.1, 139.0, 78.0, 73.6, 70.0, 20.8.

d. 3,5-Bis(acetoxyacetylamino)-2,4,6-triiodobenzylacetate 3,5-Diamino-2,4,6-triiodobenzylacetate (5.58 g, 10 mmol) was mixed with acetoxyacetyl chloride (3.22 ml, 30 mmol) and dimethylacetamide (50 ml) and the mixture was stirred for 17 h. Ether (600 ml) was added, and after 20 min. the precipitate was collected, washed with water (3×50 ml) and dried. Recrystallization from acetonitrile gave 3.3 g (44%) of the pure product.

$^1$H NMR (DMSO-d6): 10.27 and 10.19 (2s, 2:1, 2H), 5.51 (s, 2H), 4.66 (s, 4H), 2.13 (s, 3H), 2.12 (s, 3H), 2.06 (s, 3H).

e. N,N'-bis(hydroxyacetyl)-3,5-diamino-2,4,6-triiodobenzylalcohol 3,5-Bis(acetoxyacetylamino)-2,4,6-triiodobenzylacetate (152 mg, 0.2 mmol) was dissolved in a mixture of methanol (6 ml) and 1 M aqueous NaOH (2 ml) and the solution was stirred for 2 h at room temperature. After neutralization with

EXAMPLE 5

N,N'-Bis(hydroxyacetyl)-N-(2-hydroxyethyl)-3,5-diamino-2,4,6-triiodobenzylalcohol a. N,N'-Bis(acetoxyacetyl)-N-(2-acetoxyethyl)-3,5-diamino-2,4,6-triiodobenzylacetate 3,5-Bis(acetoxyacetylamino)-2,4,6-triiodobenzylacetate (2.15 g, 2.84 mmol) was dissolved in a mixture of DMSO (5 ml) and dimethylacetamide (5 ml) containing $Cs_2CO_3$ (1.0 g, 3.07 mmol) and 2-bromoethyl acetate (0.31 ml, 2.84 ml). The mixture was stirred at room temperature for 48 h, ether (100 ml) and aqueous $NaH_2PO_4$ buffer were added and the organic phase was washed with water and dried. Purification by preparative HPLC gave 520 mg (22%) of the product.

$^1$H NMR ($CDCl_3$): 7.86 (s, 1H), 5.66 (s, 2H), 4.80 (s, 2H), 3.81–4.44 (m, 6H), 2.13–2.27 (m, 12H).

MS (ESP, m/e): 845 ([M+1]$^+$, 100%), 866 ([M+Na]$^+$, 24%).

b. N,N'-Bis(hydroxyacetyl)-N-(2-hydroxyethyl)-3,5-diamino-2,4,6-triiodobenzylalcohol N,N'-Bis(acetoxyacetyl)-N-(2-acetoxyethyl)-3,5-diamino-2,4,6-triiodobenzylacetate (0.50 g, 0.59 mmol) was dissolved In a mixture of methanol (5 ml), water (5 ml) and aqueous 1 M NaOH (1 ml). The solution was stirred for 2 h, pH was adjusted to 2 using aqueous HCl and the product was purified by preparative HPLC. Yield: 240 mg (679).

$^1$H NMR DMSO-$d_6$): 9.85 (br s, 1H), 5.77 (br s, 1H), 4.79–5.26 (m, 3H), 3.20–3.71 (m, 6H).

MS (ESP, m/e): 676 (M$^+$, 57%), 698 ([M+Na]$^+$, 100%).

EXAMPLE 6

N,N'-Bis(hydroxyacetyl)-N,N'-bis(2-hydroxyethyl)-3,5-diamino-2,4,6-triiodobenzylalcohol 3,5-Bis(acetoxyacetylamino)-2,4,6-triiodobenzylacetate (190 mg, 0.25 mmol), prepared according to Example 4, was dissolved in dimethylacetamide (5 ml) under an argon atmosphere. 2-Bromoethyl acetate (0.22 ml, 2.0 mmol) and $K_2CO_3$ (138 mg, 1.0 mmol) were added. After 16 h, DMSO (1.5 ml), 2-bromoethyl acetate (0.22 ml, 2.0 mmol) and $K_2CO_3$ (138 mg, 1.0 mmol) were added and the suspension was stirred for another 24 h. Aqueous $NaH_2PO4$ was added and the resulting solution was extracted with ether (3×25 ml). The combined organic phases were washed with water (4×20 ml) and then dried ($MgSO_4$). The solvent was removed by evaporation and the residue, a colorless oil, was dissolved in a mixture of methanol (3 ml) an 1 M aqueous NaOH (3 ml). The solution was stirred for 1 h, pH was adjusted to 6 using aqueous HCl and the solvents were removed by evaporation. Purification by preparative HPLC gave 60 mg (33%) of the product.

MS (ESP, m/e): 720 (M$^+$, 100%), 742 ([M+Na]$^+$, 36%).

EXAMPLE 7

N,N'-Bis(hydroxyacetyl)-N-(2,3-dihydroxypropyl)-3,5-diamino-2,4,6-triiodobenzylalcohol a. N,N'-Bis(acetoxyacetyl)-N-[(2,2-dimethyl-1,3-dioxolane-4-yl)-methyl]-3,5-diamino-2,4,6-triiodobenzylacetate 3,5-Bis(acetoxyacetylamino)-2,4,6-triiodobenzylacetate (90 mg, 0.12 mmol), prepared according to Example 4, was dissolved in dimethylacetamide (3 ml) and DMSO (3 ml). 4-Bromomethyl-2,2-dimethyl-1,3-dioxolane (0.097 g, 0.5 mmol) and $CS_2CO_3$ (0.10 g, 0.3 mmol) were added and the solution was stirred at room temperature for 48 h. Aqueous $NaH_2PO_4$ was added and the solution was extracted with ether (3×25 ml). The combined organic phases were washed with water (3×15 ml), dried ($MgSO_4$) and evaporated. Purification by preparative HPLC gave 36 mg (35%) of the pure product.

$^1$H NMR (DMSO-$d_6$) 10.30 (br s, 1H), 5.53 (s, 2H), 3.61–4.68 (m, 9H), 2.13 (s, 3H), 2.07 (s, 3H), 2.06 (s, 3H), 1.17–1.34 (m, 6H).

MS (ESP, m/e): 894 ([M+Na]$^+$, 100%), 910 ([M+K]$^+$, 11%).

b. N,N'-Bis(hydroxyacetyl)-N-(2,3-dihydroxypropyl)-3,5-diamino-2,4,6-triiodobenzylalcohol N,N'-Bis(acetoxyacetyl)-N-[(2,2-dimethyl-1,3-dioxolane-4-yl)-methyl]-3,5-diamino-2,4,6-triiodobenzylacetate (36 mg, 0.042 mmol) was dissolved in a mixture of methanol (3 ml) and water (4 ml) and the pH was adjusted to 12 using a 1 M aqueous solution of NaOH. After stirring for 2 h, pH was adjusted to 1 using 1 M aqueous HCl and stirring was continued for 16 h. The solution was neutralized with an aqueous $NaH_2PO_4$ buffer, the solvents were removed by evaporation and the residue was purified by preparative HPLC to give 24 mg (81%) of the pure product.

MS (ESP, m/e): 704 (M$^+$, 100%), 726 ([M+Na]$^+$, 34%).

EXAMPLE 8

N,N'-Bis(2-hydroxypropionyl)-3,5-diamino-2,4,6-triiodobenzylalcohol a. N,N'-Bis(2-acetoxypropionyl)-3,5-diamino-2,4,6-triiodobenzylacetate 3,5-Diamino-2,4,6-triiodobenzylacetate (2.79 g, 5.0 mmol) was dissolved in dimethylacetamide (25 ml) and cooled to 0° C. 2-Acetoxypropionyl chloride (3.73 g, 25 mmol) was added dropwise and the mixture was stirred at room temperature for 17 h. The solvents were evaporated and the residue was triturated with diethyl ether. The solid residue was then purified by flash chromatography on silica gel using a mixture of $CH_2Cl_2$ and acetonitrile (5:1) as the eluent. Yield: 2.21 g (56%).

$^1$H NMR (DMSO-$d_6$): 10.20–10.23 (m, 2H) 5.52 (s, 2H), 5.21–5.24 (m, 2H), 2.06–2.13 (m, 9H), 1.51 (d, J=6.9 Hz, 6H).

b. N,N'-Bis(2-hydroxypropionyl)-3,5-diamino-2,4,6-triiodobenzylalcohol

N,N'-Bis(2-acetoxypropionyl)-3,5-diamino-2,4,6-triiodobenzylacetate (0.16 g, 0.2 mmol) was dissolved in a mixture of methanol (5 ml) and water (5 ml) and the pH was adjusted to 12 using a 1 M aqueous solution of NaOH. After stirring for 15 h, the solution was neutralized with 1 M HCl and the solvents were removed by evaporation. Purification by preparative HPLC gave 61 mg (46%) of the pure product.

MS (ESP, m/e): 660 (M$^+$, 5%), 682 ([M+Na]$^+$, 100%), 698 ([M+K]$^+$, 17%).

EXAMPLE 9

N,N'-Bis(2-hydroxypropionyl)-N-(2-hydroxyethyl)-3,5-diamino-2,4,6-triiodobenzylalcohol a. N,N'-Bis(2-acetoxypropionyl)-N-(2-acetoxyethyl)-3,5-diamino-2,4,6-triiodobenzylacetate N,N'-Bis(-acetoxypropionyl)-3,5-diamino-2,4,6-triiodobenzylacetate (393 mg, 0.50 mmol) was dissolved in a mixture of dimethylacetamide (4 ml) and DMSO (4 ml) containing 2-bromoethyl acetate (0.083 g, 0.50 mmol) and Cs₂CO₃ (244 mg, 0.75 mmol). The mixture was stirred for 17 h, water (20 ml) was added and the mixture was extracted with ether (3×25 ml). The combined organic phases were washed with water (3×20 ml), dried (MgSO₄) and evaporated. The residue was purified by preparative HPLC to give 80 mg (18%) of pure product.

$^1$H NMR (CD₃OD): 5.72–5.82 (m, 2H), 5.20–5.42 (m, 2H), 3.55–4.48 (m, 4H), 1.90–2.24 (m, 12H), 1.66 (d, J=7.1 Hz, 6H).

MS (ESP, m/e): 1004 ([M+Cs]⁺, 100%).

b. N,N'-Bis(2-hydroxypropionyl)-N-(2-hydroxyethyl)-3,5-diamino-2,4,6-triiodobenzylalcohol N,N'-Bis(2-acetoxypropionyl)-N-(2-acetoxyethyl)-3,5-diamino-2,4,6-triiodobenzylacetate (120 mg, 0.14 mmol) was dissolved in a mixture of water (7 ml) and methanol (7 ml) and pH was adjusted to 12 using an 1 M aqueous solution of NaOH. The mixture was stirred for 2 h, pH was adjusted to 7 with aqueous HCl and the solvents were evaporated. The product was purified by preparative HPLC. Yield: 70 mg (72%).

$^1$H NMR (CD₃OD): 5.27–5.34 (m, 2H), 4.31–4.41 (m, 1H), 3.82–4.12 (m, 4H), 3.55–3.73 (m, 1H), 1.51–1.60 (m, 3H), 1.23–1.32 (m, 3H).

MS (ESP, m/e): 726 ([M+Na]⁺, 100%).

EXAMPLE 10

N,N'-Bis(2-hydroxypropionyl)-N,N'-bis(2-hydroxyethyl)-3,5-diamino-2,4,6-triiodobenzylalcohol a. N,N'-Bis(2-acetoxypropionyl)-N,N'-bis(2-acetoxyethyl)-3,5-diamino-2,4,6-triiodobenzylacetate N,N'-Bis(2-acetoxypropionyl)-3,5-diamino-2,4,6-triiodobenzylacetate (197 mg, 0.25 mmol) was dissolved in a mixture of dimethylacetamide (5 ml) and DMSO (1.5 ml) containing 2-bromoethyl acetate (0.11 ml, 1.0 mmol) and Cs₂CO₃ (162 mg, 0.50 mmol). The mixture was stirred for 67 h, water (20 ml) was added and the mixture was extracted with ether (2×75 ml). The combined organic phases were washed with water (5×75 ml), dried (Na₂SO₄) and evaporated. The residue was purified by preparative HPLC to give 35 mg (15%) of pure product.

$^1$H NMR (DMSO-d₆) 5.49–5.73 (m, 2H), 4.97–5.22 (m, 2H), 3.49–4.00 (m, 6H), 1.86–12.08 (m, 15H), 1.09–1.58 (m, 6H).

b. N,N'-Bis(2-hydroxypropionyl)-N,N'-bis(2-hydroxyethyl)-3,5-diamino-2,4,6-triiodobenzylalcohol N,N'-Bis(2-acetoxypropionyl)-N,N'-bis(2-acetoxyethyl)-3,5-diamino-2,4,6-triiodobenzylacetate (175 mg, 0.18 mmol) was dissolved in a mixture of methanol (8 ml) and water (8 ml) and pH was adjusted to 12 with 1 M aqueous NaOH. After stirring for 3 h, the solution was neutralized with aqueous HCl. Purification by preparative HPLC gave 50 mg (37%) of the pure product.

$^1$H NMR (CD₃OD): 5.26–5.38 (m, 2H), 3.44–4.08 (m, 6H), 1.32–1.59 (m, 6H).

MS (ESP, m/e): 770 ([M+Na]⁺, 100%).

EXAMPLE 11

N,N'-Bis(2-hydroxypropionyl)-N-(2,3-dihydroxypropyl)-3,5-diamino-2,4,6-triiodobenzylalcohol a. N,N'-Bis(acetoxypropionyl)-N-[(2,2-dimethyl-1,3-dioxolane-4-yl)-methyl]-3,5-diamino-2,4,6-triiodobenzylacetate N,N'-Bis(2-acetoxypropionyl)-3,5-diamino-2,4,6-triiodobenzylacetate (393 mg, 0.50 mmol) was dissolved in a mixture of DMSO (4 ml) and dimethylacetamide (4 ml) containing Cs₂CO₃ (1.80 g, 5.52 mmol) and 4-bromomethyl-2,2-dimethyl-1,3-dioxolane (1.0 ml). The mixture was stirred for 7 days and was then worked up analogous to Example 7a. Purification by preparative HPLC gave 115 mg (26%) of the pure product.

$^1$H NMR (CD₃OD): 5.61–5.5.75 (m, 2H), 5.03–5.44 (m, 2H) 3.47–4.55 (m, 6H), 1.98–2.23 (m, 9H), 1.30–1.71 (m, 12H).

MS (ESP, m/e): 922 ([M+Na]⁺, 100%).

b. N,N'-Bis(2-hydroxypropionyl)-N-(2,3-dihydroxypropyl)-3,5-diamino-2,4,6-triiodobenzylalcohol N,N'-Bis(acetoxypropionyl)-N-[(2,2-dimethyl-1,3-dioxolane-4-yl)-methyl]-3,5-diamino-2,4,6-triiodobenzylacetate (115 mg, 0.13 mmol) was dissolved in a mixture of methanol (8 ml) and water (8 ml) and pH was adjusted to 12 with aqueous 1 M NaOH. After 2.5 h, pH was adjusted to 1 with 2 M aqueous HCl. After stirring for 17 h, the solution was neutralized with an aqueous NaH₂PO₄ buffer and the solvents were removed evaporation. Purification by preparative HPLC gave 65 mg (69%) of the pure product.

MS (ESP, m/e): 756 ([M+Na]⁺, 100%).

EXAMPLE 12

N,N'-Bis(2,3-dihydroxypropionyl)-3,5-diamino-2,4,6-triiodobenzylalcohol a. N,N'-Bis(2,2-dimethyl-1,3-dioxolane-4-carbonyl)-3,5-diamino-2,4,6-triiodobenzylacetate 3,5-Diamino-2,4,6-triiodobenzylacetate (3.54 g, 6.3 mmol) and 2,2-dimethyl-1,3-dioxolane-4-carboxylic acid chloride (3.13 g, 19 mmol) were dissolved in dimethylacetamide (40 ml) and the solution was stirred for 3.5 h. The solvent was removed by evaporation and the residue was treated with an aqueous solution of NaHCO₃. The crystalline residue was filtered off, washed with water and dried. Purification by flash chromatography using a mixture of CH₂Cl₂ and CH₃CN (3:1) as the eluent gave 1.90 g (37%) of the pure product. $^1$H NMR (DMSO-d₆): 9.93–10.02 (m, 2H), 5.30 (s, 2H), 4.58 (t, J=6.2 Hz, 1H), 4.29 (t, J=7.3 Hz, 1H), 4.10 (t, J=6.1 Hz, 1H), 2.06 (s, 3H), 1.54 (s, 3H), 1.38 (s, 3H).

MS (ESP, m/e): 902 ([M+dimethylacetamide]⁺, 100%).

b. N,N'-Bis(2,3-dihydroxypropionyl)-3,5-diamino-2,4,6-triiodobenzylalcohol

N,N'-Bis(2,2-dimethyl-1,3-dioxolane-4-carbonyl)-3,5-diamino-2,4,6-triiodobenzylacetate (1.25 g, 1.55 mol) was dissolved in a mixture of water (50 ml), methanol (25 ml) and concentrated HCl (0.5 ml). After stirring for 4 h, the solution was neutralized with aqueous NaH₂PO₄ and the solvents were removed by evaporation. The residue was dissolved in water (10 ml) and the pH was adjusted to 12 with aqueous NaOH. After 30 min, the solution was again neutralized and the solvent was evaporated. The product was purified by preparative HPLC. Yield: 483 mg (45%).

$^1$H NMR (9.65–9.83 (m, 2H), 5.77 (s, 2H), 5.20 (s, 1H), 4.95–5.03 (m, 2H), 4.81 (s, 2H), 4.00–4.08 (m, 2H), 3.72–3.82 (m, 2H), 3,50–3.63 (m, 2H)

MS (ESP, m/e): 692 (M⁺, 62%), 714 ([M+Na]⁺, 100%).

EXAMPLE 13

N,N'-Bis(2,3-dihydroxypropionyl)-N-(2-hydroxyethyl)-3,5-diamino-2,4,6-triiodobenzylalcohol N,N'-Bis(2,2-dimethyl-1,3-dioxolane-4-carbonyl)-3,5-diamino-2,4,6-triiodobenzylacetate (204 mg, 0.25 mmol) was dissolved in a mixture of dimethylacetamide (4 ml) and DMSO (2.5 ml) containing Cs₂CO₃ (650 mg, 2.0 mmol) and 2-bromoethyl acetate (0.035 ml, 0.31 mmol). After stirring for 1 week, ether (150 ml) and a NaH₂PO₄ buffer (100 ml)

were added, the organic phase was separated and the aqueous phase was extracted with ether (150 ml). The combined organic phases were then washed with water (6×100 ml), dried ($Na_2SO_4$) and evaporated. The residue was dissolved in a mixture of methanol (20 ml) and water (20 ml) and pH was adjusted to 12 with aqueous NaOH. After stirring for 1 h, the pH was adjusted to 1.5 with concentrated HCl and stirred for another 16 h. The solution was neutralized with aqueous $NaH_2PO_4$ and the solvents were evaporated. Preparative HPLC gave 55 mg (30%) of the pure product.

MS (ESP, m/e): 736 ($M^+$, 28%), 758 ($[M+Na]^+$, 100%).

EXAMPLE 14

N,N'-Bis(2,3-dihydroxypropionyl)-N,N-bis(2-hydroxyethyl)-3,5-diamino-2,4,6-triiodobenzylalcohol N,N'-Bis(2,2-dimethyl-1,3-dioxolane-4-carbonyl)-3,5-diamino-2,4,6-triiodobenzylacetate (204 mg, 0.25 mmol) was dissolved in a mixture of dimethylacetamide (5 ml) and DMSO (1.5 ml) containing $K_2CO_3$ (276 mg, 2.0 mmol) and 2-bromoethyl acetate (0.44 ml, 4.0 mmol). After stirring for 48 h, an aqueous $NaH_2PO_4$ buffer was added and the mixture was extracted with ether (2×150 ml). The combined organic phases were washed with water (6×100 ml), dried ($Na_2SO_4$) and evaporated. The solid residue was dissolved in a mixture of methanol (12 ml) and water (12 ml) and the pH was adjusted to 12 with aqueous NaOH. After stirring for 18 h, the solution was acidified with concentrated HCl (0.70 ml) and stirring was continued for 3 h. The solution was neutralized and the solvents were removed by evaporation. The product was purified by preparative HPLC. Yield: 98 mg (50%).

MS (ESP, m/e): 802 ($[M+Na]^+$n 100%).

EXAMPLE 15

N,N'-Bis(2,3-dihydroxypropionyl)-N-(2,3-dihydroxypropyl)-3,5-diamino-2,4,6-triiodobenzylalcohol N,N'-Bis(2,2-dimethyl-1,3-dioxolane-4-carbonyl)-3,5-diamino-2,4,6-triiodobenzylacetate (408 mg, 0.50 mmol) was dissolved in a mixture of dimethylacetamide (4 ml) and DMSO (4 ml) containing $Cs_2CO_3$ (1.80 g, 5.52 mmol) and 2,2-dimethyl-1,3-dioxolane-4-carboxylic acid chloride (2.0 ml). After stirring for 8 days, aqueous $NaH_2PO_4$ (100 ml) was added and the mixture was extracted with diethyl ether (2×150 ml). The combined organic phases were washed with water (6×100 ml), dried ($Na_2SO_4$) and evaporated. The residue was dissolved in a mixture of methanol (10 ml) and water (10 ml) and pH was adjusted to 12 with aqueous NaOH. After stirring for 2 h, concentrated HCl (1.0 ml) was added and stirring was continued for 16 h. After neutralization, the solvents were evaporated and the residue was purified by preparative HPLC. Yield: 149 mg (39%).

MS (ESP, m/e): 766 ($M^+$, 60%), 788 ($[M+Na]^+$, 100%).

EXAMPLE 16

Oxalic bis[3-hydroxymethyl-5-(2,3-dihydroxypropylaminocarbonyl)-2,4,6-triiodobenzeneamide]

a. 3-Acetoxymethyl-5-(2,3-diacetoxypropyl-aminocarbonyl)-2,4,6-triiodoaniline

3-Hydroxymethyl-5-(2,3-dihydroxypropyl-aminocarbonyl)-2,4,6-triiodoaniline (1.89 g, 3.06 mmol) prepared according to Example 3d, was dissolved in a mixture of acetic anhydride (5 ml) and pyridine (5 ml). The mixture was stirred at room temperature for 24 h, $CH_2Cl_2$ (100 ml) was added and the solution was washed with water (3×25 ml), with a saturated aqueous solution of $NaHCO_3$, dried ($Na_2SO_4$) and evaporated. The product was purified by flash chromatography on silica-gel using a mixture of $CH_2Cl_2$ and methanol (98:2) as the eluent.

Yield: 1.30 g (57%).

$^1$H NMR ($CDCl_3$): 6.10–6.25 (m, 1H), 5.48 (s, 2H), 5.20–5.28 (m, 1H), 4.22–4.43 (m, 2H), 3.53–3.89 (m, 2H), 2.06–2.13 (m, 9H).

MS (ESP, m/e): 744 ($M^+$, 100%).

b. Oxalic bis[3-hydroxymethyl-5-(2,3-dihydroxypropylaminocarbonyl)-2,4,6-triiodobenzeneamide]

3-Acetoxymethyl-5-(2,3-diacetoxypropylaminocarbonyl)-2,4,6-triiodoaniline (100 mg, 0.134 mmol) was dissolved in dioxane (1.0 ml) and the solution was heated to 90° C. Oxalyl chloride (0.096 mmol) was added and the mixture was stirred at 78° C. for 17 h. After cooling to room temperature, water (1.0 ml) was added and pH was adjusted to 12 with aqueous NaOH. After stirring for 4 h, the solution was neutralized, the solvents were evaporated and the residue was purified by preparative HPLC. Yield: 14 mg (16%).

$^1$H NMR ($CD_3OD$): 5.24 (s, 2H), 3.38–4.03 (m, 10H).

MS (ESP. m/e): 1290 ($M^+$, 33%), 1312 ($[M+Na]^+$, 100%).

EXAMPLE 17

Malonic bis[3-hydroxymethyl-5-(2,3-dihydroxypropylaminocarbonyl)-2,4,6-triiodobenzeneamide]

3-Acetoxymethyl-5-(2,3-diacetoxypropylaminocarbonyl)-2,4,6-triiodoaniline (100 mg, 0.134 mmol) prepared according to Example 16a, was dissolved in dioxane (1.0 ml) and malonyl chloride (0.097 mmol) was added. The mixture was stirred at 90° C. for 2 h and the solution was allowed to cool to room temperature. Water (1 ml) was added and pH was adjusted to 12 with aqueous NaOH. After stirring at 60° C. for 18 h, the solution was neutralized and the solvents were evaporated. The product was purified by preparative HPLC. Yield: 34 mg (39%).

MS (ESP, m/e): 1304 ($M^+$, 68%), 1326 ($[M+Na]^+$, 100%).

EXAMPLE 18

N,N'-diacetyl-N,N'-bis[3-hydroxymethyl-5-(2,3-dihydroxypropylaminocarbonyl)-2,4,6-triiodophenyl]-1,3-diamino-2-hydroxypropane N-acetyl-3-acetoxymethyl-5-(2,3-acetoxypropylaminocarbonyl)-2,4,6-triiodoaniline (300 mg, 0.38 mmol) prepared according to Example 3e was dissolved in a mixture of water (1.2 ml) and methanol (0.2 ml) and pH was adjusted to 12 with aqueous NaOH. Epichorohydrine (0.28 mmol) was added and the mixture was stirred at room temperature for 65 h. The solution was neutralized and the product was isolated by preparative HPLC. Yield: 60 mg (20%).

MS (ESP, m/e): 1398 ($[M+Na]^+$, 100%).

EXAMPLE 19

N-[3-hydroxymethyl-5-(2,3-dihydroxypropylaminocarbonyl)-2,4 6-triiodophenyl]-N'-[3,5-bis(2,3-dihydroxypropylaminocarbonyl)-2,4,6-triiodophenyl]urea a. N-[3-acetoxymethyl-5-(2,3-diacetoxypropyl-aminocarbonyl)-2,4,6-triiodophenyl]-N'[3,5-bis(2,3-diacetoxypropylaminocarbonyl)-2,4,6-triiodophenyl]urea 3,5-Bis(2,3-diacetoxypropylaminocarbonyl)-2,4,6-triiodoaniline (260 mg, 0.30 mmol) was dissolved in dioxane (1.0 ml) and a solution of phosgene in toluene (1.93 M, 1.8 ml) was added. The flask was tightly sealed and then heated to 60° C. for 17 h. After cooling to room temperature, the solvent was distilled off at reduced pressure. Dioxane (3 ml) was added and distilled off again. This procedure was repeated twice. Dioxane (1 ml) was added followed by 3-acetoxymethyl-5-(2,3-diacetoxypropylaminocarbonyl)-2,4,6-triiodoaniline (0.245 g, 0.31 mmol), prepared according to Example 16a, and $Hg(OCOCF_3)_2$ (20 mg). The mixture was stirred for 16 h at room temperature, the solvent was evaporated and the residue was purified by preparative HPLC. Yield: 0.192 g (39%).

MS (ESP, m/e): 1643 ($M^+$, 100%), 1665 ($[M+Na]^+$, 34%).

b. N-[3-hydroxymethyl-5-(2,3-dihydroxypropyl-aminocarbonyl)-2,4,6-triiodophenyl]-N'[3,5-bis(2,3-dihydroxypropylaminocarbonyl)-2,4,6-triiodophenyl]urea The product from Example 19a was dissolved in a mixture of methanol (5 ml) and water (5 ml) and the pH was adjusted to 12 using a 2 M aqueous solution of NaOH. After stirring for 2 h, the pH was adjusted to 6.5 using aqueous HCl and the solvents were evaporated. The product was purified using preparative HPLC. Yield: 68 mg (44%).

MS (ESP, m/e): 1349 ($M^+$, 15%), 1372 ($[M+Na]^+$, 100%).

EXAMPLE 20

N-Hydroxyacetyl-3-(1,2-dihydroxyethyl)-5-(2,3-dihydroxypropylaminocarbonyl)-2,4,6-triiodoaniline a. 3-Nitro-5-(2-trimethylsilylvinyl)benzoic acid methyl ester A mixture of 3-iodo-5-nitrobenzoic acid methyl ester (307 mg, 1.0 mmol), $Pd(OAc)_2$ (67 mg, 0.30 mmol), triphenylphosphine (0.032 g, 0.60 mmol), $AgNO_3$ (170 mg, 1.0 mmol), triethylamine (0.167 ml, 1.2 mmol) and vinyltrimethylsilane (0.309 ml, 2.0 mmol) was dissolved in acetonitrile (10 ml) and the solution was heated to 60° C. in a closed vessel for 48 h. The precipitated salts were filtered off and the filtrate was evaporated. The residue was chromatographed on silica gel using a mixture of ethyl acetate and heptane (1:11) as the eluent. Yield: 210 mg (75%).

$^1$H NMR ($CDCl_3$): 8.70–8.73 (m, 1H), 8.36–8.47 (m, 2H), 6.93 (d, J=19.2 Hz, 1H), 6.75 (d, J=19.2 Hz, 1H), 3.99 (s, 3H), 0.20 (s, 9H)

MS (APci, m/e): 279 ($M^+$, 100%).

b. 3-Nitro-5-vinylbenzoic acid methyl ester

3-Nitro-5-(2-trimethylsilylvinyl)benzoic acid methyl ester (2.44 g, 8.71 mmol) was dissolved in acetonitrile (150 ml), the solution was heated to reflux temperature and HCl gas was bubbled through the solution until the starting material had disappeared according to HPLC analysis. The solution was allowed to cool and the solvent was removed by evaporation. The residue was >95% pure according to HPLC and was used without further purification. Yield: 2.02 g (89%).

$^1$H NMR ($CD_3CN$): 8.64 (s, 1H), 8.54 (s, 1H), 8.45 (s, 1H), 6.96 (dd, $J_1$=10.8 Hz, $J_2$=17.4 Hz, 1H), 6.11 (d, J=17.4 Hz, 1H), 5.59 (d, J=10.8 Hz, 1H), 4.00 (s, 3H).

c. 3-Nitro-5-(1,2-dihydroxyethyl)benzoic acid methyl ester

3-Nitro-5-vinylbenzoic acid methyl ester (2.02 g, 9.76 mmol) was dissolved in a mixture of acetone and water (200 ml, 9:1), and, after cooling to 0° C., $OsO_4$ (60 mg, 0.24 mmol) was added followed by N-methylmorpholine-N-oxide (2,34 g, 20.0 mmol). After stirring for 46 h at room temperature, an aqueous solution of $Na_2S_2O_5$ (3.7 g) in water (150 ml) was added and the solution was acidified with dilute aqueous HCl. The volume of the solution was reduced to 150 ml by evaporation and the residue was extracted with ethyl acetate (3×100 ml). The combined organic phases were evaporated and the residue was purified by column chromatography on silica gel using ethyl acetate as the eluent. Yield: 1.60 g (60%).

$^1$H NMR ($CD_3CN$): 8.62–8.66 (m, 1H), 8.44–8.48 (m, 1H) 8.36–8.40 (m, 1H), 4.88–4.94 (m, 1H), 3.98 (s, 3H), 3.60–3.79 (m, 4H).

d. 1-(2,3-Dihydroxypropylaminocarbonyl)-3-nitro-5-(1,2-dihydroxyethyl)benzene

3-Nitro-5-(1,2-dihydroxyethyl)benzoic acid methyl ester (0.40 g, 1.69 mmol) and 2,3-dihydroxypropylamine (0.17 g, 1.86 mmol) were dissolved in methanol (2 ml) and the solution was stirred at 75° C. for 1 h. The pressure was then reduced to 200 mm Hg and stirring was continued at 95° C. for 2 h. The crude reaction mixture was purified by preparative HPLC. Yield: 0.40 g (78%).

MS (ESP. m/e): 299 ($[M-1]^+$, 100%).

e. 3-(2,3-Dihydroxypropylaminocarbonyl)-5-(1,2-dihydroxyethyl)aniline 1-(2,3-Dihydroxypropylaminocarbonyl)-3-nitro-5-(1,2-dihydroxyethyl)benzene (0.40 g, 1.32 mmol) was dissolved in a mixture of methanol (40 ml) and water (20 ml). The solution was hydrogenated at 60 psi using a Pd/C catalyst (10%, 50 mg). The solution was filtered through celite and the solvents were removed by evaporation. The product was >95% pure by HPLC analysis and was used without further purification.

MS (ESP, m/e): 271 ($[M+1]^+$, 100%), 293 ($[M+Na]^+$, 459).

f. 3-(2,3-Dihydroxypropylaminocarbonyl)-5-(1,2-dihydroxyethyl)-2,4,6-triodoaniline 3-(2,3-Dihydroxypropylaminocarbonyl)-5-(1,2-dihydroxyethyl)aniline (0.37 g, 1.35 mmol) was dissolved in a mixture of methanol (30 ml) and water (90 ml). $KICl_2$ (1.37 g, 4.05 mmol) was added and the solution was stirred at 35° C. for 24 h. Additional $KICl_2$ (1.0 mmol) was added, and stirring was continued at 60° C. for 72 h. An aqueous solution of $Na_2S_2O_5$ (1.0 g in 50 ml) was added and the solvents were removed by evaporation. Purification by preparative HPLC gave 87 mg (10%) of the pure product.

$^1$H NMR ($CD_3OD$): 8.60 (m, 1H), 5.38–5.47 (m, 1H), 3.96–4.26 (m, 3H), 3.30–3.84 (m, 10H).

MS (ESP, m/e): 648 ($M^+$, 15%), 670 ($[M+Na]^+$, 100%).

g. N-Hydroxyacetyl-3-(2,3-dihydroxypropylaminocarbonyl)-5-(1,2-dihydroxyethyl)-2,4,6-triodoaniline 3-(2,3-Dihydroxypropylaminocarbonyl)-5-(1,2-dihydroxyethyl)-2,4,6-triodoaniline (0.059 d, 0.091 mmol) was mixed with acetoxyacetyl chloride (1.0 ml) containing N,N-dimethylacetamide (0.4 ml) and the mixture was stirred at 60° C. for 48 h. The mixture was allowed to cool to room temperature, water was added and the solvents were removed by evaporation. The residue was dissolved in a mixture of methanol (10 ml) and water (5 ml) and an aqueous solution of NaOH (5 M, 1 ml) was added. The solution was stirred at room temperature for 1 h, the solution was neutralized with aqueous HCl and the solvents were evaporated. Purification by HPLC gave the pure product.

MS (ESP, m/e): 706 ($M^+$, 100%).

EXAMPLE 21

3,5-Di(hydroxyacetylamino)-2,4,6-triiodoactophenone a. 1,3-Diamino-5-(1-hydroxyethyl)benzene 3,5-Dinitroacetophenone (2.02 g, 9.5 mmol) which had been prepared according to the literature procedure (Y. Nagase et al., Macromol. Chem. Rapid Comm. (1990) 11, 185–191) was dissolved in methanol (100 ml) and hydrogenated at 60 psi using a Pd/C catalyst (5%, 100 mg). The catalyst was filtered off and the solvent was removed by evaporation. The product was used without purification in the next step. Yield: 1.22 g (84%).

¹H NMR (CDCl₃): 6.20 (d, J=2.0 Hz, 2H), 6.08 (t, J=2.0 Hz, 1H), 4.90 (br s, 4H), 4.62 (q, J=7.0 Hz, 1H), 3.37 (d, J=7.0 Hz, 3H).

MS (ESP, m/e): 151 ([M−1]⁺, 100%).

b. 1,3-Diamino-2,4,6-triiodoactophenone 1,3-Diamino-5-(1-hydroxyethyl)benzene (1.18 g, 7.72 mmol) was dissolved in a mixture of methanol and water (5:1, 168 ml) containing 1 M aqueous HCl (16 ml). An aqueous solution of KICl₂ (7.31 g, 30.9 mmol) was added quickly, and, after stirring for 50 min, the solid was filtered off, washed with water and dried. The product was pure by TLC and 1H NMR analysis. Yield: 3.62 g (89%).

¹H NMR CDCl₃): 4.86 (br s, 4H), 2.62 (s, 3H)

¹³C NMR (CDCl₃) 204.7, 151.1, 146.8, 28.7.

MS (APci, m/e): 528 (M⁺, 100%).

c. 1,3-Di(acetoxyacetylamino)-2,4,6-triiodoactophenone 1,3-Diamino-2,4,6-triiodoactophenone (1.8 g, 3.41 mmol) was dissolved in dimethylacetamide (15 ml) containing acetoxyacetyl chloride (1.1 ml, 10.2 mmol) and the solution was stirred for 65 h at room temperature. The solvents were removed by evaporation and the residue was purified by preparative HPLC. Yield: 1.69 g (68%).

¹H NMR DMSO-d₆): 10.13–10.27 (m, 2H), 4.65 (s, 4H), 2.56 (s, 3H), 2.12 (s, 6H).

MS (ESP, m/e): 750 ([M+Na]⁺, 100%), 766 ([M+K]⁺, 26%).

d. 1,3-Di(hydroxyacetylamino)-2,4,6-triiodoacetophenone 1,3-Di(acetoxyacetylamino)-2,4,6-triiodoacetophenone (0.171 g, 0.23 mmol) was dissolved in a mixture of methanol (30 ml) and water (5 ml) containing 2 M aqueous NaOH (3 ml). The solution was stirred for 90 min and was then neutralized using a strongly acidic cation exchange resin. The solvents were removed by evaporation and the residue was purified by preparative HPLC. Yield: 98 mg (54%).

MS (ESP, m/e): 644 (M⁺, 100%), 666 ([M+Na]⁺, 95%).

EXAMPLE 22

3,5-Di(hydroxyacetylamino)-1-hydroxyacetyl-2,4,6-triiodobenzene a. 3,5-Di(acetoxyacetylamino)-1-bromoacetyl-2,4,6-triiodobenzene 1,3-Di(acetoxyacetylamino)-2,4,6-triiodoacetophenone (0.20 g, 0.279 mmol) was dissolved in glacial acetic acid and bromine (0.044 g, 0.28 mmol) was added. The reaction was stirred at 2.5 h at 75° C. and then allowed to cool. The solvents were removed by evaporation and the residue was used directly in the next step.

MS (ESP, m/e): 806 (M⁺, 100%), 808 (M⁺, 98%).

b. 3,5-Di(acetoxyacetylamino)-1-acetoxyacetyl-2,4,6-triiodobenzene 3,5-Di(acetoxyacetylamino)-1-bromoacetyl-2,4,6-triiodobenzene (10 mg, 0.12 mmol) was converted into the corresponding acetate by heating to 110° C. in glacial acetic acid (5 ml) containing sodium acetate (1 mmol) and AgO-COCF₃ (0.11 g, 0.5 mmol) for 16 h. The product was purified by preparative HPLC. The yield was not determined.

MS (ESP, m/e): 786 (M⁺, 100%).

c. 3,5-Di(hydroxyacetylamino)-1-hydroxyacetyl-2,4,6-triiodobenzene

Hydrolysis of 3,5-di(acetoxyacetylamino)-1-acetoxyacetyl-2,4,6-triiodobenzene was carried out analogous to Example 4e. The crude product was purified by preparative HPLC. The yield was not determined.

MS (ESP, m/e): 687 ([M+HCOOH]⁺, 100%).

EXAMPLE 23

3,5-Di(hydroxyacetylamino)-1-(1,2-dihydroxyethyl)-2,4,6-triiodobenzene a. 3,5-Dinitrophenylethanol 3,5-Dinitroacetophenone (3.27 g, 0.0156 mol) was dissolved in a mixture of absolute ethanol (75 ml) and THF (37.5 ml) and the mixture was cooled to −10° C. NaBH₄ (0.30 g, 7.9 mmol) was added and the mixture was stirred for 1 h at −10° C. Water (80 ml) and ethyl acetate were added, the phases were separated and the organic phase was washed with water (80 ml) and dried (Na₂SO₄). The solvents were removed by evaporation and the residue was purified by chromatography on neutral alumina using a mixture of pentane and ethyl acetate (1:1) as the eluent. Yield: 2.52 g (76%).

¹H NMR (CDCl₃): 8.95 (t, J=2.0 Hz, 1H), 8.60 (d, J=2.0 Hz, 1H), 8.59 (d, J=2.0 Hz, 1H), 5.15 (q, J=7.5 Hz, 1H), 1.61 (d, J=7.5 Hz, 3H).

b. 3,5-Dinitrostyrene 3,5-Dinitrophenylethanol (1.0 g, 4.7 mmol) was mixed with P₂O₅ (1.0 g, 0.71 mmol) and the stirred mixture was heated to 100° C. After 3 h, the mixture was allowed to cool to room temperature and water (0.4 ml) was added. The pH was adjusted to 9 using 1 M aqueous NaOH and extracted with diethyl ether (2×25 ml). The combined organic phases were dried (Na₂SO₄) and evaporated. The crude product was used without further purification in the next step.

¹H NMR CDCl₃): 8.92 (t, J=2.0 Hz, 1H), 8.56 (d, J=2.0 Hz, 2H), 6.86 (dd, J₁=18.4 Hz, J₂=10.9 Hz, 1H), 6.08 (d, J=18.0 Hz, 1H), 5.67 (d, J=10.9 Hz, 1H).

c. 1-(1,2-Dihydroxyethyl)-3,5-dinitrobenzene 3,5-Dinitrostyrene (0.50 g, 2.58 mmol) was dissolved in a mixture of acetone and water (8:1, 70 ml) and the solution was cooled to 0° C. OsO₄ (0.046 g, 0.18 mmol) and NMO (0.60 g, 5.15 mmol) were added and the solution was stirred at room temperature for 16 h. A solution of Na₂S₂O₅ (1.5 g) in water (120 ml) was added and the organic solvent removed by evaporation. The aqueous phase was extracted with ethyl acetate (2×70 ml) and the combined organic phases were dried (Na₂SO₄) and evaporated. The product was purified by preparative HPLC. Yield: 0.44 g (75%).

¹H NMR (CD₃CN): 8.87 (t, J=2.0 Hz, 1H), 8.63 (t, J=2.0 Hz, 2H), 4.98 (t, J=6.0 Hz, 1H), 3.64–3.79 (m, 2H), 2,34 (s, 2H).

MS (ESP⁻, m/e): 227 (M⁻, 50%), 197 ([M-CH₂O]⁻, 100%).

d. 1-(1,2-Dihydroxyethyl)-3,5-diaminobenzene 1-(1,2-Dihydroxyethyl)-3,5-dinitrobenzene (0.10 g, 0.44 mmol) was dissolved in methanol (35 ml) and hydrogenation was carried out at 60 psi using a Pd/C catalyst 10%, 50 mg). The catalyst was filtered off and the solution was evaporated. Yield: 0.074 g (100%).

¹H NMR (CD₃OD): 6.14 (d, J=2.0 Hz, 2H), 6.06 (t, J=2.0 Hz, 1H), 4.98 (br s, 6H), 4.43–4.50 (m, 1H), 3.52–3.57 (m, 2H).

MS (ESP, m/e): 170 (M⁺, 100%), 210 ([M+K]⁺, 18%).

e. 1-(1,2-Dihydroxyethyl)-3,5-diamino-2,4,6-triiodobenzene 1-(1,2-Dihydroxyethyl)-3,5-diaminobenzene (0.0584 g, 0.242 mmol) was dissolved in a mixture of methanol (5 ml) and aqueous 2 M HCl (1.2 ml) and a solution of KICl₂ (70% in water, 0.97 mmol) was added in one portion. After stirring for 20 min at room temperature, a 10% aqueous NaHSO₃ solution (0.2 ml) was added, the solvents were removed by evaporation and the residue was purified by preparative HPLC. Yield: 31.4 mg (24%).

¹H NMR (CD₃OD): 5.56–5.63 (m, 1H), 4.03–4.12 (m, 1H), 3.79–3.87 (m, 1H), 5.06 (br s, 4H).

f. 1-(1,2-Dihydroxyethyl)-3,5-di(hydroxyacetylamino)-2,4,6-triiodobenzene 1-(1,2-Dihydroxyethyl)-3,5-diamino-2,4,6-triiodobenzene is acylated with acetoxyacetyl chloride using for example such a procedure as described in Example 4d. The crude product is then hydrolyzed analogous to Example 4e to give the final product. Purification of the crude product is carried out using preparative HPLC.

EXAMPLE 24

5-(Hydroxyacetamido)-3-hydroxymethyl-N-(2,3-dihydroxypropyl)-2,4,6-triiodobenzamide a. Methyl-5-nitro-3-hydroxymethyl)-benzoate 5-Nitro-monomethylphthalate (100 g, 0.44 mol) was dissolved in 2.5 l of dry tetrahydrofuran in a three-necked flask. Boron trifluoride diethyl etherate (126.0 g, 0.88 mol) was added with efficient stirring at room temperature and under inert atmosphere. Sodium borohydride (22.6 g, 0.60 mol) was added portionwise during 1 h. After stirring overnight, ethanol (100 ml) was added to the reaction mixture. Diethylether (2 l) and water (0.5 l) were then added and the phases separated. The organic phase was washed with a saturated solution of sodium hydrogen carbonate (1000 ml). The organic phase was dried ($Na_2SO_4$) and the solvent evaporated leaving 91.0 g (97%) of a light yellow crystalline residue.

$^1$H NMR (DMSO-$d_6$): 8.64 (d, 1H, J=2 Hz), 8.44 (d, 1H, J=2 Hz), 8.35 (t, 1H), 4.79 (s, 2H), 3.96 (s, 3H).

b. 5-Nitro-3-hydroxymethylbenzoic acid

Methyl-($^5$-nitro-3-hydroxymethyl)-benzoate (85.0 g, 0.40 mol) was dissolved in 15 ml of tetrahydrofuran by warming. After cooling to room temperature, a solution of sodium hydroxide (16.1 g, 0.40 mol) in water (150 ml) was slowly added with efficient stirring. After 30 minutes, the mixture was acidified to pH=2 with 6M hydrochloric acid. A white precepitate was formed, and after cooling in an ice-bath, the precipitate was filtered off and sucked dry on a filter. Yield after drying under vacuum was 79.2 g (100%).

$^1$H NMR (DMSO-$d_6$): 8.27–8.74 (m. 2H), 7.67–8.02 (m, 1H), 4.63 (d, 2H, J=3 Hz), 4.15 (br. s, 2H). $^{13}$C NMR (DMSO-$d_6$): 166.0, 148.3, 146.4, 145.2, 133.2, 132.7, 130.8, 124.9, 122,4, 119.4, 62,3, 61.9.

c. 5-Amino-3-hydroxymethylbenzoic acid

5-Nitro-3-hydroxymethyl benzoic acid (39.6 g, 0.20 mol) was suspended in a mixture of dioxane (25 ml) and water (50 ml). Palladium on carbon (5%) was added and the mixture was hydrogenated in a Parr apparatus until the stoichiometric amount of hydrogen had been consumed. The catalyst was filtered off and the filtrate passed into concentrated hydrochloric acid (12M, 17 ml). The filtrate was evaporated to dryness to give 40.6 g of a crystalline product. Yield is almost quantitative. The product was used without further purification.

MS (ESP, m/e): 166 ([M]$^+$, 100%).

d. 5-Amino-3-hydroxymethyl-2,4,6-triiodobenzoic acid

5-Amino-3-hydroxymethylbenzoic acid-hydrochloride salt (20.4 g, 0.10 mol) was dissolved in water (800 ml) and concentrated hydrochloric acid (40 ml) was added. A 70% w/w solution of potassium iododichloride (79.0 g, 0.23 mol) was added dropwise during 2 h at room temperature with efficient stirring. Another portion of $KICl_2$ solution (39.5 g, 0.12 mol) was then added quickly and the mixture was stirred at 50° C. for 12 h. After cooling, the brown precipitate was filtered off. The filtercake was dissolved in 340 ml of 2% solution of sodium hydroxide containing sodium hydrogen sulphite (1.0 g) and stirred for 15 min, at room temperature. The solution was then acidified to pH=2 with concentrated hydrochloric acid. The precipitate formed was filtered off and dried. The dried filtercake was triturated with a mixture of 95% methylene chloride and 5% methanol (2×100 ml). After drying 45.6 g (84%) of a white to grey powder was obtained $^1$H NMR (DMSO-$d_6$): 5.53 (s, 2H), 5. 48 (s, 1H), 5.10 (s, 2H), 3.92 (s, 1H).

MS (ESP, m/e): 544 ([M]$^+$, 100%).

e. 5-Amino-3-acetoxymethyl-2,4,6-triiodobenzoic acid

5-Amino-3-hydroxymethyl-2,4,6-triiodobenzoic acid (41.2 g, 0.076 mol) was dissolved in pyridine (100 ml), and acetic anhydride (80 ml) was added slowly with efficient stirring at room temperature. Stirring was continued overnight. The reaction mixture was then evaporated to a semisolid mass and treated with hydrochloric acid (2M, 250 ml). The white to grey precipitate formed was filtered off and washed with water (2×40 ml) and then dried. 44.2 g (100%) of product was isolated.

$^1$H NMR (DMSO-$d_6$): 5.43 (br. s, 2H), 5.35 (s, 2H), 3.45 (br. s, 1H), 2.03 (s, 3H).

$^{13}$C NMR (DMSO-$d_6$): 170.2, 170.0, 148.7, 148.6, 139.9, 88.2, 80.3, 79.5, 76.9, 20.4.

f. 5-Amino-3-acetoxymethyl-2,4,6-triiodobenzoyl chloride

5-Amino-3-acetoxymethyl-2,4,6-triiodobenzoic acid (43.9 g, 0.075 mol) was suspended in 1,2-dichloroethane (40 ml) and thionyl chloride (24.9 ml, 0.34 mol) was added. The mixture was heated to reflux temperature for 3 h. After evaporation to dryness, the residue was dissolved in tetrahydrofuran (50 ml). Sodium hydrogen carbonate (15 g) and crystalline sodium carbonate (5 g) were added to the solution and the mixture was stirred at room temperature for 3 h. The mixture was filtered and the filtrate evaporated to dryness. After pump-drying, a foam was formed, yield 44.6 g (98%). This material was used directly in the next step.

g. 5-Amino-3-acetoxymethyl-N-(2,3-dihydroxypropyl)-2,4,6-triiodobenzamide

5-Amino-3-acetoxymethyl-2,4,6-triiodobenzoyl chloride (12.0 g, 0.020 mol) was dissolved in 10 ml of dioxane and sodium carbonate (2.1 g, 0.020 mol) was added. To this solution was added a solution of 2,3-dihydroxypropylamine (1.8 g, 0.020 mol) dissolved in 15 ml of dioxane. The mixture was heated to reflux for 10 h. After cooling to room temperature, methanol (25 ml), strongly acidic ion exchange resin (Amberlyst 15, 50 g) and water (25 ml) were added to bring the pH to 3 to 4. After stirring at room temperature for 20 min, the resin was filtered off and the filtrate was evaporated to dryness. The semisolid dark crude product (12.6 g) was acetylated directly in the next step.

MS (ESP, m/e): 660 ([M]$^+$, 100%).

h. 5-Amino-3-acetoxymethyl-N-(2,3-diacetoxypropyl)-2,4,6-triiodobenzamide

5-Amino-3-acetoxymethyl-N-(2,3-dihydroxypropyl)-2,4,6-triiodobenzamide (2.13 g, 3.23 mmol) was dissolved in pyridine (12 ml). Acetic anhydride (10 ml) was added dropwise with efficient stirring. Stirring was continued at ambient temperature for 10 h. The reaction mixture was then evaporated to a solid residue, which was taken up in chloroform (70 ml). The organic phase was washed with aqueous hydrochloric acid (1M) until pH=2, then twice with water (40 ml) and last with a saturated solution of sodium hydrogen carbonate until pH=8–9. After drying ($Na_2SO_4$), the solvent was evaporated to yield a dark solid residue. This was taken up in a mixture of methylene chloride/ethyl acetate (90/10) and eluted through a pad of alumina. After evaporation of the solvent, 2.1 g (87%) of a white crystalline residue was left.

MS (ESP, m/e): 744 ([M]$^+$, 100%), 766 ([M+Na]$^+$, 20%).

¹H NMR (DMSO-d₆): 6.14 (t, 1H, J=,6 Hz), 5.49 (s, 2H), 5.22–5.31 (m, 1H), 5.12 (s, 2H), 4.37–4.45 (m, 1H), 4.21–4.32 (m, 1H), 3.73–3.93 (m, 1H), 3.48–3.68 (m, 1H), 2.21 (s, 3H), 2.10 (br. s, 6H).

i. 5-Acetoxyacetamido-3-acetoxymethyl-N-(2,3-diacetoxypropyl)-2,4,6-triiodobenzamide 5-Amino-3-acetoxymethyl-N-(2,3-diacetoxypropyl)-2,4,6-triiodobenzamide (3.0 g, 4.03 mmol) was dissolved in dry N,N-dimethylacetamide (8 ml) at ambient temperature. With efficient stirring acetoxyacetyl chloride (4.39 ml, 40.3 mmol) was added dropwise, and the mixture was stirred overnight. The mixture was then added slowly with stirring into a saturated solution of sodium hydrogen carbonate (80 ml). The precepitate formed was filtered off and dissolved in chloroform (80 ml). The organic solution was washed with an aqueous saturated solution of $NaHCO_3$ (25 ml), and then evaporated to dryness. The solid residue was dissolved in acetone and filtered through a pad of alumina with acetone as eluent. Evaporation of the solvent gave 3.38 g (100%) of a white crystalline product.

MS (ESP, m/e): 845 ([M]⁺, 100%), 784 ([M-OAc]⁺, 15%).

¹H NMR (DMSO-d6): 9.14 (br. s, 1H), 7.05–7.13 (m, 1H) 5.51 (s, 2H), 5.20–5.30 (m, 1H), 4.76 (s, 2H), 4.35–4.45 (m, 1H), 4.18–4.28 (d, 1H, J=7 Hz), 3.72–3.86 (m, 1H), 3.51–3.65 (m, 1H) 2.06 (s, 3H), 2.03 (s, 9H).

¹³C NMR (DMSO-d₆): 170.7, 170.6, 170.4, 170.3, 166.0, 150.1, 142.6, 106.8, 98.1, 97.3, 97.2, 70.0, 63.1, 63.0, 40.0, 21.5, 21.1, 20.5.

j. 5-Hydroxyacetamido-3-hydroxymethyl-N-(2,3-dihydroxypropyl)-2,4,6-triiodobenzamide 5-Acetoxyacetamido-3-acetoxymethyl-N-(2,3-diacetoxypropyl)- 2,4-6-triiodo-benzamide (1.0 g, 1.2 mmol) was dissolved in methanol (1 ml) at room temperature. A solution of sodium hydroxide (2 M, 3.5 ml) was slowly added with efficient stirring. After 30 minutes the reaction mixture was neutralized with a strong acidic ion exchange resin (Amberlyst 15). The resin was filtered off and the aqueous solution was evaporated to dryness. The residue was purified by preparative HPLC. Yield: 0.64 g (79%).

MS (ESP, m/e): 678 ([M]⁺, 100%).

¹H NMR (DMSO-d₆): 9.79 (s, 1H), 8.33, 8.50 (2 t, 1H, J=5 Hz), 5.66 (s, 1H), 5.19 (s, 1H), 4.96 (s, 2H), 4.68 (s, 1H), 4.48 (s, 1H), 4.01 (br. d, 2H, J=6 Hz), 3.65–3.77 (m, 1H), 3.40–3.58 (m, 2H), 3.08–3.30 (m, 2H).

¹³C NMR (DMSO-d₆): 170.5, 170.4, 170.2, 150.3, 146.0, 143.3, 143.1, 106.6, 98.7, 97.4, 97.3, 74.6, 70.0, 64.0, 61.9, 42.7.

EXAMPLE 25

5-[N'-(2-Hydroxyethyl)-hydroxyacetamido]-3-hydroxymethyl-N-(2,3-dihydroxypropyl)-2,4,6-triiodobenzamide a. 5-[N'-(2-Acetoxyethyl)-acetoxyacetamido]-3-acetoxymethyl-N-(2,3-diacetoxypropyl)-2,4,6-triiodobenzamide 5-Acetoxyamido-3-acetoxymethyl-N-(2,3-diacetoxypropyl)-2,4,6-triiodobenzamide (2.58 g, 3.05 mmol) was dissolved in dimethyl sulfoxide (5 ml) at room temperature. 2-Bromoethyl acetate (0.40 ml, 3.66 mmol) was added and the mixture cooled in an ice bath. Cesium carbonate (0.99 g, 3.05 mmol) was added portionwise. The mixture was stirred at room temperature for 5 h. The reaction mixture was added to aqueous hydrochloric acid (0.5 M, 50 ml). The precipitate formed and was filtered off, redissolved in methylene chloride (60 ml) and the solution washed with water (5×30 ml). The organic phase was dried ($Na_2SO_4$), and the solvent evaporated. A light yellow crystalline residue of 2.76 g (97%) was left.

MS (ESP, m/e): 932 ([M]⁺, 100%), 1061 ([M+Cs]⁺, 15%).

¹H NMR (CDCl₃): 6.26–6.52 (2m, 1H), 5.57 (br. s, 2H) 5.23–5.31 (m, 1H), 3.47–4.64 (m, 10H), 2.10 (br. s, 15H).

¹³C NMR (CDCl₃): 170.9, 170.8, 170.7, 166.3, 166.1, 151.6, 145.9, 144.2, 144.1, 108.0, 99.3, 99.0, 97.4, 70.1, 70.0, 63.8, 62.9, 62.8, 61.9, 61.0, 40.2, 28.6, 21.2, 21.0, 20.8, 20.7, 20.5.

b. 5-[N'-(2-Hydroxyethyl)-hydroxyacetamido]-3-hydroxymethyl-N-(2,3-dihydroxypropyl)-2,4,6-triiodobenzamide 5-[N'-(2-acetoxyethyl)-acetoxyacetamido]-3-acetoxymethyl-N-(2,3-diacetoxypropyl)-2,4,6-triiodobenzamide (2.76 g, 2.96 mmol) was dissolved in methanol (4 ml) at room temperature. An aqueous solution of sodium hydroxide (2M, 11.1 ml) was slowly added with efficient stirring. After 30 minutes, the pH of the solution was adjusted to 6 by the addition of a strongly acidic ion exchange resin (Amberlyst 15). The resin was filtered off and the solution was evaporated to a crystalline residue. The product was purified by preparative HPLC. Yield: 1.80 g (84%).

¹H NMR (DMSO-₆): 8.44–8.58 (m, 1H), 5.25 (br. s, 1H), 4.97 (s, 2H), 4.72 (br. s, 2H), 3.00–3.75 (m, 1H).

¹³C NMR (DMSO-d₆): 171.3, 170.9, 170.1, 170.0, 151.7, 147.4, 145.6, 107.4, 100.0, 99.3, 74.7, 70.1, 69.9, 64.0, 63.9, 61.7, 61.5, 58.5, 58.3, 51.5, 51.3, 42.5.

EXAMPLE 26

5-[N'-(2,3-Dihydroxypropyl)-hydroxyacetamido]-3-hydroxymethyl-N-(2,3-dihydroxypropyl)-2,4,6-triiodobenzamide a. 5-[N'-(2,2-Dimethyl-1,3-dioxolane-4-methyl)-acetoxyacetamido]-3-acetoxymethyl-N-(2,3-diacetoxypropyl)-2,4,6-triiodobenzamide 5-Acetoxyacetamido-3-acetoxymethyl-N-(2,3-diacetoxypropyl)-2,4,6-triiodo-benzamide (0.97 g, 1.15 mmol) was dissolved in dimethyl sulfoxide (3.0 ml) and cesium carbonate (0.38 g, 1.15 mmol) was added at room temperature. 4-Bromomethyl-2,2-dimethyl-1,3-dioxolane (0.34 g, 1.74 mmol) was added and the mixture heated is to 55° C. with efficient stirring. After 48 h the reaction mixture was cooled and poured into water (60 ml). The precipitate formed was filtered off and dissolved in ethyl acetate (60 ml). The organic phase was washed with a saturated sodium chloride solution (7×45 ml). After drying ($Na_2SO_4$), the solvent was evaporated leaving a yellow foam of 1.0 g (91%).

MS (ESP, m/e): 958 ([M]⁺, 100%), 1089 ([M+Cs]⁺, 15%).

¹H NMR (CDCl₃): 6.10–6.30 (m, 1H), 5.59 (br. s, 2H), 5.17–5.36 (m, 1H), 4.02–4.60 (m, 9H), 3.28–3.94 (m, 2H), 2.08, 2.20 (2s, 12H), 1.44 (s, 3H), 1.35 (s, 3H).

b. 5-[N'-(2,3-Dihydroxypropyl)-hydroxyacetamido]-3-hydroxymethyl-N-(2,3-dihydroxypropyl)-2,4,6-triiodobenzamide 5-[N'-(2,2-dimethyl-1,3-dioxolane-4-methyl]-3-acetoxymethyl-N-(2,3-diacetoxypropyl)-2,4,6-triiodobenzamide (1.05 g, 1.10 mmol) was dissolved in methanol (10 ml), and potassium carbonate (0.30 g, 2.2 mmol) was added. The mixture was stirred at room temperature for 17 h, filtered and the filtrate was then acidified with hydrochloric acid (SM) to pH=1. This solution was then stirred at room temperature for 5 h, and then evaporated to dryness. The residue was purified by preparative HPLC giving 0.36 g (44%) of the product, as a white solid.

MS (ESP, m/e): 781 ([M]+, 100%).

$^1$H NMR (DMSO-d$_6$): 8.16, 7.83 (2t, 1H, J=6–8 Hz), 5.22 (t, 1H, J=6 Hz), 4.98 (s, 2H), 4.87 (br. s, 1H), 4.63, 476 (2s, 2H), 4.55, 4.47, 4.44 (3s, 3H), 3.64–4.4(m, 6H), 3.40–3.62 (m, 5H), 3.16–3.32 (m, 2H).

$^{13}$C NMR (DMSO-d$_6$): 172.6, 172.4, 172.0, 171.7, 169.9, 169.7, 151.9, 151.7, 147.4, 147.1, 147.0, 146.0, 107.6, 106.9, 100.0, 99.4, 98.7, 74.9, 74.6, 69.8, 68.8, 64.6, 64.4, 63.7, 63.5, 61.9, 61.7, 58.7, 54.0, 53.0, 52.2, 52.0.

EXAMPLE 27

5-(2-Hydroxypropionylamino)-3-hydroxymethyl-N-(2,3-dihydroxypropyl)-2,4,6-triiodobenzamide a. 5-(2-Acetoxypropionylamino)-3-acetoxymethyl-N-(2,3-diacetoxypropyl)-2,4,6-triiodobenzamide 5-Amino-3-acetoxymethyl-N-(2,3-diacetoxypropyl)-2,4,6-triiodobenzamide (3.20 g, 4.3 mmol) was dissolved in dry dimethylacetamide (4 ml). 2-Acetoxypropionyl chloride (2.17 ml, 17.2 mmol) was then added dropwise with efficient stirring. Stirring was continued over night. After work up according to the procedure in Example 24i, 3.66 g (100%) of product was isolated.

MS (ESP, m/e): 857([M]+, 100%).

$^1$H NMR (CDCl$_3$): 8.53–8.59 (s, 1H), 6.56–6.59 (m, 1H) 5.54 (br. s, 2H), 5.42 (q, 1H, J=6 Hz), 5.20–5.31 (m, 1H), 4.35–4.45 (m, 1H), 4.18–4.30 (m, 1H), 3.73–3.80 (m, 1H), 3.53–3.68 (m, 1H), 2.08 (s, 3H), 2.06 (s, 9H), 1.63 (d, 3H, J=6 Hz).

$^{13}$C NMR (CDCl$_3$): 170.7, 170.6, 170.3, 170.1, 169.5, 168.7, 150.1, 142.8, 106.6, 97.4, 70.6, 70.5, 70.0, 63.0, 40.0, 21.5, 21.2, 20.8, 20.6, 17.7.

b. 5-(2-Hydroxypropionylamino)-3-hydroxymethyl-N-(2,3-dihydroxypropyl)-2,4,6-triiodobenzamide 5-(2-Acetoxypropionylamino)-3-acetoxymethyl-N-(2,3-diacetoxypropyl)-2,4,6-triiodo benzamide was hydrolysed according to the procedure described in Example 24j. The product was purified by preparative HPLC and isolated in 44% yield.

MS (ESP, m/e): 692 ([M]+, 100%).

$^1$H NMR (DMSO-$_6$): 9.96, 9.73 (2s, 1H), 8.34–8.51 (m, 1H), 5.58–5.67 (m, 1H), 5.18 (q, 1H, J=5 Hz), 4.96 (br. s, 2H), 4.69 (t, 1H, J=5 Hz), 4.48 (q, 1H, J=6 Hz), 4.09–4.20 (m, 1H), 3.64–3.76 (m, 1H), 3.35–3.53 (m, 2H), 3.06–3.33 (m, 2H), 1.38 (d, 3H, J=7 Hz).

$^{13}$C NMR (DMSO-d$_6$): 173.1, 173.0, 170.6, 150.7, 146.4, 144.0, 143.7, 143.5, 107.2, 107.1, 99.1, 99.0, 97.8, 97.7, 75.0, 70.4, 70.3, 68.0, 64.4, 43.1, 21.5.

EXAMPLE 28

5-[N'-(2-Hydroxyethyl)-2-hydroxypropionylamino]-3-hydroxymethyl-N-(2,3-dihydroxypropyl)-2,4,6-triiodobenzamide a. 5-[N'-(2-Acetoxyethyl)-2-acetoxypropionylamino]-3-acetoxymethyl-N-(2,3-di-acetoxypropyl)-2,4,6-triiodobenzamide 5-(2-Acetoxypropionylamino)-3-acetoxymethyl-N-(2,3-diacetoxypropyl)-2,4,6-triiodobenzamide was alkylated with 2-bromoethyl acetate according to the general procedure described in Example 25a. After work up the product was isolated in 95% yield.

MS (ESP, m/e): 943 ([M]+, 100%), 1073 ([M+Cs]+, 20%).

$^1$H NMR (CDCl$_3$): 6.27–6.56 (m, 1H), 4.98–5.60 (m, 4H) 3.46–4.44 (m, 8H), 2.16 (s, 3H), 2.09 (s, 12H), 1.33–1.43 (m, 3H).

$^{13}$C NMR (CDCl$_3$): 170.8, 170.7, 170.6, 170.5, 151.5, 147.3, 143.9, 143.7, 108.2, 108.1, 100.2, 98.6, 98.5, 97.7, 97.4, 70.1, 70.0, 69.9, 68.3, 65.9, 63.8, 63.0, 62.9, 61.8, 61.7, 49.6, 48.5, 40.1, 40.0, 30.9, 28.6, 21.1, 21.0, 20.8, 20.7, 20.6, 18.6, 17.1.

b. 5-[N'-(2-Hydroxyethyl)-2-hydroxypropionylamino]-3-hydroxymethyl-N-(2,3-dihydroxypropyl)-2,4,6-triiodobenzamide 5-[N'-(2-Acetoxyethyl)-2-acetoxypropionylamino]-3-acetoxymethyl-N-(2,3-diacetoxypropyl)-2,4,6-triiodobenzamide was hydrolysed according to the general procedure in Example 24j. The product was isolated in 47W yield, after purification by HPLC.

MS (ESP, m/e): 734 ([M]+, 100%).

$^1$H NMR (DMSO-d$_6$): 8.42–8.61 (m, 1H), 5.14–5.30 (m, 1H), 5.00 (br. s, 2H), 4.73–4.92 (m, 3H), 4.44–4.64 (m, 1H), 2.98–3.78 (m, 10H), 1.07–1.14, 1.33–1.37 (2m, 3H).

$^{13}$C NMR (DMSO-d$_6$): 174.4, 174.0, 170.6, 152.0, 147.6, 147.5, 147.2, 147.0, 109.2, 108.1, 101.5, 101.4, 99.2, 75.4, 75.1, 70.5, 70.3, 65.5, 65.4, 65.3, 65.0, 64.9, 64.4, 58.8, 58.6, 52.4, 52.1, 43.1, 42.9, 22.0, 21.7, 21.1.

EXAMPLE 29

5-(2,3-Dihyroxypropionylamino)-3-hydroxymethyl-N-(2,3-dihydroxypropyl)-2,4,6-triiodobenzamide a. 5-(2,2-Dimethyl-1,3-dioxolane-4-carbamido)-3-acetoxymethyl-N-(2,3-diacetoxypropyl)-2,4,6-triiodobenzamide Potassium 2,2-dimethyl-1,3-dioxolane-4-carboxylate (1.84 g, 10 mmol) was suspended in 35 ml of dry ether. Oxalyl chloride (0.87 ml,10 mmol) was added very slowly with efficient stirring at 0° C. under inert atmosphere. After stirring at this temperature for 2 h, the temperature was allowed to reach room temperature and stirring was continued for 20 h. The precipitate formed was filtered off, and the filtrate evaporated to give an oil.

5-Amino-3-acetoxymethyl-N-(2,3-diacetoxypropyl)-2,4,6-triiodobenzamide was dissolved in dry dimethylacetamide (10 ml) and added dropwise to the oil above under an inert atmosphere. Stirring was continued at room temperature for 48 h. The reaction mixture was slowly added to 2% aqueous solution of sodium hydrogen carbonate (100 ml). A very light tan coloured precipitate was formed, filtered off, washed with water (25 ml) and dried. The isolated product (2.02 g, 70%) was used without further purification.

MS (ESP, m/e): 872 ([M]+, 100%).

$^1$H NMR (DMSO-d$_6$): 10.70, 9.92 (2 br s, 1H), 8.77–8.90 (m, 1H), 5.46 (s, 2H), 5.09 (t, 1H, J=6 Hz), 4.59 (m, 1H), 4.23–4.38 (m, 2H), 4.05–4.22 (m, 2H), 3.30–3.58 (m, 2H), 1.98–2.11 (2s, 9H), 1.56 (s, 3H), 1.38 (s, 3H).

$^{13}$C NMR (DMSO-d$_6$): 170.71 170.5, 170.4, 169.4, 169.3, 150.0, 143.8, 141.5, 111.1, 108.3, 101.0, 99.0, 98.8, 77.4, 75.3, 69.9, 63.5, 35.0, 21.8, 21.5, 21.0, 20.7.

b. 5-(2,3-Dihyroxypropionylamino)-3-hydroxymethyl-N-(2,3-dihydroxypropyl)-2,4,6-triiodobenzamide 5-(2,2-Dimethyl-1,3-dioxolane-4-carbamido)-3-acetoxymethyl-N-(2,3-diacetoxypropyl)-2,4,6-triiodobenzamide (0.80 g, 9.16 mmol) was dissolved in methanol (7 ml) and potassium carbonate (0.17 g, 12.3 mmol) was added. The mixture was stirred at room temperature for 17 h. The mixture was filtered and pH of the filtrate was adjusted to 1 using aqueous SM hydrochloric acid, and the mixture was stirred for further 5 h at room temperature. The reaction mixture was then evaporated to a solid residue, which was purified by preparative HPLC. Yield: 0.41 g (49%) of a white freeze dried product.

MS (ESP, m/e): 706 ([M]+, 100%).

$^1$H NMR (DMSO-d$_6$): 9.77 (s, 1H), 8.32–8.48 (m, 1H, J=5 Hz), 5.76–5.84 (m, 1H), 5.18 (br. s, 1H), 4.95 (br. g ,

2H), 4.83 (s, 1H), 4.70 (s, 1H), 4.46–4.53 (m, 1H), 4.03–4.11 (m, 1H), 3.46–3.83 (m, 5H,), 3.07–3.34 (m, 2H,).

$^{13}$C NMR (DMSO-d$_6$): 170.5, 170.4, 170.2, 150.3, 146.0, 143.3, 143.1, 98.7, 97.3, 97.2, 74.7, 73.8, 70.0, 64.2, 64.0, 42.7.

EXAMPLE 30

5-[N'-(2-Hydroxyethyl)-2,3-dihyroxypropionylamino]-3-hydroxymethyl-N-(2,3-dihydroxypropyl)-2,4,6-triiodobenzamide a. 5-[N'-(2-Acetoxyethyl)-2,2-dimethyl-1,3-dioxolane-4-carboxamido]-3-acetoxymethyl-N-(2,3-diacetoxypropyl)-2,4,6-triiodobenzamide 5-(2,2-Dimethyl-1,3-dioxolane-4-carboxamido)-3-acetoxymethyl-N-(2,3-diacetoxypropyl)-2,4,6-triiodobenzamide (0.44 a, 0.50 mmol) was dissolved in dimethylsulfoxide (3 ml) and cesmium carbonate (0.33 g, 1.0 mmol) was added. 2-Bromoethyl acetate (0.25 g, 2.5 mmol) was added dropwise. The mixture was stirred at 45° C. for 17 h then added slowly into water (50 ml). A precipitate was formed, filtered off and the filtercake was dissolved in chloroform (60 ml). The organic phase was washed with water (2×30 ml), then dried (Na$_2$SO$_4$) and evaporated to a solid product. Yield: 0.46 g (93%).

MS (ESP, m/e): 958 ([M]$^+$, 100%), 1090 ([M+Cs]$^+$, 20%).

$^1$H NMR (CDCl$_3$): 6.43, 6.25 (2 br. d, 1H, J=6 Hz), 5.59 (t, 1H, J=5 Hz), 5.23–5.32 (m,1H), 3.52–4.65 (m, 12H), 2.11 (s, 12H).

$^{13}$C NMR (CDCl$_3$): 170.8, 170.7, 149.6, 144.1, 140.1, 140.0, 139.6, 136.2, 128.5, 127.7, 103.0, 98.7, 98.6, 70.8, 70.1, 70.0, 63.8, 63.0, 62.9, 62.2, 61.7, 40.9, 30.9, 28.6, 20.8, 20.6.

b. 5-[N'-,2-Hydroxyethyl)-2,3-dihydroxypropionylamino]-3-hydroxymethyl-N-(2,3-dihydroxypropyl)-2,4,6-triiodobenzamide 5-[N'-(2-Acetoxyethyl)-2,2-dimethyl-1,3-dioxolane-4-carboxamido]-3-acetoxymethyl-N-(2,3-diacetoxypropyl)-2,4,6-triiodobenzamide (47 mg, 0.049 mmol) was dissolved in methanol (0.5 ml) and an aqueous solution of sodium hydroxide (2M, 0.25 ml) was added slowly followed by water (2 ml). After stirring at room temperature for 20 minutes, the reaction mixture was neutralized with a strongly acidic Son exchange resin. The resin was filtered off, and the filtrate acidified to pH=1 using hydrochloric acid (5M). After stirring at room temperature for 3.5 hours the reaction mixture was evaporated to dryness and the solid residue was purified by preparative HPLC giving 28 mg (76%) of product.

MS (ESP, m/e): 749 ([M]$^+$, 100%).

$^1$H NMR (DMSO-d6): 8.34–8.55 (m, 1H), 5.09–5.30 (m, 2H), 5.10 (br. d, 2H, J=6 Hz), 4.35–4.89 (m, 6H), 3.00–3.74 (m, 10H).

$^{13}$C NMR (DMSO-d$_6$) 171.9, 170.5, 151.9, 147.5, 147.1, 146.9, 109.1, 100.1, 99.4, 99.2, 96.0, 75.4, 75.2, 71.3, 70.5, 70.3, 70.2, 64.4, 64.2, 64.0, 63.7, 58.6, 52.1, 43.0.

EXAMPLE 31

5-(3-Hydroxy-2-hydroxymethylpropionylamino)-3-hydroxymethyl-N-(2,3-dihydroxypropyl)-2,4,6-triiodobenzamide a. 5-[5-(2,2-Dimethyl-dioxane-1,3-yl)-carboxamido]-3-acetoxymethyl-N-(2,3-diacetoxypropyl)-2,4,6-triiodobenzamide 5-(2,2-Dimethyl-dioxane-1,3-yl)-carboxylic acid (1.8 g, 11.2 mmol) was dissolved in dimethylformamide (17 ml) The solution was cooled to 0° C. and thionyl chloride (0.82 ml, 11.2 mmol) was added slowly with efficient stirring. Stirring was continued at 25° C. for 5 h. 5-Amino-3-acetoxymethyl-N-(2,3-diacetoxypropyl)-2,4,9-triiodobenzamide (1.19 g, 1.6 mmol) was then added in one portion and the mixture was stirred at 45° C. for 24 h. After cooling to room temperature the reaction mixture was added slowly into a 2% aqueous solution of sodium hydrogen carbonate (150 ml).

A precipitate was formed, filtered off and purified by preparative HPLC to give 0.64 g (48%) of a white crystalline product.

MS (ESP, m/e): 886 ([M]$^+$, 100%).

$^1$H NMR (CDCl$_3$) 8.19–8.30 (m, 1H), 7.28–7.32 (m, 1H) 5.52 (s, 2H), 5.18–5.26 (m, 1H), 4.33–4.41 (m, 1H), 4.17–4.24 (m, 1H), 3.96 (d, 3H, J=5 Hz), 3.67–3.82 (m, 3H), 3.41–3.60 (m, 1H), 2.68–2.76 (m, 1H), 2.04 (s,9H), 1.1,9 (s, 6H).

$^{13}$C NMR (CDCl$_3$): 171.0, 170.7, 170.6, 142.6, 142.4, 140.5, 140.1, 105.7, 97.8, 97.0, 96.9, 70.1, 63.2, 39.7, 21.0, 20.6, 20.4.

b. 5-(3-Hydroxy-2-hydroxymethyl-propionylamino)-3-hydroxymethyl-N-(2,3-dihydroxypropyl)-2,4,6-triiodobenzamide 5-[5-(2,2-Dimethyl-dioxane-1,3-yl)-carboxamido-3-acetoxymethyl-N-( 2,3-diacet-oxypropyl)-2,4,6-triiodobenzamide (0.19 g, 0.21 mmol) was dissolved in methanol (2 ml) and an aqueous solution of sodium hydroxide (2M, 2 ml) was added. After stirring at room temperature for 30 min, the mixture was neutralized with strong acidic ion-exchange resin. The resin was filtered off and pH was adjusted to 1 using aqueous hydrochloric acid (5M). After stirring for 5 h, the mixture was evaporated to a solid residue. Purification by preparative HPLC gave 80 mg (526) of a white product.

MS (ESP, m/e): 720 ([M]$^+$, 1006).

$^1$H NMR (DMSO-d$_6$): 9.92 (s, 1H), 8.38, 8.42 (2t, 1H, J=6 Hz), 5.17 (q, 1H, J=6 Hz), 4.96 (s, 2H), 4.68 (s, 1H), 4.62 (s, 1H), 4.49 (s, 1H), 3.61–3.92 (m, 5H), 3.45–3.56 (m, 2H), 3.02–3.27 (m, 2H), 2.70 (m, 1H).

$^{13}$C NMR (DMSO-d$_6$): 170.8, 170.6, 170.2, 150.4, 146.1, 143.4, 143.2, 106.7, 106.6, 98.7, 97.3, 74.7, 70.0, 69.9, 64.1, 64.0, 59.7, 51.3, 51.2, 42.7.

EXAMPLE 32

5-(3-Hydroxy-2-methyl-2-hydroxymethyl-propionylamino)-3-hydroxymethyl-N-(2,3-dihydroxypropyl)-2,4,6-triiodobenzamide a. 5-(3-Acetoxy-3-methyl-2-acetoxymethyl-propionylamino)-3-acetoxymethyl-N-(2,3-diacetoxypropyl)-2,4,6-triiodobenzamide 5-Amino-3-acetoxymethyl-N-(2,3-diacetoxypropyl)-2,4,6-triiodobenzamide (2.48 g, 3.30 mmol) was dissolved in dimethylacetamide (10 ml) and added dropwise to 2,2-diacetoxymethylpropionyl chloride (2.36 g, 10 mmol). Stirring was continued at 60° C. for 48 h. The reaction mixture was cooled and added to a 2% aqueous solution of sodium hydrogen carbonate (120 ml). A precipitate was formed and filtered off, redissolved in chloroform (140 ml) and the organic phase was washed with water (5×40 ml). After drying (Na$_2$SO$_4$), the solvent was evaporated leaving a gum (ca. 3 g). MS analysis showed the product to consist of two compounds:

5-(3-Acetoxy-3-methyl-2-acetoxymethylpropionylamino)-3-acetoxymethyl-N-(2,3-diacetoxypropyl)-2,4,6-triiodobenzamide with MS (ESP, m/e): 944 ([M]$^+$, 100%).

5-Acetamido-3-acetoxymethyl-N-(2,3-diacetoxypropyl)-2,4,6-triiodobenzamide with MS (ESP, m/e): 786 ([M]$^+$, 80%).

The product was used in the next step without further purification.

b. 5-(3-Hydroxy-3-methyl-2-hydroxymethyl-propionylamino)-3-hydroxymethyl-N-(2,3-dihydroxypropyl)-2,4,6-triiodobenzamide The product mixture from Example 32a, was dissolved in acetonitrile (10 ml). Aqueous sodium hydroxide (2M, 17 ml, 33 mmol) was added and the mixture stirred at room temperature for 1 h. The mixture was then neutralized with a strongly acidic ion exchange resin. The resin was filtered off and the filtrate was evaporated to dryness. A semisolid residue was left which was purified by preparative HPLC. Yield: 1.02 g (42%).

MS (ESP, m/e): 734 ([M]$^+$, 100%).

$^1$H NMR (DMSO-d6): 9.57 (s, 1H)., 8.32, 8.41 (2t, 1H, J=5 Hz), 5.17 (t, 1H, J=6 Hz), 4.96 (br. s, 2H), 4.82, 4.95 (2s, 2H), 4.68 (d, 1H, J=6 Hz), 4.47, 4.49 (2d, 1H, J=6 Hz), 3.58–3.78 (m, 5H), 3.42–3.51 (m, 2H), 3.06–3.20 (m, 2H), 1.17, 1.15 (2s, 3H).

$^{13}$C NMR (DMSO-d$_6$): 173.3, 173.2, 170.2, 150.4, 146.1, 143.2, 106.5, 106.3, 98.5, 97.2, 74.6, 70.0, 69.9, 64.1, 63.5, 48.5, 48.4, 42.7, 17.1.

The by-product 5-acetamino-3-hydroxymethyl-N-(2,3-dihydroxypropyl)-2,4,6-triiodobenzamide was isolated in a yield of 16%.

EXAMPLE 33

5-(3-Hydroxy-2,2-dihydroxymethyl-propionylamino)-3-hydroxymethyl-N-(2,3-dihydroxypropyl)-2,46-triiodobenzamide a. 5-(3-Acetoxy-2,2-diacetoxymethyl-propionylamino)-3-acetoxymethyl-N-(2,3-diacetoxypropyl)-2,4,6-triiodobenzamide 5-Amino-3-acetoxymethyl-N-(2,3-diacetoxypropyl)-2,4,6-triiodobenzamide (1.05 g, 1.43 mmol) was dissolved in dimethylacetamide (2 ml) and added to trisacetoxymethylacetyl chloride (2.17 g, 7.4 mmol). The mixture was stirred at 60° C. for 5 days, and after cooling the mixture was added to an aqueous solution of sodium hydrogen carbonate (60 ml,2%). The precipitate formed was filtered off and dissolved in chloroform (90 ml). The organic phase was washed with water (4×40 ml), dried (Na$_2$SO$_4$), and the solvent evaporated. A semisolid residue (1.16 g) was left, which according to MS analysis consisted of the two compounds: 5-(3-Acetoxy-2,2-diacetoxymethyl-propionylamino)-3-acetoxymethyl-N-(2,3-diacetoxypropyl)-2,4,6-triiodobenzamide with MS (ESP, m/e): 1002 ([M]$^+$, 100%) and 5-acetamido-3-acetoxymethyl-N-(2,3-diacetoxypropyl)-2,4,6-triiodobenzamide with
MS (ESP, m/e): 786 ([M]$^+$, 70%).

HPLC analysis showed two compounds in ratio 2:3. The product mixture was used without further purification.

b. 5-(3-Hydroxy-2,2-dihydroxymethyl-propionylamino)-3-hydroxymethyl-N-(2,3-dihydroxypropyl)-2,4,6-triiodobenzamide The product mixture in Example 33a was dissolved in acetonitrile (3 ml) and hydrolysed according to the procedure in Example 32b. After preparative HPLC and freeze drying 0.30 g (29.8%) of a white product was isolated.

MS (ESP, m/e): 750 ([M]$^+$, 100%).

$^1$H NMR (DMSO-d$_6$): 9.61 (s, 1H), 8.25–8.45 (m, 1H), 5.17 (s, 1H), 4.95 (s, 2H), 4.64, 4.88 (2s, 4H), 4.48 (s, 1H), 3.80 (s, 6H), 3.65–3.74 (m, 1H), 3.45–3.49 (m, 2H), 3.06–3.28 (m, 2H).

$^{13}$C NMR DMSO-d$_6$): 172.0, 170.1, 150.4, 146.1, 143.0, 142.7, 106.2, 106.1, 98.3, 97.2, 74.6, 69.9, 64.0, 60.9, 59.6, 53.2, 42.7, 42.6.

EXAMPLE 34

5-(Hydroxyacetamido)-3-hydroxymethyl-N-(1,3,4-trihydroxybut-2-yl)-2,4,6-triiodobenzamide a. 5-Amino-3-acetoxymethyl-N-(1,3,4-trihydroxybut-2-yl)-2,4,6-triiodobenzamide 5-Amino-3-acetoxymethyl-2,4,6-triiodobenzoyl chloride (12.0 g, 19.8 mmol) was dissolved in dioxane (40 ml). 6-Amino-2,2-dimethyl-1,3-dioxepane-5-ol (3.20 g, 19.8 mmol) and sodium carbonate (2.10 g, 19.8 mmol) were added and the mixture heated to reflux for 10 h. The reaction mixture was cooled, methanol (100 ml) and water (50 ml) were added and the solution was neutralized with a strongly acidic ion exchange resin. The resin was filtered off and a aqueous solution of hydrochloric acid (2M, 20 ml) was added. The mixture was stirred at 60–70° C. for 30 min, and then evaporated to dryness, which gave a semisolid residue (13.6 g) which was used without further purification in the next steps.

MS (ESP, m/e): 689 ([M]$^+$, 100%).

b. 5-Amino-3-acetoxymethyl-N-(1,3,4-triacetoxybut-2-yl)-2,4,6-triiodobenzamide

The crude product from Example 34a (13.6 g) was dissolved in pyridine (100 ml). Acetic anhydride (80 ml) was added dropwise, and stirring was continued at ambient temperature overnight. The reaction mixture was then evaporated to dryness. The dark residue was taken up in methylene chloride (250 ml) and the organic phase was washed with 1 M hydrochloric acid until pH=1–2 in the water phase. The organic phase was then washed with water (2×50 ml) and an aqueous saturated solution of sodium hydrogen carbonate. The organic phase was dried (Na$_2$SO$_4$) and the solvent evaporated. The residue was dissolved in a mixture of methylene chloride/ ethyl acetate (4/1) and applied to a column of alumina. Elution and evaporation of eluent gave a white crystalline product (11.2 g, 69%).

MS (ESP, m/e): 816 ([M]$^+$, 100%).

$^1$H NMR (CDCl$_3$): 6.02–6.09 (m, 1H), 5.51 (s, 2H), 5.47 (br. s, 2H), 4.68–4.76 (m, 1H), 4.20–4.45 (m, 4H), 2.81–2.85 (m, 1H), 2.11, 2.08 (2s, 12H).

$^{13}$C NMR (CDCl$_3$): 170.4, 169.9, 169.8, 148.3, 147.9, 147.8, 140.9, 88.0, 70.1, 69.6, 69.5, 63.0, 62.1, 62.0, 48.4, 35.8, 21.1, 20.9, 20.8, 20.6.

c. 5-(Acetoxyacetamido)-3-acetoxymethyl-N-(1,3,4-triacetoxybut-2-yl)-2,4,6-triiodobenzamide The general acylation procedure in Example 24i was applied to the product in Example 34b. The yield was 95%.

MS (ESP, m/e): 916 ([M]$^+$, 100%).

$^1$H NMR (CDCl$_3$): 8.55, 8.57 (2s, 1H), 6.40 (t, 1H, J=7 Hz), 5.55 (s, 2H), 5.43–5.46 (m, 1H), 4.78 (br. s, 2H), 4.64–4.75 (m, 1H), 4.20–4.44 (m, 4H), 2.26 (s, 3H), 2.06, 2.08, 2.09 (3s, 12H).

$^{13}$C NMR (CDCl$_3$): 170.4, 170.3, 170.2, 169.8, 169.7, 149.6, 143.2, 143.1, 143.0, 142.4, 142,3, 107.3, 97.8, 97.4, 69.5, 69.2, 63.1, 63.0, 62.0, 61.9, 61.8, 48.3, 48.2, 21.1, 20.9, 20.8, 20.6.

d. 5-(Hydroxyacetamido)-3-hydroxymethyl-N-(1,3,4-trihydroxybut-2-yl)-2,4,6-triiodobenzamide Following the procedure in Example 24j, 5-(acetoxyacetamido)-3-acetoxymethyl-N-(1,3,4-triacetoxybut-2-yl)-2,4,6-triiodobenzamide was converted into the product. Yield: 77%.

MS (ESP, m/e): 708 ([M]$^+$, 100%).

$^1$H NMR (DMSO-d$_6$): 9.78, 9.95 (2s, 1H), 7.67–7.83 (m, 1H), 4.95 (s, 2H), 3.85–4.15 (m, 4H), 3.47–3.75 (m, 4H), 3.40 (br. s, 5H).

$^{13}$C NMR (DMSO-d$_6$): 170.5, 170.4, 169.7, 150.2, 146.1, 146.0, 143.3, 143.0 106.7, 106.5, 99.1, 98.9, 98.4, 97.7, 97.6, 97.1, 74.7, 69.1, 63.6, 63.6, 61.9, 58.8, 52.5, 52.4, 52.3.

EXAMPLE 35

5-[N'-(2-Hydroxyethyl)-hydroxyacetamido]-3-hydroxymethyl-N-(1,3,4-trihydroxybut-2-yl)-2,4,6-triiodobenzamide a. 5-[N'-(2-Acetoxyethyl)-acetoxyacetamido]-3-acetoxymethyl-N-(1,3,4-triacetoxybut-2-yl)-2,4,6-triiodobenzamide 5-(Acetoxyacetamido)-3-acetoxymethyl-N-(1,3,4-triacetoxybut-2-yl)-2,4,6-triiodobenzamide was alkylated with 2-bromoethyl acetate according to the procedure in Example 25a. Yield of crude product =97%.

MS (ESP, m/e): 1004 ([M]$^+$, 100%).

$^1$H NMR (CDCl$_3$): 6.36–6.58 (m, 1H), 5.54 (br. s, 2H) 5.41–5.49 (m, 1H), 4.66 (br. s, 2H), 4.16–4.41 (m, 7H), 3.78–3.94 (m, 1H), 3.47 (t, 1H, J=6 Hz), 2.03, 2.10 (2s, 18H).

$^{13}$C NMR (CDCl$_3$): 170.5, 170. 4, 170.3, 170.1, 169.9, 166.2, 166.0, 151.2, 146.8, 146.1, 145.9, 144.2, 108.3, 108.1, 100.5, 99.9, 99.6, 99.3, 99.1, 98.8, 98.4, 69.6, 69.5, 63.8, 62.9, 62.8, 61.8, 60.9, 60.3, 48.9, 48.7, 48.5, 48.4, 47.6, 47.2, 28.7, 21.0, 20.8, 20.7, 20.5.

b. 5-[N'-(2-Hydroxyethyl)-hydroxyacetamido]-3-hydroxymethyl-N-(1,3,4-trihydroxybut-2-yl)-2,4,6-triiodobenzamide The product of Example 35a was hydrolysed according to the procedure in Example 25b. The yield after preparative HPLC was 46%.

MS (ESP, m/e): 751 ([M]$^+$, 100%).

$^1$H NMR (DMSO-d$_6$): 7.70–8.16 (m,1H), 5.00 (br. s, 2H) 3.44–4.92 (m, 18H).

$^{13}$C NMR (DMSO-d$_6$): 171.9, 171.8, 171.3, 170.3, 170.2, 170.1, 152,3, 152.1, 147.8, 147.7, 147.6, 146.0, 145.9, 107.8, 107.6, 107.5, 100.9, 100.8, 100.0, 99.3, 64.1, 64.0, 62.2, 61.9, 59.1, 58.9, 52.8, 52.5, 52.4, 51.9, 51.7.

EXAMPLE 36

5-[N'-(2,3-Dihydroxypropyl)-hydroxyacetamido]-3-hydroxymethyl-N-(1,3 4-trihydroxybut-2-yl)-2,4,6-triiodobenzamide a. 5-[N'-(2,2-Dimethyl-1,3-dioxolane-4-methyl)-acetoxyacetamido]-3-acetoxymethyl-N-(1,3,4-triacetoxybut-2-yl)-2,4,6-triiodobenzamide Acylation of 5-amino-3-acetoxymethyl-N-(1,3,4-triacetoxybut-2-yl)-2,4, 6-triiodobenzamide followed the procedure in Example 26a. Yield of crude product=97%.

MS (ESP, m/e): 1031 ([M]$^+$, 100%), 1163 ([M+Cs]$^+$, 21%).

1H NMR (CDCl$_3$): 6.10–6.30 (m, 1H), 5.58 (br. s, 2H), 5.44–5.58 (m, 1H), 4.67–4.80 (m, 1H), 3.19–4.56 (m, 10H), 2.08, 2.12 (2s, 15H), 1.20, 1.25, 1.28, 1.34, 1.40, 1.45 (6s, 6H).

$^{13}$C NMR (CDCl$_3$): 170.3, 170.2, 169.9, 169.0, 151.2, 146.9, 144.5, 144.4, 144.3, 109.8, 109.5, 99.3, 98.9, 98.8, 98.0, 97.9, 97.5, 75.2, 73.6, 69.6, 68.3, 66.3, 64.8, 62.8, 61.9, 32.7, 30.9, 26.9, 26.8, 25.4, 21.0, 20.9, 20.8, 20.6.

b. 5-[N'-2,3-Dihydroxypropyl)-hydroxyacetamido]-3-hydroxymethyl-N-(1,3,4-trihydroxybut-2-yl)-2,4,6-triiodobenzamide Hydrolysis of the compound of Example 36a followed the procedure in Example 26b. Yield: 44% after preparative HPLC.

MS (ESP, m/e): 780 ([M]$^+$, 100%).

$^1$H NMR (DMSO-d$_6$): 7.68–8.22 (m, 1H), 5.22 (t, 1H, J=6 Hz), 4.98 (s, 2H), 4.80–4.93 (s, 1H), 4.63, 4.76 (2s, 2H), 4.55, 4.46, 4.44 (3s, 3H), 3.64–4.04 (m, 6H), 3.40–3.62 (m, 5H), 3 3.16–3.32 (m, 2H).

$^{13}$C NMR (DMSO-d$_6$): 172.6, 172.4, 172.0, 171.7, 169.9, 169.7, 151.9, 151.7, 147.4, 147.1, 147.0, 146.0, 107.6, 106.9, 100.0, 99.4, 98.7, 74.9, 74.6, 69.8, 69.1, 69.0, 68.8., 64.6, 64.4, 63.7,–63.5, 61.9, 61.7, 58.7, 54.0, 53.0, 52.2, 52.0.

EXAMPLE 37

5-(2-Hydroxypropionylamino)-3-hydroxymethyl-N-(1,3,4-tri-hydroxybut-2-yl)-2,4,6-triiodobenzamide a. 5-(2-Acetoxypropionylamino)-3-acetoxymethyl-N-(1,3, 4-triacetoxybut-2-yl)-2,4,6-triiodobenzamide 5-Amino-3-acetoxymethyl-N-(1,3,4-triacetoxybut-2-yl)-2,4,6-triiodobenzamide was acylated according to the procedure of Example 27a. Yield of crude product=97%.

MS (ESP, m/e): 930 ([M]$^+$, 100%).

$^1$H NMR (CDCl$_3$): 8.49, 8.55 (2s, 1H), 6.49–6.61 (m, 1H), 5.38–5.59 (m,4H), 4.64–4.76 (m, 1H), 4.18–4.46 (m, 4H), 2.22 (s, 3H), 2.60 (s, 12H), 1.63 (d, 3H, J=7 Hz).

$^{13}$C NMR (CDCl$_3$): 170.6, 170.4, 170.3, 169.7, 169.6, 149.7, 143.0, 142.2, 107.0, 98.0, 97.9, 97.7, 97.6, 97.2, 70.6, 69.57 69.3, 63.0, 62.0, 61.9, 48.2, 21.5, 21.1, 20.9, 20.8, 20.6, 17.7, 17.6.

b. 5-(2-Hydroxypropionylamino)-3-hydroxymethyl-N-(1,3, 4-trihydroxybut-2-yl)-2,4,6-triiodobenzamide The product of Example 37a was hydrolysed according to the procedure of Example 24j. Yield (after preparative HPLC): 72%.

MS (ESP, m/e): 720 ([M]$^+$,100%).

$^1$H NMR (CDCl$_3$) 9.95, 9.72 (2s, 1H), 7.68–7.84 (m, 1H), 5.58–5.67 (m,2H), 5.12–5.21 (m, 2H), 5.00 (br. s, 2m, J=6 Hz), 4.66–4.73 (m, 1H, J=6 Hz), 4.40–4.58 (m, 2H), 4.10–4.21 (m, 1H), 3.85–3.96 (m, 2H), 3.65–3.77 (m, 1H), 3.46–3.58 (s, 1H), 1.38 (d, 3H).

$^{13}$C NMR (DMSO-d$_6$): 173.0, 170.1, 150.6, 146.4, 143.7, 143,5, 107.1, 99.5, 99.0, 98.7, 98.0, 97.4, 75.1, 69.5, 68.0, 64.0, 59.1, 52.8, 21.5.

EXAMPLE 38

5-(2,3-Dihydroxypropionylamino)-3-hydroxymethyl-N-(1,3,4-trihydroxybut-2-yl)-2,4,6-triiodobenzamide a. 5-(2,2-Dimethyl-1,3-dioxolane-4-carbamido)-3-acetoxymethyl-N-(1,3,4-triacetoxybut-2-yl)-2,4,6-triiodobenzamide 5-Amino-3-acetoxymethyl-N-(1,3,4-triacetoxybut-2-yl)-2,4,6-triiodobenzamide was acylated according to the procedure described in Example 29a. After work up the yield of crude product was 97%.

MS (ESP, m/e): 943 ([M]$^+$, 100%).

$^1$H NMR (CDCl$_3$): 8.28–8.35 (2s, 1H), 6.15–6.32 (m, 1H), 5.58 (br. 2H), 5.42–5.53 (m, 2H ,) 4.29–4.72 (m, 7H) 2.07, 2.13 (2s, 12H), 1.44, 1.51 (2s, 6H).

$^{13}$C NMR (CDCl$_3$): 170.7, 170.6, 170.4, 170.3, 169.8, 169.7, 159.2, 156.2, 152.8, 149.9, 143.2, 143.1, 142.1, 140.4, 139.6, 128.5, 111.9, 111.6, 98.6, 97.6, 97.5, 97.3, 97.1, 96.6, 95.2, 75.2, 73.9, 72.9, 67.2, 62.7, 60.4, 26.9, 26.8, 26.3, 25.7, 25.4, 20.9, 20.8, 14.2.

b. 5-(2,3,-Dihydroxypropionylamino)-3-hydroxymethyl-N-(1,3,4-trihydroxybut-2-yl)-2,4,6-triiodobenzamide The product of Example 38a was hydrolysed according to the procedure of Example 29b. After preparative HPLC the product was isolated in 52% yield.

MS (ESP, m/e): 736 ([M]$^+$, 100%).

$^1$H NMR (DMSO-d$_6$): 9.75, 9.78 (2s, 1H), 7.66–7.82 (m, 1H), 5.73–5.84 (m, 1H), 5.10–5.38 (m, 1H), 4.95 (br. s, 2H), 4.64–4.88 (m, 2H), 4.38–4.60 (m, 2H), 4.02–4.11 (m, 2H), 3.85–3.95 (m, 2H), 3.64–3.82 (m, 2H)), 3.47–3.62 (m, 3H).

¹³ NMR (DMSO-d₆): 170.8, 170.1, 150.6, 146.4, 143.7, 143.5, 99.5, 98.6, 98.0, 9 7.3, 75.1, 74.2, 69.4, 65.5, 64.6, 64.0, 59.1, 52.8.

EXAMPLE 39

5-[N'-(2-Hydroxyethyl)-2,3-dihydroxypropionylamino]-3-hydroxymethyl-N-(1,3,4-trihydroxybut-2-yl)-2,4,6- triiodobenzamide a. 5-[N-(2-Acetoxyethyl)-2,2-dimethyl-1,3-dioxolane-4-carboxamido]-3-acetoxymethyl-N-(1,3,4-triacetoxybut-2-yl)-2,4,6-triiodobenzamide The product of Example 38a was N-alkylated with 2-bromoethyl acetate according to the general procedure in Example 30a. Yield of isolated crude product was 94%.

MS (ESP, m/e): 1030 ([M]⁺, 100%), 1161 (M+Cs]⁺, 20%).

¹H NMR (CDCl₃) 6.10–6.53 (m, 12), 5.55, 5.59, 5.62 (3s, 2H), 5.43–5.53 (m, 1H ), 4.63–4.77 (m, 29), 3.50–4.43 (m, 10H), 1.92, 1.96, 2.0, 2.11 (4s, 15H), 1.24, 1.32, 1.46, 1.50 (4s, 6 2H).

¹³C NMR (DMSO-d₆): 170.5, 170.4, 170.2, 170.0, 169.1, 150.9, 150.8, 150.5, 147.2, 144.0, 143.8, 143.7, 143.5, 111.5, 111.4, 99.9, 99.6, 98.3, 97.9, 97.5, 74.0, 73.8, 69.7, 69.6, 69.5, 68.1, 67.9, 67.3, 66.1, 63.8, 63.0, 62.9, 62.8, 62.0, 61.9, 60.4, 49.3, 49.2, 48.5, 48.4, 48.3, 48.1, 48.0, 47.9, 30.9, 28.7, 26.0, 25.7, 21.0, 20.9, 20.8, 20.6, 14.2.

b. 5-[N'-(2-Hydroxyethyl)-2,3-dihydroxypropionylamino]-3-hydroxymethyl-N-(1,3,4-trihydroxybut-2-yl)-2,4,6-triiodobenzamide The product of Example 39a was hydrolysed according to the procedure of Example 30b. After purification by preparative HPLC the product was isolated in 40% yield. MS (ESP, m/e): 780 ([M]⁺, 100%).

¹H NMR (DMSO-d₆): 7.72–8.03 (m, 1H), 5.15–5.30 (m, 1H) 5.00 (s, 2H), 4.70–4.97 (m, 4H), 4.55–4.69 (m, 1H), 4.40–4.54 (m, 1H), 3.86–3.98 (m, 1H), 3.45–3.75 (m, 8H,), 3.15–3.34 (m, 4H)

¹³C NMR (DMSO-d₆): 172.0, 171.6, 171.3, 171.1, 170.0, 151.7, 151.5, 147.1, 147.0, 146.9, 146.7, 146.5, 146.4, 108.8, 108.6, 101.1, 100.7, 100.3, 99.9, 99.2, 99.1, 98.5, 98.3, 75.2, 75.0, 71.3, 71.0, 70.8, 69.1, 68.8, 68.6, 63.9, 63.7, 63.5, 63.3, 59.3, 58.7, 58.4, 58.2, 52.2, 52.5, 52.0, 51.8, 51.7, 51.5.

EXAMPLE 40

5-Hydroxyacetamido-3-hydroxymethyl-N,N-bis(2-hydroxyethyl) -2,4,6-triiodobenzamide a. 5-Amino-3-acetoxymethyl-N,N-bis(2-hydroxyethyl)-2,4,6-triiodobenzamide 5-Amino-3-acetoxymethyl-2,4,6-triiodobenzoyl chloride was reacted with diethanolamine according to the general procedure in Example 24 g. Yield of isolated crude product was 98%.

¹H NMR (DMSO-d₆): 5.36 (br. s; 2H) , 4.86 (br. s, 2H), 4.72 (s, 1H), 3.68 (t, 2H, J=7 Hz), 3.47–3.60 (m, 4H), 3.14 (t, 2H, J=6 Hz), 2.05 (s, 3H).

¹³C NMR (DMSO-d₆): 170.5, 170.1, 148.6, 147.8, 148.2, 147.8, 147.5, 145.1, 140.0, 88.0, 87.5, 82.4, 81.7, 81.6, 79.9, 76.9, 74.5, 66.4, 58.8, 57.7, 51.6, 48.0, 20.4.

b. 5-Amino-3-acetoxymethyl-N,N-bis(2-acetoxyethyl)-2,4,6-triiodobenzamide

The product in Example 40a was acetylated according to conditions in Example 24h.

After work up and purification the product was isolated in 97% yield.

MS (ESP, m/e): 758 ([M]⁺, 100%).

¹H NMR (CDCl₃): 5.50 (s, 2H), 5.13 (br. s, 2H), 4.45 (t, 2H, J=6 Hz), 4.25 (t, 2H, J=6 Hz), 3.85 (t, 2H J=6 Hz), 3.49 (t, 2H, J=6 Hz), 2.07, 2.09, 2.11 (38, 9H).

c. 5-Acetoxyacetamido-3-acetoxymethyl-N,N-bis(2-acetoxyethyl)-2,4,6-triiodo-benzamide After acylation of the product of Example 40b according to the method described in Example 24i, the product was isolated in 88% yield.

¹H NMR (CDCl₃): 9.08 (s, 1H) , 5.54 (s, 2H) , 4.79 (s, 2H), 4.40–4.48 (m, 2H,), 4.22 (t, 2H, J=6 Hz), 3.70–3.98 (m, 2H), 3.40–3.52 (m, 2H), 2.42 (s, 3H), 2.05, 2.07, 2.09 (3s, 9H).

¹³C NMR (CDCl₃): 171.2, 170.5, 170.4, 170.2, 169.7, 165.7, 148.1, 143.2, 142.9, 107.4, 98.2, 97.2, 63.1, 61.5, 61.3, 48.9, 4S.3, 21.0, 20.8, 20.6.

d. 5-Hydroxyacetamido-3-hydroxymethyl-N,N-bis(2-hydroxyethyl)-2,4,6-triiodobenzamide Hydrolysis of the product of Example 40c according to the procedure of Example 24j and preparative HPLC afforded the product in 69% yield.

MS (ESP, m/e): 690 [M]⁺, 100%.

¹H NMR (DMSO-d₆): 9.84, 9.79 (2s, 1H), 5.68 (br. s, 1H) 5.20 (br. s, 1H), 4.94 (s, 2H), 4.78 (br. s, 2H), 4.00 (s, 2H), 3.70 (t, 2H, J=6–7 Hz), 3.48–3.60 (m,4H), 3.14 (q, 2H, J=6 Hz).

¹³C NMR (DMSO-d₆): 170.6, 170.4, 170.3, 170.1, 166.4, 166.2, 150.3, 147.1, 146.8, 144.6, 144.5, 107.8, 107.6, 99.8, 99.6, 99.3, 99.1, 62.8, 62.5, 61.9, 61.5, 61.3, 61.2, 48.6, 48.3, 48.2, 45.2, 21.0, 20.9, 20.8, 20.6, 20.5.

EXAMPLE 41

5-[N'-(2-Hydroxyethyl)-hydroxyacetamido]-3-hydroxymethyl-N,N-bis(2-hydroxyethyl)-2,4,6-triiodobenzamide a. 5-[N'-(2-Acetoxyethyl)-acetoxyacetamido]-3-acetoxymethyl-N,N-bis(2-acetoxyethyl)-2,4,6-triiodobenzamide The compound of Example 40c was alkylated with 2-bromoethyl acetate according to the procedure of Example 25a. The crude product was isolated in 97% yield.

¹H NMR (CDCl₃): 5.56, 5.58 (2s, 2H), 4.30–4.48 (m, 8H) 3.80–3.95 (m, 4H), 3.42–3.53 (m, 2H), 1.97, 2.06, 2.14 (3s, 15H).

¹³C NMR (CDCl₃): 170.6, 170.4, 170.3, 170.1, 166.4, 166.2, 150.3, 147.1, 146.8, 144.6, 144.5, 107.8, 107.6, 99.8, 99.6, 99.3, 99.1, 62.8, 62.5, 61.9, 61.5, 61.3, 61.2, 48.6, 48.3, 48.2, 45.2, 21.0, 20.9, 20.8, 20.6, 20.5.

b. 5-[N'-(2-Hydroxyethyl)-hydroxyacetamido]-3-hydroxymethyl-N,N-bis(2-hydroxyethyl)-2,4,6-triiodobenzamide The product of Example 41a was hydrolysed according to procedure of Example 25b in a yield of 43%, after HPLC purification.

MS (ESP, m/e): 735 ([M]⁺, 100%).

¹H NMR (DMSO-d₆): 5.24 (t, 1H, J=5 Hz), 4.98 (t, 1H, J=6 Hz), 4.95 (d, 2H, J=4 Hz), 4.71–4.84 (m, 3H), 3.65–3.74 (m, 2H), 3.48–3.63 (m, 10H), 3.09–3.18 (m, 2H).

¹³C NMR (DMSO-d₆): 170.9, 170.8, 170.1, 149.8, 148.1, 148.0, 146.2, 107.9, 100.4, 100.3, 99.7, 99.6, 74.7, 61.5, 61.4, 59.0, 58.5, 57.6, 51.7, 51.4, 48.0.

EXAMPLE 42

5-(2,3-Dihydroxypropionylamino)-3-hydroxymethyl-N,N-bis(2-hydroxyethyl)-2,4,6-triiodobenzamide a. 5-(2,2-Dimethyl-1,3-dioxolane-4-carbamido)-3-acetoxymethyl-N,N-bis(2-acetoxy-ethyl)-2,4,6-triiodobenzamide Prepared according to Example 29a from 5-amino-3-acetoxymethyl-N,N-bis(2-acetoxyethyl)-2,4,6-triiodobenzamide. After work up the product was isolated in 96% yield.

MS (ESP, m/e): 885 ([M]+, 100%).

$^1$H NMR (CDCl$_3$): 8.51, 8.42, 8.26 (3s, 1H), 5.53 (s, 2H) 4.54–4.70 (m, 4H), 4.18–4.44 (m, 7H), 2.08, 2.05, 2.04 (3s, 9H), 1.62, 1.61, 1.55, 1.40 (4s, 6H).

$^{13}$C NMR (CDCl$_3$): 170.7, 170.6, 170.4, 170.2, 169.6, 169.2, 148.6, 143.0, 142.3, 111.9, 111.7, 111.4, 98.3, 98.0, 97.3, 75.2, 72.8, 67.1, 62.6, 61.3, 48.5, 45.0, 26.7, 26.4, 26.3, 25.7, 24.8, 21.3, 20.9, 20.5.

b. 5-(2,3-Dihydroxypropionylamino)-3-hydroxymethyl-N, N-bis(2-hydroxyethyl)-2,4,6-triiodobenzamide Prepared from the product of Example 42a according to the method in Example 29b. Isolated in 40% yield after preparative HPLC.

MS (ESP, m/e): 720 ([M]+, 100%).

$^1$H NMR (DMSO-d$_6$): 9.83, 9.77 (2s, 1H), 5.84 (s, 1H), 5.14–5.40 (m, 1H), 4.49 (s, 2H), 4.83 (br. S, 3H), 4.06 (br. s, 1H), 3.48–3.80 (m, 8H), 3.08–3.18 (m, 2H).

$^{13}$C NMR (DMSO-d$_6$): 170.5, 170.3, 148.5, 148.4, 146.5, 143.7, 106.9, 99.1, 99.0, 97.6, 97.5, 97.4, 74.6, 73.8, 72.0, 54.2, 63.6, 59.0, 57.7, 51.7, 48.1.

EXAMPLE 43

5-[N'-(2-Hydroxyethyl)-2,3-dihydroxypropionylamino]-3-hydroxy-methyl-N,N-bis (2-hydroxyethyl)-2,4,6-triiodobenzamide a. 5-[N'-(2-acetoxyethyl)-2,2-dimethyl-1,3-dioxolane-4-carbamido]-3-acetoxymethyl-N,N-bis (2-acetoxyethyl)-2,4,6-triiodobenzamide Alkylation of the compound of Example 42a with 2-bromoethyl acetate was performed as described in Example 30 a. The product was isolated as raw material in a yield of 80%.

MS (ESP, m/e): 972 ([M]+, 100%), 1104 ([M+Cs]+, 20%).

$^1$H NMR (CDCl$_3$): 5.59, 5.57 (2s, 2H), 4.57–4.63 (m, 1H), 4.18–4.47 (m, 10H), 3.81–3.88 (m, 2H), 3.40–3.51 (m, 2H), 2.08, 2.06 (2s, 12H), 1.62, 1.49, 1.40 (3s, 6H)

$^{13}$C NMR (CDCl$_3$): 171.0, 170.9, 170.5, 170.2, 170.0, 169.5, 149.8, 149.6, 148.9, 147.9, 144.0,, 143.7, 143.5, 111.3, 110.9, 108.4, 98.3, 97.4, 91.6, 75.2, 73.8, 67.8, 67.1, 62.8, 62.1, 61.8, 61.5, 61.2, 48.6, 48.2, 45.1, 26.5, 25.7, 25.5, 25.4, 20.9, 20.8, 20.6, 20.4.

b. 5-[N'-(2-Hydroxyethyl)-2,3-dihydroxypropionylamino]-3-hydroxymethyl-N,N-bis(2-hydroxyethyl-2,4,6-triiodobenzamide The product of Example 43a was hydrolysed according the general method in Example 30b. After preparative HPLC the product was isolated in 22% yield.

MS (ESP, m/e): 763 ([M]+, 100%)

$^1$H NMR (DMSO-d$_6$): 5.15–5.41 (m, 1H), 4.70–5.02 (m, 5H) 4.06–4.62 (br. m, 2H), 3.45–3.75 (m, 9H), 3.30–3.45 (m, 2H), 3.10–3.22 (m, 2H)

$^{13}$C NMR (DMSO-d$_6$): 172.5, 171.6, 171.5, 171.3, 171.2, 171.1, 170.3, 149.7, 149.6, 149.5, 149.3, 148.3, 148.2, 147.7, 147.6, 147.4, 147.3, 147.2, 147.1, 109.1, 108.9, 108.2, 108.0, 107.0, 101.5, 101.3, 100.8, 100.3, 99.1, 99.0, 98.1, 75.0, 74.9, 74.7, 72.0, 71.9, 71.5, 71.4, 71.2, 70.8, 70.6, 70.5, 63.8, 63.6, 63.5, 63.4, 59.3, 59.0, 58.9, 58.3, 58.2, 57.6, 52.0, 51.8, 51.7, 48.1, 47.9.

EXAMPLE 44

5-Hydroxyacetamido-3-hydroxyethyl-N-methyl-N-(2,3-dihydroxy-propyl)-2,4,6-triiodobenzamide a. 5-Amino-3-acetoxymethyl-N-methyl-N-(2,3-dihydroxypropyl)-2,4,6-triiodo-benzamide 5-Amino-3-acetoxymethyl-2,4,6-triiodobenzoyl chloride was reacted with N-methyl-2,3-dihydroxypropylamine according to the conditions in Example 24g. The product was isolated in 97% yield.

$^1$H NMR (DMSO-d$_6$): 5.35 (s, 2H), 4.98 (br. s, 4H), 3.89 (m, 1H), 3.57–3.70 (m, 1H), 3.35–3.51 (m, 3H), 3.12–3.22 (m, 1H), 2.80 (s, 3H), 2.04 (s, .3H).

$^{13}$C NMR (DMSO-d$_6$): 170.7, 170.0, 148.6, 148.2, 140.0, 87.9, 81.6, 80.7, 76.8, 69.7, 66.4, 64.2, 50.2, 37.3, 20.4.

b. 5-Amino-3-acetoxymethyl-N-methyl-N-(2,3-diacetoxypropyl)-2,4,6-triiodobenzamide After acetylation of the compound of Example 44a according to the procedure of Example 24h the product was isolated in 93% yield.

MS (ESP, m/e): 758 ([M]+, 100%).

$^1$H NMR (DMSO-d$_6$) 5.49 (s, 2H), 5.41–5.49 (m, 1H), 5.10 (br. s, 2H), 4.49–4.57 (m, 1H), 4.20–4.30 (m, 1H), 4.03– 4.15 (m,1H), 3.38–3.52 (m, 1H), 2.94 (s, 3H), 2.10 (s, 9H).

c. 5-Acetoxyacetamido-3-acetoxymethyl-N-methyl-N-(2,3-diacetoxypropyl)-2,4,6-triiodobenzamide The compound of Example 44b was acylated according to the procedure of Example 24 i, affording the product in 89% yield.

$^1$H NMR (CDCl$_3$) 9.11, 9.03 (2s, 1H), 5.53 (br. s, 2H) 5.40–5.51 (m, 1H), 4.80 (s, 2H), 4.45–4.56 (m, 1H), 3.95–4.30 (m, 2H), 3.33–3.53 (m, 1H), 2.92 (s, 3H), 2.25, 2.10, 2.09 (3s, 12 H).

$^{13}$C NMR (CDCl$_3$): 171.2, 170.5, 170.3, 170.0, 169.9, 169.7, 165.7, 143.0, 142.9, 142.8, 107.0, 97.7, 96.8, 96.4, 70.0, 63.6, 63.0, 48.3, 48.2, 37.8, 21.3, 21.2, 20.8, 20.7, 20.6.

d. 5-Hydroxyacetamido-3-hydroxymethyl-N-methyl-N-(2, 3-dihydroxypropyl)-2,4,6-triiodobenzamide Deacetylation of the product of Example 44c according to the procedure of Example 24j, gave the product in 56% yield after preparative HPLC.

MS (ESP, m/e): 690 ([M]+, 100%).

$^1$H NMR (DMSO-d$_6$): 9.85, 9.77 (2s, 1H), 5.69 (t, 1H, J=5 Hz), 5.21 (t, 1H, J=5 Hz), 4.93 (d, 2H, J=2 Hz), 4.76 (d, 1H, J=5 Hz), 4.61 (t, 1H, J=5 Hz), 3.89, 4.00 (2d, 2H, J=5 Hz), 3.60–3.79 (m, 1H), 3.12–3.48 (m, 2H), 3.05, 2.82, 2.80 (3s, 3H).

$^{13}$C NMR (DMSO-d$_6$): 170.5, 170.4, 148.9, 146.5, 143.6, 106.8, 98.3, 96.9, 96.8, 74.5, 69.7, 64.2, 61.8, 50.2, 37.2.

EXAMPLE 45

5-[N'-(2-Hydroxyethyl)-hydroxyacetamido]-3-hydroxymethyl-N-methyl-N-(2,3-dihydroxypropyl)-2,4,6-triiodobenzamide a. 5-[N'-(2-Acetoxyethyl)-acetoxyacetamido]-3-acetoxymethyl-N-methyl-N-(2,3-diacetoxypropyl)-2,4,6-triiodobenzamide The alkylation of 5-acetoxyacetamido-3-acetoxymethyl-N-methyl-N-(2,3-diacetoxypropyl)-2,4,6-triiodobenzamide followed the procedure of Example 25a. The yield of isolated crude product was 96%.

MS (ESP, m/e): 944 ([M]+, 100,%)

$^1$H NMR (CDCl$_3$): 5.56 (br. s, 2H), 5.39–5.47 (m, 1H), 4.17–4.55 (m, 6H), 3.73–4.15 (m, 3H), 3.50 (t, 1H, J=6 Hz), 2.92, 2.95 (2s, 3H), 2.12, 2.11, 2.08, 1.97, 1.95 (5s, 15H).

$^{13}$C NMR (CDCl$_3$) 170.5, 170.3, 170.2, 170.1, 170.0, 166.4, 165.9, 151.0, 146.6, 144.5, 144.4, 144.3, 107.3, 98.9, 98.5, 98.3699, 69.8, 63.7, 63.4, 62.7, 62.1, 61.9, 61.4, 61.2, 48.8, 48.4, 47.9, 37.3, 28.6, 21.2, 20.9, 20.7, 20.5, 20.4.

b. 5-[N'-(2-Hydroxyethyl)-hydroxyacetamido]-3-hydroxymethyl-N-methyl-N-(2,3-dihydroxypropyl)-2,4,6-triiodobenzamide Hydrolysis of the compound of Example 45a according to the procedure of Example 25b, left the product in 40% yield after preparative HPLC.

MS (ESP, m/e): 734 ([M]⁺, 100%)

¹H NMR (DMSO-d₆): 5.23 (t, 1H, J=5 Hz), 4.91–5.03 (m, 3H), 4.58–4.82 (m, 3H), 3.84–3.94 (m, 1H), 3.40–3.72 (m, 9H), 3.00–3.24 (m, 1H), 3.07, 3.05, 2.81 (3s, 3H).

¹³C NMR (DMSO-d₆): 170.9, 170.8, 170.2, 150.2, 150.1, 148.1, 148.0, 146.2, 146.1, 144.7, 107.8, 107.7, 99.6, 99.4, 98.9, 98.7, 74.6, 69.6, 64.2, 63.8, 61.5, 58.5, 58.4, 51.6, 51.1, 50.2, 37.2, 37.1.

EXAMPLE 46

5-(2,3-Dihydroxypropionylamino)-3-hydroxymethyl-N-methyl-N-(2,3-dihydroxypropyl-2,4,6-triiodobenzamide a. 5-(2,2-Dimethyl-1,3-dioxolane-4-carbamido)-3-acetoxymethyl-N-methyl-N-(2,3-diacetoxypropyl)-2,4,6-triiodobenzamide 5-Amino-3-acetoxymethyl-N-methyl-N-(2,3-diacetoxypropyl)-2,4,6-triiodobenzamide was acylated according to the procedure in Example 29a. The crude product was isolated in 96% yield.

¹H NMR (CDCl₃): 8.46, 8.41, 8.24 (3s, 1H), 5.52 (s, 2H), 5.38–5.47 (m, 1H), 4.53–4.68 (m 2H), 4.42–4.60 (m, 1H), 4.16–4.39 (m,2H,) 3.95–4.12 (m, 1H), 3.36–3.48 (m, 1H), 2.98 (s, 3H), 2.08, 2.06 (2s, 9H), 1.65, 1.63, 1.62, 1.55, 1.43, 1.36 (6s, 6H).

¹³C NMR (CDCl₃): 170.7, 170.6, 170.5, 170.2, 170.0, 149.4, 142.9, 142.2, 111.7, 111.5, 105.9, 97.5, 97.2, 75.2, 73.8, 73.7, 72.8, 70.0, 67.1, 63.5, 62.6, 47.91, 30.0, 25.7, 21.4, 21.2, 20.7, 20.5.

b. 5-( 2,3-Dihydroxypropionylamino)-3-hydroxymethyl-N-methyl-N-(2,3-dihydroxypropyl)-2,4,6-triiodobenzamide The hydrolysis and ketal cleavage of the compound of Example 46a were performed according to the procedure of Example 29b. The product was isolated in a yield of 30% after preparative HPLC.

MS (ESP, m/e): 719 ([M]⁺, 100%).

¹H NMR (DMSO-d₆): 9.84, 9.75 (2s, 1H), 5.84 (d, 1H, J=6 Hz), 5.20 (t, 2H, J=5 Hz), 4.93 (d, 2H, J=5 Hz), 4.74–4.86 (m, 2H), 4.60 (t, 1H, J=6 Hz), 4.00–4.35 (m, 2H), 3.84–3.93 (m, 1H), 3.73–3.82 (m, 1H), 3.51–3.68 (m, 2H), 3.40–3.48 (m, 1H), 3.09–3.23 (m, 1H), 2.80 (br. s, 3H).

¹³C NMR (DMSO-d₆): 172.7, 170.5, 148.8, 146.5, 144.7, 143.7, 106.8, 106.6, 98.2, 96.8, 96.7, 74.5, 73.8, 72.0, 69.7, 64.2, 63.9, 63.7, 50.2, 37.2.

EXAMPLE 47

5-[N'-(2-Hydroxyethyl)-2,3-dihydroxypropionylamino]-3-hydroxymethyl-N-methyl-N-(2,3-dihydroxypropyl)-2,4,6-triiodobenzamide a. 5-[N'-(2-Acetoxyethyl)-2,2-dimethyl-1,3-dioxolane-4-carbamido]-3-acetoxymethyl-N-methyl-N-(2,3-dihydroxypropyl)-2,4,6-triiodobenzamide 5-(2,2-dimethyl-1,3-dioxolane-4-carbamido)-3-acetoxymethyl-N-methyl-N-(2,3-diacetoxypropyl)-2,4,6-triiodobenzamide was alkylated according to the conditions in Example 30a. The crude product was isolated in a yield of 88%.

MS (ESP, m/e): 971 ([M]⁺, 100%).

¹H NMR (CDCl₃): 5.54 (br. s, 2H), 5.38–5.45 (m, 1H), 3.98–4.54 (m, 10H), 3.30–3.52 (m, 1H), 2.94, 2.88 (2s, 3H), 2.06, 2.05 (2 br s, 9H), 1.60, 1.46, 1.43, 1.37, 1.30 (5s, 6H).

¹³C NMR (CDCl₃): 170.4, 170.3, 170.1, 170.0, 150.6, 150.3, 147.8, 143.7, 143.3, 111.5, 111.4, 110.9, 99.1, 98.7, 97.8, 96.7, 75.4, 73.8, 69.9, 67.9, 67.2, 63.7, 63.4, 62.8, 62.1, 61.8, 61.4, 48.7, 47.9, 37.3, 28.6, 26.5, 25.6, 25.4, 21.2, 20.9, 20.5, 20.4.

b. 5-[N'-(2-Hydroxyethyl)-2,3-dihydroxypropionylamino]-3-hydroxymethyl-N-methyl-N-(2,3-dihydroxypropyl)-2,4,6-triiodobenzamide Hydrolysis and ketal cleavage of the compound of Example 47a according to the procedure of Example 30b, followed by preparative HPLC afforded the product in a yield of 20%.

MS (ESP, m/e): 763 ([M]⁺, 100%)

¹H NMR (DMSO-d₆): 5.18 (br. s, 1H), 4.95 (d, 2H, J=4 Hz), 4.71 (br. s, 1H), 4.42–4.50 (m, 1H), 4.12 (br. s, 1H), 3.90 (br. s, 2H), 3.08–3.76 (m, 12H,), 2.80 (s, 3H),

¹³C NMR (DMSO-d₆): 171.6, 171.5, 171.3, 171.2, 171.0, 170.4, 167.7, 150.0, 149.9, 149.8, 148.2, 147.7, 147.6, 147.4, 147.3, 147.2, 147.1, 144.7, 109.0, 108.8, 108.1, 107.8, 106.6, 100.7, 99.6, 99.5, 98.3, 98.2, 97.4, 97.3, 74.9, 74.7, 74.6, 74.5, 72.0, 71.8, 71.6, 71.4, 71.2, 71.0, 70.8, 70.7, 70.6, 69.6, 64.2, 63.7, 63.5, 59.3, 58.3, 58.2, 51.9, 51.8, 51.7, 51.4, 50.3, 37.2.

EXAMPLE 48

5-Hydroxyacetamido-3-hydroxymethyl-N-(1,3-dihydroxyprop-2-yl)-2,4,6-triiodobenzamide a. 5-Amino-3-acetoxymethyl-N-(1,3-dihydroxyprop-2-yl)-2,4,6-triiodobenzamide 5-Amino-3-acetoxymethyl-2,4,6-triiodobenzoyl chloride was reacted with serinol according to the conditions in Example 24g. The product was isolated in 95% yield.

¹H NMR (DMSO-d₆): 8.12 (d, 1H, J=7 Hz), 5.38 (s, 2H), 4.76 (br. s, 4H), 3.82 (m, 1H), 3.60–3.68 (m, 2H), 3.47–3.57 (m, 2H), 2.04 (s, 3H).

¹³C NMR (DMSO-d₆): 170.0, 169.8, 149.5, 148.2, 139.4, 87.6, 82.3, 81.7, 77.0, 66.4, 59.3, 53.1, 20.4.

b. 5-Amino-3-acetoxymethyl-N-(1,3-diacetoxyprop-2-yl)-2,4,6-triiodobenzamide

Acetylation of the compound of Example 48a was performed smoothly according to the conditions given in Example 24h. The product was isolated, after purification, in 98% yield.

(MS ESP, m/e): 744 ([M]⁺, 100%).

¹H NMR (CDCl₃): 6.17 (d, 1H, J=7 Hz), 5.50 (s, 2H), 4.61–4.69 (m, 1H), 4.24 (m, 4H), 2.21, 2.11, 2.08 (3s, 9H).

¹³C NMR (CDCl₃): 170.8, 170.4, 169.8, 148.4, 147.8, 140.9, 87.8, 81.0, 79.6, 62.3, 47.9, 22.1, 20.9, 20.6, 20.5.

c. 5-Acetoxyacetamido-3-acetoxymethyl-N-(1,3-diacetoxyprop-2-yl)-2,4,6-triiodobenzamide Acylation of the compound of Example 48b was effected according to the method in Example 24i. The product was isolated in 92% yield.

MS (ESP, m/e): 844 ([M]⁺, 100%).

¹H NMR (DMSO-d₆): 8.49, 8.47 (2s, 1H), 5.48 (s, 2H), 5.22 (d, 1H, J=6 Hz), 4.70 (s, 2H), 4.45–4.53 (m, 1H ), 4.16–4.25 (m, 4H), 2.00, 1.98 (2s, 12H).

¹³C NMR (CDCl₃): 170.9, 170.5, 170.1, 167.1, 149.8, 142.4, 142.1, 106.0, 97.6, 97.0, 62.6, 62.1, 62.0, 49.4, 49.1, 48.8, 48.5, 48.3, 47.2, 20.6, 20.3.

d. 5-Hydroxyacetamido-3-hydroxymethyl-N-(1,3-dihydroxyprop-2-yl)-2,4,6-triiodobenzamide Hydrolysis of the compound of Example 48c according to the procedure of Example 24j afforded a yield of 55% after HPLC purification.

MS (ESP, m/e): 676 ([M]⁺, 100%).

EXAMPLE 49

5-[N'-(2-Hydroxyethyl)-hydroxyacetamido]-3-hydroxymethyl-N-(1,3-dihydroxyprop-2-yl)-2,4,6-triiodobenzamide a. 5-[N'-(2-Acetoxyethyl)-acetoxyacetamido]-3-acetoxymethyl-N-(1,3-diacetoxyprop-2-yl)-2,4,6-triiodobenzamide Alkylation of the compound of Example 48c with 2-bromoethyl acetate was performed according to the procedure of Example 25a. The product was isolated in 86% yield.

MS (ESP, m/e): 924 ([M]+, 100%).

$^1$H NMR (CDCl$_3$): 6.58 (d, 1H, J=5 Hz), 5.52 (s, 2H), 4.52–4.65 (m, 1H), 4.18–4.38 (m, 7H), 3.73–3.95 (m, 2H), 3.55 (t, 1H, J=5 Hz), 2.07, 2.04 (2s, 15H).

$^{13}$C NMR (DMSO-d$_3$): 170.8, 170.6, 170.4, 170.2, 169.9, 166.0, 151.1, 146.5, 145.9, 144.0, 108.0, 107.9, 99.9, 99.3, 98.8, 98.5, 63.6, 62.6, 62.0, 61.7, 60.9, 48.7, 48.2, 47.9, 47.7, 28.6, 20.8, 20.7, 20.6, 20.4.

b. 5-[N'-(2-Hydroxyethyl)-hydroxyacetamido]-3-hydroxymethyl-N-(1,3-dihydroxyprop-2-yl)-2,4,6-triiodobenzamide Hydrolysis of the compound of Example 49a according to the method of Example 25b, gave, after HPLC purification, an isolated yield of 26%.

MS (ESP, m/e): 743 ([M]+, 100%).

EXAMPLE 50

5(2,3-Dihydroxypropionylamino)-3-hydroxymethyl-N-(1,3-dihydroxyprop-2-yl)-2,4,6-triiodobenzamide a. 5-(2,2-Dimethyl-1,3-dioxolane-4-carboxamido)-3-acetoxymethyl-N-(1,3-diacetoxyprop-2-yl)-2,4,6-triiodobenzamide 5-Amino-3-acetoxymethyl-N-(1,3-diacetoxyprop-2-yl)-2,4,6-triiodobenzamide was acylated according to the procedure in Example 29a. The crude product could be isolated in 94% yield.

$^1$H NMR (CDCl$_3$): 8.39, 8.47 (2s, 1H), 6.63–6.76 (m, 1H), 5.55 (s, 2H), 4.54–4.68 (m, 2H), 4.18–4.40 (m, 6H), 2.08, 2.05 (2s, 9H), 1.66, 1.64, 1.55, 1.44, 1,37 (5s, 6H).

$^{13}$C NMR (CDCl$_3$): 170.7, 170.6, 170.5, 169.6, 169.1, 149.0, 142.8, 142.0, 111.7, 111.5, 106.4, 106.2, 97.6, 97.3, 75.2, 73.8, 73.7, 72.8, 67.1, 26.9, 25.7, 25.4, 21.4, 20.8, 20.5.

b. 5-(2,3-Dihydroxypropionylamino)-3-hydroxymethyl-N-(1,3-dihydroxyprop-2-yl)-2,4,6-triiodobenzamide Hydrolysis and ketal cleavage of the compound of Example 50a were performed according to the procedure of Example 29b. After preparative HPLC the product was isolated in 33% yield.

MS (ESP, m/e): 705 ([M]+, 100%).

EXAMPLE 51

5-[N'-(2-Hydroxyethyl)-2,3-dihydroxypropionylamino]-3-hydroxy-methyl-N-(1,3-dihydroxyprop-2-yl)-2,4,6-triiodobenzamide a. 5-[N'-(2-Acetoxyethyl)-2,2-dimethyl-1,3-dioxolane-4-carboxamido]-3-acetoxymethyl-N-(1,3-diacetoxyprop-2-yl)-2,4,6-triiodobenzamide The alkylation of 5-(2,2-dimethyl-1,3-dioxolane-4-carboxamido)-3-acetoxymethyl-N-(1,3-diacetoxyprop-2-yl)-2,4,6-triiodobenzamide with 2-bromoethyl acetate was performed according to the procedure of Example 30a. The crude product was isolated in 83% yield.

MS (ESP, m/e): 958 ([M]+, 100%).

$^1$H NMR (CDCl$_3$): 6.71 (d,1H, J=5 Hz), 5.51 (s, 2H), 4.52–4.59 (m, 2H), 3.76–4.36 (m, 9H), 3.46 (t, 1H, J=6 Hz), 2.10, 2.04, 2.00 (3s, 12H), 1.58, 1.44, 1.40, 1.34 (4s, 6H).

$^{13}$C NMR (CDCl$_3$): 170.6, 170.4, 170.1, 169.9, 169.1, 150.8, 150.5, 143.7, 143.6, 143.4, 142.7, 142.0, 111.7, 111.3, 111.1, 110.9, 97.7, 97.2, 75.1, 73.8, 67.9, 67.1, 63.7, 62.8, 62.1, 61.7, 61.0, 49.1, 47.9, 47.5, 30.7, 28.6, 26.4, 25.9, 25.6, 25.5, 24.8, 20.8, 20.7, 20.5.

b. 5-[N'-(2-Hydroxyethyl)-2,3-dihydroxypropionylamino]-3-hydroxymethyl-N-(1,3-dihydroxyprop-2-yl)-2,4,6-triiodobenzamide Hydrolysis and ketal cleavage of the product of Example 51a were performed according to the procedure of Example 30b. After preparative HPLC the product was isolated in 25% yield.

MS (ESP, m/e): 750 ([M]+, 100%).

EXAMPLE 52

5-(2,3-Dihydroxypropionylamino)-3-hydroxymethyl-N-(2-hydroxyethyl)-2,4,6-triiodobenzamide a. 5-Amino-3-acetoxymethyl-N-(2-hydroxyethyl)-2,4,6-triiodobenzamide 5-Amino-3-acetoxymethyl-2,4,6-triiodobenzoyl chloride was reacted with ethanolamine according to the general procedure in Example 24g. The yield of isolated product was 98%.

$^1$H NMR (DMSO-d$_6$): 8.41 (t, 1H, J=6 Hz), 5.45 (br. s, 2H), 5.38 (s, 2H), 3.51–3.57 (m, 2H), 3.40 (s, 1H), 3.21–3.29 (m, 2H), 2.04 (s, 3H).

b. 5-Amino-3-acetoxymethyl-N-(2-acetoxyethyl)-2,4,6-triiodobenzamide

Acetylation of the compound of Example 52a was performed according to the method of Example 24h. The product, after purification, was isolated in 97% yield.

$^1$H NMR (CDCl$_3$): 7.81 (t, 1H, J=6 Hz), 5.14 (s, 2H), 3.92 (t, 2H, J=6 Hz), 3.27 (m, 2H), 2.85–3.36 (br. s, 2H), 1.74, 1.72 (2s, 6H).

$^{13}$C NMR (CDCl$_3$): 169.9, 169.3, 149.3, 148.9, 147.1, 139.4, 136.0, 86.1, 80.5, 79.5, 61.4, 37.7, 20.2, 19.8.

c. 5-(2.2-Dimethyl-1,3-dioxolane-4-carboxamido)-3-acetoxymethyl-N-(2-acetoxyethyl)-2,4,6-triiodobenzamide The general acylation method in Example 29a was followed for the compound of Example 52b. The resultant product was isolated in 97% yield.

$^1$H NMR (CDCl$_3$): 8.43, 8.39, 8.29 (3s, 1H), 6.55–6.64 (m, 1H), 5.56 (s, 2H), 4.54–4.70 (m, 2H), 4.24–4.36 (m, 3H), 3.66–3.76 (m, 2H), 2.08, 2.03 (2s, 6H), 1.67, 1.64, 1.57, 1.56, 1.47, 1.45 (6s, 6H).

$^{13}$C NMR (CDCl$_3$): 171.1, 170.9, 169.7, 169.3, 156.2, 150.4, 150.2, 142.9, 142.0, 141.6, 112.0, 111.8, 111.6, 97.8, 97.5, 75.3, 73.8, 72.9, 72.8, 72.6, 72.5, 67.2, 64.7, 64.4, 62.7, 62.5, 38.9, 30.9, 26.8, 26.5, 25.7, 25.5, 21.0, 20.6.

d. 5-(2,3-Dihydroxypropionylamino)-3-hydroxymethyl-N-(2-hydroxyethyl)-2,4,6-triiodobenzamide Hydrolysis and ketal cleavage of the product of Example 52c were performed according to the procedure of Example 29b. After preparative HPLC the product was isolated in 50% yield.

MS (ESP, m/e): 675 ([M]+, 100%).

$^1$H NMR (DMSO-d$_6$): 9.79, 9.77 (2s, 1H), 8.38–8.54 (m, 1H), 5.80 (s, 1H), 5.18 (br. s, 1H), 4.95 (s, 2H), 4.81 (br. s, 1H), 4.65 (br. s, 1H), 4.05 (s, 1H), 3.84 (d, 1H, J=8 Hz), 3.50–3.62 (m, 3H), 3.20–3.32 (m, 2H).

$^{13}$C NMR (DMSO-d$_6$): 170.5, 170.4, 170.0, 150.3, 146.0, 143.3, 143.1, 106.7, 106.5, 106.4, 98.7, 98.5, 97.4, 97.2, 74.6, 73.8, 72.1, 64.2, 63.6, 59.2, 41.7.

EXAMPLE 53

5-[N'-(2-Hydroxyethyl)-2,3-dihydroxypropionylamino]-3-hydroxy-methyl-N-(2-hydroxyethyl)-2,4,6-triiodobenzamide a. 5-[N'-(2-Acetoxyethyl)-2,2-dimethyl-1,3-dioxolane-4-carboxamido]-3-acetoxymethyl-N-(2-acetoxyethyl)-2,4,6-triiodobenzamide The alkylation procedure with 2-bromoethyl acetate given in Example 30a was followed for the product of Example 52c to give 89% yield of the product.

$^1$H NMR (CDCl$_3$): 6.35–6.82 (m, 1H), 5.56 (s, 2H), 4.55–4.70 (m, 1H), 4.04–4.40 (m, 6H), 3.68–3.77 (m, 2H), 3.45–3.53 (t, 2H, J=6 Hz), 2.09, 2.07, 2.05 (3s, 9H), 1.66, 1.65, 1.62, 1.49, 1.46, 1.45, 1.39 (7s, 6H).

$^{13}$C NMR (CDCl$_3$): 170.9, 170.3, 169.7, 149.9, 144.0, 142.9, 142.4, 111.9, 111.4, 106.1, 97.7, 97.5, 91.7, 75.2, 74.0, 72.9, 72.6, 67.2, 64.1, 63.8, 63.6, 62.9, 62.6, 62.5, 61.8, 61.4, 61.2, 49.5, 48.0, 39.1, 38.9, 30.9, 28.6, 28.3, 26.8, 26.4, 26.2, 25.4, 21.2, 20.6.

b. 5-[N'-(2-Hydroxyethyl)-2,3-dihydroxypropionylamino]-3-hydroxymethyl-N-(2-hydroxyethyl)-2,4,6-triiodobenzamide Hydrolysis and ketal cleavage of the compound of Example 53a were performed according to the procedure of Example 30b. Isolated yield, after preparative HPLC was 22%.

MS (ESP, m/e): 720 ([M]$^+$, 100%).

EXAMPLE 54

5-Hydroxyacetamido-3-hydroxymethyl-N-[tris-(hydroxymethyl)-methyl]-2,4,6-triiodobenzamide a. 5-Amino-3-acetoxymethyl-N-[tris-(hydroxymethyl)-methyl]-2,4,6-triiodobenzamide 5-Amino-3-acetoxymethyl-2,4,6-triiodobenzoyl chloride (9.0 g, 14.9 mmol) and sodium carbonate (1.58 g, 14.9 mmol) were mixed in dry dioxane (30 ml). Tris-(hydroxymethyl)aminomethane (1.81 g, 14.9 mmol) was added and the mixture was refluxed for 4.5 days. The reaction mixture was worked up as described in Example 24g. A product mixture mainly consisting of two products was isolated, and separated by preparative HPLC.

5-Amino-3-acetoxymethyl-N-[tris-(hydroxymethyl)-methyl]-2,4,6-triiodobenzamide was isolated in a yield of 2.0 g (20%)

$^1$H NMR (DMSO-d$_6$): 7.80, 7.65 (2s, 1H), 5.37 (s, 2H), 3.45–4.08 (m, 11H), 2.04 (s, 3H).

5-Amino-3-hydroxymethyl-N-[tris-(hydroxymethyl)-methyl]-2,4,6-triiodobenzamide was isolated in a yield of 2.1 g.

$^1$H NMR (DMSO-d$_6$): 7.67 (br. s, 1H), 4.87 (s, 2H), 4.42 (br. s, 2H), 4.15 (s, 4H), 3.69 (s, 6H).

b. 5-Amino-3-acetoxymethyl-N-[tris-(acetoxymethyl)-methyl]-2,4,6-triiodobenzamide The two products of Example 54a were acetylated as described in Example 24h. The acetylated products were isolated in yields of 81% and 74% respectively.

$^1$H NMR (CDCl$_3$): 6.18, 5.92 (2s, 1H), 5.50 (s, 2H), 5.12 (br. s, 2H), 4.50 (br. s, 6H), 2.06 (s, 12H)

c. 5-Acetoxyacetamido-3-acetoxymethyl-N-[tris-(acetoxymethyl)-methyl]-2,4,6-triiodobenzamide Acylation of the product of Example 54b with acetoxyacetyl chloride was performed according to the procedure of Example 24i. The isolated yield was 97%.

MS (ESP, m/e): 916 ([M]$^+$, 100%).

$^1$H NMR (CDCl$_3$): 8.74 (s, 1H), 6.58 (s, 1H), 5.55 (s, 2H), 4.76 (s, 2H), 4.58 (br. s, 6H), 2.08, 2.05 (2s, 15H).

$^{13}$C NMR (CDCl$_3$): 170.3, 170.2, 169.6, 165.9, 149.9, 149.3, 143.0, 142.5, 136.6, 107.5, 97.9, 97.3, 63.1, 62.6, 62.3, 58.9, 21,3, 21.0, 20.8.

d. 5-Hydroxyacetamido-3-hydroxymethyl-N-[tris-(hydroxymethyl)-methyl]-2,4,6-triiodobenzamide After hydrolysis of the compound of Example 54c, according to the procedure of Example 24j, and HPLC purification the product was isolated in 73% yield.

MS (ESP, m/e): 706 ([M]$^+$, 100%), 728 ([M+Na]$^+$, 19%).

EXAMPLE 55

5-[N'-(2-Hydroxyethyl)-hydroxyacetamido]-3-hydroxymethyl-N-[tris-(hydroxymethyl)-methyl]-2,4,6-triiodobenzamide a. 5-[N'-(2-Acetoxyethyl)-acetoxyacetamido]-3-acetoxymethyl-N-[tris-(acetoxymethyl)-methyl]-2,4,6-triiodobenzamide Alkylation of the product of Example 54c was performed according to the procedure of Example 25a. The yield of crude product was 98%.

MS (ESP, m/e): 997 ([M]$^+$, 100%), 1131 ([M+Cs]$^+$, 15%).

$^1$H NMR (CDCl$_3$): 6.54, 6.35, 6.25 (3s, 1H), 5.57 (br. s, 2H), 4.77, 4.72, 4.62, 4.58, 4.56, 4.53, 4.42 (7s, 8H), 4.28–4.38 (m, 2H), 3.45–4.26 (m, 2H), 2.13, 2.11, 2.09, 2.07, 1.95, 1.90 (6s, 18H).

$^{13}$C NMR (CDCl$_3$): 170.8, 170.6, 170.5, 170.3, 170.2, 170.1, 170.0, 168.7, 166.3, 166.1, 151.0, 146.8, 146.1, 144.3, 108.3, 108.1, 99.9, 99.4, 98.8, 98.5, 62.7, 62.5, 62.1, 61.8, 61.0, 59.7, 59.3, 58.9, 48.8, 47.6, 21.0, 20.9, 20.8, 20.7, 20.5.

b. 5-[N'-(2-Hydroxyethyl)-hydroxyacetamido]-3-hydroxymethyl-N-[tris-(hydroxymethyl)-methyl]-2,4,6-triiodobenzamide Hydrolysis of the product of Example 55a was performed according to the procedure of Example 25b. After HPLC purification the compound was isolated in 67% yield.

MS (ESP, m/e): 750 ([M]$^+$, 100%)

EXAMPLE 56

5-(2,3-Dihydroxypropionylamino)-3-hydroxymethyl-N-[tris-(hydroxymethyl)-methyl]-2,4,6-triiodobenzamide a. 5-(2,2-Dimethyl-1,3-dioxolane-4-carbamido)-3-acetoxymethyl-N-[tris-(acetoxymethyl)-methyl]-2,4,6-triiodobenzamide 5-Amino-3-acetoxymethyl-N-[tris-(acetoxymethyl)-methyl]-2,4,6-triiodobenzamide was acylated according to the general method in Example 29a. The product was isolated in 81% yield.

MS (ESP, m/e): 944 ([M]$^+$, 100%).

$^1$H NMR (CDCl$_3$): 9.07, 8.75, 8.40, 8.38, 8.30 (5s, 1H), 6.37, 6.28, 5.94 (3s, 1H), 5.55 (br. s, 2H), 3.96–4.65 (m, 9H), 2.09 (br. s, 12H), 1.64, 1.62, 1.48, 1.47 (4s, 6H).

$^{13}$C NMR (CDCl$_3$): 170.6, 170.4, 170.3, 170.2, 170.1, 169.6, 143.8, 142.8, 142.5, 142.2, 136.5, 111.9, 111.6, 111.4, 98.4, 97.6, 97.1, 75.1, 73.8, 73.7, 72.8, 72.7, 72.5, 72.4, 67.0, 64.2, 62.6, 62.5, 62.2, 62.0, 26.7, 26.4, 26.0, 25.6, 25.4, 25.3, 20.8, 20.7, 20.4.

b. 5-(2,3-Dihydroxypropionylamino)-3-hydroxymethyl-N-[tris-(hydroxymethyl)-methyl]2,4 6-triiodobenzamide Hydrolysis and ketal cleavage of the product of Example 56a were performed according to the procedure of Example 29b. After preparative HPLC the product was isolated in 27% yield.

MS (ESP, m/e): 736 ([M]$^+$, 100%).

EXAMPLE 57

5-[N'-(2-Hydroxyethyl)-2,3-dihydroxypropionylamino]-3-hydroxymethyl-N-[tris-(hydroxymethyl)-methyl]-2,4,6-triiodobenzamide a. 5-[N'-(2-Acetoxyethyl)-2,2-dimethyl-1,3-dioxolane-4-carbamido]-3-acetoxymethyl-N-[tris-(acetoxymethyl)-methyl]-2,4,6-triiodobenzamide The alkylation of the product of Example 56a with 2-bromoethyl acetate followed the procedure of Example 30a. The product could be isolated in 75% yield.

MS (ESP, m/e): 1024 ([M]$^+$, 100%).

$^1$H NMR (CD$_3$OD): 5.66, 5.64, 5.62 (3 br s, 1H), 4.61–4.67 (m, 1H), 4.60 (s, 2H), 4.20–4.39 (m, 7H), 4.05–4.13 (m, 1H), 3.57–3.78 (m, 2H), 3.29–3.32 (m, 2H), 2.15, 2.08, 2.07, 2.04, 1.96 (5s, 15H), 1.62, 1.59, 1.58, 1.44, 1.42, 1.36, 1.30 (7s, 6H).

$^{13}$C NMR (CDCl$_3$): 170.8, 170.4, 170.3, 170.1, 149.7, 148.2, 147.6, 143.3, 140.4, 111.1, 98.3, 98.2, 97.7, 73.6, 72.7, 71.5, 66.9, 65.7, 63.8, 63.5, 62.9, 62.6, 62.4, 62.2, 61.9, 61.6, 30.5, 28.4, 26.4, 26.3, 25.8, 25.5, 25.2, 24.5, 20.6, 20.4, 20.2.

b. 5-[N'-(2-Hydroxyethyl)-2,3-dihydroxypropionylamino]-3-hydroxymethyl-N-[tris-(hydroxymethyl)-methyl]-2,4,6-triiodobenzamide Hydrolysis and ketal cleavage of the product of Example 57a were performed according to the general method in Example 30b. After preparative HPLC the product was isolated in 15% yield.

MS (ESP, m/e): 779 ([M]$^+$, 100%).

EXAMPLE 58

5-(2,3-Dihydroxypropionylamino)-2,4,6-triiododibenzyl alcohol a. 5-Nitro-1,3-dibenzyl alcohol 5-Nitro-isophthalic acid (10.5 g, 49.7 mmol) was dissolved in 250 ml tetrahydrofuran. Under inert atmosphere, boron trifluoride diethyl etherate (28.2 g, 0.199 mol) was added. With efficient stirring sodium borohydride (5.07 g, 0.134 mol) was added portionwise during 1h. The procedure of Example 24a was followed.

Yield: 8.4 g (92%) of a white crystalline solid.

$^1$H NMR (CD$_3$COCD$_3$): 8.11 (d, 2H, J=3 Hz), 7.75 (t, 1H, J=3 Hz), 4.75 (s, 4H), 4.64 (br. s, 2H)

b. 5-Amino-1,3-dibenzyl alcohol

5-Nitro-dibenzyl alcohol (8.4 g, 45.7 mmol) was dissolved in methanol (70 ml), and hydrogenated according to Example 24c. The yield was 7.8 g (90%).

$^1$H NMR (DMSO-d$_6$): 9.60–10.80 (br. s, 2H), 7.23 (t, 1H, J=2 Hz), 7.18 (d, 2H, J=3 Hz), 4.49 (s, 4H), 3.95 (br. s, 3H).

c. 5-Amino-2,4,6-triiodo-dibenzyl alcohol

Iodine (5.3 g, 20.8 mmol) was dissolved in a mixture of water and methanol (1:3, 325 ml), which had been made 0.2 M with respect to sodium tetrafluoroborate. The pH of this solution was adjusted to 1.5 with tetrafluoroboric acid. This solution was used as anolyte, and the solution without iodine as the catolyte in an electrolysis cell, where anode and cathode volumes were separated by a fritted glass disk. Current 0.6 A, a charge of 3 F/mol iodine was passed through the solution. The solution was used immediately for iodination. 5-Amino-1,3-dibenzyl alcohol (1.3 g, 6.33 mmol) was dissolved in water (15 ml), and to this solution was added the electrolysis mixture above. The mixture was stirred at 60° C. for 28 h. After cooling to room temperature, a 10% aqueous solution of sodium hydrogen sulphite (3 ml) was added. The mixture was neutralised with aqueous sodium hydroxide, and the methanol was evaporated. A brown precipitate was formed and filtered off. The filtercake was boiled two times with 80 ml of water and filtered, then dried. The product (2.0 g, 59%) was a grey crystalline residue.

$^1$H NMR (DMSO-d$_6$): 5.10–5.58 (br. s, 2H), 4.98 (s, 4H), 3.50 (br s, 2H).

$^{13}$C NMR (DMSO-d$_6$) 147.9, 144.7, 89.9, 87.5, 75.5.

d. 5-Amino-2,4,6-triiodo-1,3-diacetoxymethylbenzene

5-Amino-2,4,6-triiodo-dibenzyl alcohol was acetylated according to the method in Example 24e. After workup the product was chromatographed on a column of alumina using methylene chloride/ethyl acetate (5/1) as the eluent. A white crystalline product was isolated in 78% yield.

$^1$H NMR (CDCl$_3$): 5.63 (s,4H), 5.24 (br. s, 2H), 2.13 (s, 6H).

$^{13}$C NMR (CDCl$_3$): 170.5, 147.8, 140.8, 90.5, 88.4, 78.4, 20.7.

e. 5-(2,2-Dimethyl-1,3-dioxolane-4-carbamido)-2,4,6-triiodo-1,3-diacetoxymethyl-benzene 5-Amino-2,4,6-triiodo-1,3-diacetoxymethylbenzene was acylated according to the procedure in Example 29a. A white crystalline product was formed in 83% yield, after filtration through a pad of alumina with methylene chloride/ethyl acetate (1/1) as eluent.

$^1$H NMR (DMSO-d$_6$): 10.04 (s, 1H), 5.55 (s, 4H), 5.02–5.08 (m, 1H), 4.554–4.80 (m, 1H), 4.05–4.34 (m, 1H), 2.06 (s, 6H), 1.56, 1.54, 1,37, 1.28 (4s, 6H).

$^{13}$C NMR (CDCl$_3$): 170.4, 170.3, 169.3, 143.1, 142.8, 141.9, 111.7, 106.5, 106.4, 105.7, 78.2, 75.3, 67.2, 26.5, 24.9, 20.6.

f. 5-(2,3-Dihydroxypropionylamino)-2,4,6-triiodo-1,3-dibenzyl alcohol

Hydrolysis and ketal cleavage of the product of Example 58e were performed according to the procedure of Example 29b. After preparative HPLC the product was isolated in 43%.

MS (ESP, m/e): 620 ([M]$^+$, 100%).

EXAMPLE 59

5-[N-(2-Hydroxyethyl)-2,3-dihydroxypropionylamino]-2,4,6-triiodo-1,3-dibenzyl alcohol a. 5-[N-(2-Acetoxyethyl)-2,2-dimethyl-1,3-dioxolane-4-carbamido]-2,4,6-triiodo-1,3-diacetoxymethylbenzene 5-(2,2,-Dimethyl-1,3-dioxolane-4-carbamido)-2,4,6-triiodo-1,3-di-(acetoxymethyl) benzene was alkylated with 2-bromoethyl acetate according to Example 30a. The crude product, containing some O-alkylated material was used directly in next step.

MS (ESP, m/e): 830 ([M]$^+$, 100%), 962 ([M+Cs]$^+$, 25%).

b. 5-[N-(2-Hydroxyethyl)-2,3-dihydroxypropionylamino]-2,4,6-triiodo-1,3-dibenzyl-alcohol Hydrolysis and ketal cleavage of the product of Example 59a were performed according to the procedure of Example 30b. The product was isolated in 39% yield after preparative HPLC.

MS (ESP, m/e): 663 ([M]$^+$, 100%).

EXAMPLE 60

5-(2,3,4-Trihydroxybutanoylamino)-2,4,6-triiodo-1,3-dibenzyl alcohol a. 5-(2,3,4-Triacetoxybutanoylamino)-2,4,6-triiodo-1,3-di-(acetoxymethyl)-benzene 5-Amino-2,4,6-triiodo-1,3-di-(acetoxymethyl)benzene (2.0 g, 3.25 mmol) was dissolved in dimethylacetamide (4 ml) at room temperature. 2,3,4-Triacetoxybutyryl chloride (7.4 g, 26.4 mmol) was added and the mixture was stirred for 20 h. The work up was carried out as in Example 24i. A white crystalline product 2.2 g (79%), was isolated.

MS (ESP, m/e): 857 ([M]$^+$, 100%), 880 ([M+Na]$^+$, 20%).

$^1$H NMR (CDCl$_3$): 7.93 (s, 1H), 5.68–5.79 (m, 1H), 5.66, 5.61 (2s, 4H), 4.39–4.55 (m, 2H), 4.16–4.23 (m, 1H), 2.20, 2.17, 2.13, 2.11, 2.10 (5s, 15H).

$^{13}$C NMR (CDCl$_3$): 170.4, 170.2, 169.8, 169.5, 169.2, 169.1, 146.1, 143.0, 142.9, 141.4, 106.5, 106.1, 105.8, 78.2, 71.5, 69.6, 69.4, 69.0, 67.1, 61,3, 21.2, 21.0, 20.8, 20.7, 20.6, 20.5, 20.2.

b. 5-(2,3,4-Trihydroxybutanoylamino)-2,4,6-triiodo-1,3-dibenzyl alcohol

The hydrolysis of the product of Example 60a was performed according to the method of Example 24j, and HPLC purification gave the product in 44% yield.

MS (ESP, m/e): 649 ([M]$^+$, 100%).

EXAMPLE 61

3,5-Bis(2,3-dihydroxypropionylamino)-2,4,6-triiodo-(2-hydroxyethyl)benzene a. 3,5-Dinitro-(2-hydroxyethyl)benzene 3,5-Dinitrostyrene (0.28 g, 1.43 mmol) was dissolved in acetonitrile (150 ml) and water (300 ml) was added. The mixture was poured into a photolysis apparatus and irradiated with an UV-lamp (HPK 125, Phillips) for 3 h. The organic solvent was evaporated and the aqueous phase extracted with methylene chloride (2×100 ml). The solvent was evaporated and the residue was purified by flash chromatography on a column of silica using heptane/ethyl acetate (1/1) as eluent. Evaporation of solvent gave 76 mg (25%) of a crystalline product.

$^1$H NMR (CDCl$_3$): 8.93 (t, 1H, J=3 Hz), 8.48 (d, 2H, J=3 Hz), 4.02 (q, 2H, J=6 Hz), 3.10 (t, 2H, J=6 Hz).

$^{13}$C NMR (CDCl$_3$): 148.4, 143.7, 129.4, 117.0, 62.1, 38.2.

b. 3.5-Diamino-(2-hydroxyethyl)benzene 3,5-Dinitro-(2-hydroxyethyl)benzene (0.18 g, 0.85 mmol) was dissolved in methanol (50 ml) and hydrogenated over Pd/C (10%) in a Parr apparatus at 60 psi. After complete hydrogen uptake the catalyst was filtered off and the solvent was evaporated which gave a solid residue of 0.10 g (81%).

$^1$H NMR (CD$_3$OD): 6.06 (s, 3H), 3.70 (t, 2H, J=7 Hz), 2.64 (t, 2H, J=7 Hz).

c. 3,5-Diamino-2,4,6-triiodo-(2-hydroxyethyl)benzene 3,5-Diamino-(2-hydroxyethyl)benzene (0.18 g, 1.16 mmol) was dissolved in methanol (50 m) and water (4 ml). Hydrochloric acid (1M, 1.3 ml) was added followed by a 70% w/w solution of potassium iododichloride (0.86 g, 3.63 mmol). A precepitate formed immediately and stirring was continued for 5 minutes before the precepitate was filtered off. The filtercake was dried to 0.50 g (81%) in a desiccator.

$^1$H NMR (DMSO-d$_6$): 5.20 (br. s, 2H), 3.38–3.46 (m, 2H) 3.23–3.31 (m,2H).

$^{13}$C NMR (DMSO-d$_6$): 147.6, 142.3, 72.7, 67.3, 59.1, 51.6.

d. 3,5-Diamino-2,4,6-triiodo-(2-acetoxyethyl)benzene

Acetylation of the product of Example 61c was performed according to the method of Example 24e. The product was isolated in 84% yield.

$^1$H NMR (CDCl$_3$): 4.84 (br. s, 2H), 4.24 (t, 2H, J=7 Hz), 3.56 (t, 2H, J=7 Hz), 2.06 (s, 3H).

e. 3,5-Bis(2,2-dimethyl-1,3-dioxolane-4-carbamido)-2,4,6-triiodo-(2-acetoxyethyl)-benzene 3,5-Diamino-2,4,6-triiodo-(2-acetoxyethyl)benzene was acylated with 2,2-dimethyl-1,3-dioxolane-4-carboxylic chloride (prepared in situ) according to the procedure in Example 29a. After work up, the product was purified by preparative HPLC and isolated in 47% yield.

$^1$H NMR (CDCl$_3$): 8.83, 8.88, 8.97, 9.90 (4s, 2H), 4.60–4.72 (m, 2H,), 4.19–4.44 (m, 4H), 3.78–3.94 (m, 4H), 2.14, 2.06 (2s, 3H), 1.67 (s, 3H), 1.47 (s, 3H).

f. 3,5-Bis(2,3-dihydroxypropionylamino)-2,4,6-triiodo-(2-hydroxyethyl)benzene

Hydrolysis and ketal cleavage of the product of Example 61e was performed according to the method of Example 30b. After preparative HPLC the product was isolated in 88% yield.

MS (ESP, m/e): 705 ([M]$^+$, 100%).

EXAMPLE 62

3,5-Bis[N-(2-hydroxyethyl)-2,3-dihydroxypropionylamino]-2,4,6-triiodo-(2-hydroxyethyl)benzene a. 3,5-Bis[N-(2-acetoxyethyl)-2,2-dimethyl-1,3-dioxolane-4-carbamido]-2,4,6-triiodo-(2-acetoxyethyl)benzene The product of Example 61e was alkylated with 2-bromoethyl acetate according to the procedure of Example 30a. The product was isolated after preparative HPLC in 68% yield.

$^1$H NMR (CD$_3$CN): 4.25–4.45 (m, 8H), 4.05–4.20 (m, 4H), 3.77–3.95 (m, 4H), 2.06, 1.99, 1.96 (3s, 9H), 1.47, 1.45, 1.44, 1.42, 1,38, 1.27 (6s, 12H).

$^{13}$C NMR (CD$_3$CN): 170.5, 170.4, 170.3, 170.1, 148.4, 110.8, 74.0, 68.0, 61,3, 61.1, 48.6, 48.4, 25.2, 25.1, 25.0, 24.9, 20.3, 20.2.

b. 3,5-Bis-[N-(2-hydroxyethyl)-2,3-dihydroxypropionylamino]-2,4,6-triiodo-(2-hydroxyethyl)benzene Hydrolysis and ketal cleavage of the product of Example 62a followed the procedure in Example 30b. After preparative HPLC the product was isolated in a yield of 72%.

MS (ESP, m/e): 793 ([M]$^+$, 100%).

EXAMPLE 63

3-[N-(2,3-Dihydroxypropyl)-2,3-dihydroxypropionylamino]-5-(2,3-dihydroxypropionylamino)-2,4,6-triiodo-(2-hydroxyethyl)benzene a. 3-[N-(2,2-Dimethyl-1,3-dioxolane-4-methyl)-2,2-dimethyl-1,3-dioxolane-4-carbamido]-5-(2,2-dimethyl-1,3-dioxolane-4-carbamido)-2,4,6-triiodo-(2-acetoxy-ethyl)benzene N-alkylation of the product of Example 61e with 4-bromomethyl-2,2-dimethyl-1,3-dioxolane was performed according to the method of Example 26a. After work up the product was purified by preparative HPLC, and isolated in 8% yield.

MS (ESP, m/e): 942 ([M]$^+$, 100%).

b. 3-[N-(2,3-Dihydroxypropyl)-2,3-dihyroxypropionylamino]-5-(2,3-dihydroxypropionylamino)-2,4,6-triiodo-(2-hydroxyethyl)benzene Hydrolysis and ketal cleavage of the product of Example 63a were performed according to the method of Example 30b. The product was purified by preparative HPLC and isolated in 52% yield.

MS (ESP, m/e): 779 ([M]$^+$, 100%).

EXAMPLE 64

3,5-Bis-(2,3-dihydroxypropionylamino)-2,4,6-triiodo-(2,3-dihydroxy-propyl)-benzene a. 3,5-Dinitro-(3-propenyl)-benzene 3,5-Dinitroiodobenzene (5.0 g, 17.0 mmol), triphenylphosphine (0.54 g, 2.04 mmol), palladium (0) bis(dibenzylideneacetone) (0.23 g, 0.26 mmol) and copper(I) iodide (0.19 g, 1.02 mmol) were all mixed in 75 ml of dioxane. The mixture was heated to 50° C., and allyltributyltin (5.6 g, 17.0 mmol) was added. The temperature was increased to 95° C. and the mixture was stirred under an inert atmosphere. After 36 h a new portion of allyltributyltin was added and after further 36 h a second extra portion of allyltributyltin was added. After 1 week the reaction mixture was cooled to room temperature, and a solution of potassium fluoride (38 g) in water (500 ml) was added. Stirring was continued for 30 minutes. The mixture was extracted with methylene chloride (3×150 ml). The organic phases were washed with water (60 ml), dried ($Na_2SO_4$), and the solvent evaporated. The semisolid residue was purified by preparative HPLC, which gave the product as a light yellow syrup. Yield: 0.75 g (21%).

$^1$H NMR ($CDCl_3$): 8.91 (t, 1H, J=2 Hz), 8.40 (d, 2H, J=2H), 5.89–6.04 (m, 1H), 5.18–5.32 (m, 2H), 3.63 (br. d, 2H, J=7 Hz).

$^{13}$C NMR ($CDCl_3$): 169.7, 148.5, 144.5, 133.9, 128.8, 119.1, 116.9, 39.4.

b. 3,5-Dinitro-(2,3-dihydroxypropyl)benzene 3,5-Dinitro-(3-propenyl)benzene (0.10 g, 0.48 mmol) was dissolved in 20 ml of acetone and 2.5 ml of water and the solution cooled in an ice-bath. Osmium tetroxide (17 mg, 0.066 mmol), and an excess of t-butylhydroperoxide, was added. 4-Methylmorpholine N-oxide (0.12 g, 0.96 mmol) was added and the mixture was stirred at room temperature for 48 h. The reaction was then quenched by addition of a saturated solution of sodium hydrogen sulphite (60 ml). The mixture was then extracted with ethyl acetate (2×250 ml). The organic extracts were washed with water (70 ml), dried ($Na_2SO_4$), and the solvent evaporated. A white crystalline product 0.11 g (94%) resulted.

$^1$H NMR ($CD_3CN$): 8.82 (t, 1H, J=2 Hz), 8.54 (d, 2H, J=2 Hz), 3.84–3.95 (m, 1H), 3.43–3.58 (m, 2H), 2.88–3.26 (m, 4H).

$^{13}$C NMR ($CD_3CN$): 148.3, 144.2, 130.0, 116.5, 104.8, 71.8, 65.3, 38.6.

c. 3,5-Diamino-(2,3-dihydroxypropyl)benzene-hydrochloride salt 3,5-Dinitro-(2,3-dihydroxypropyl)benzene (0.12 g, 0.49 mmol) was dissolved in 25 ml of methanol. Pd/C (10%, 0.05 g) was added and the substance was hydrogenated in a Parr apparatus at 60 psi. After complete hydrogen consumption the catalyst was filtered off and the filtrate was added to hydrochloric acid (2M, 0.5 ml) The solution was evaporated to dryness. Yield: 0.12 g (100%) after pump drying. The product was used without further purification.

MS (ESP, m/e): 181 ([M]$^+$, 100%).

d. 3,5-Diamino-2,4,6-triiodo-(2,3-dihydroxypropyl)benzene 3,5-Diamino-(2,3-dihydroxypropyl)benzene-hydrochloride salt (0.72 g, 2.82 mmol) was dissolved in 25% methanol (8 ml), and hydrochloric acid (2M, 1 ml) was added. To this mixture, with stirring, was added potassium iododichloride (2.27 g, 9.59 mmol, 70% w/w). A precipitate immediately formed and was filtered off after 2 minutes. The filtercake was treated with a saturated solution of sodium hydrogen sulphite (2 ml) and filtered, washed with water (3 ml) and dried. A tan coloured product of 0.96 g (61%) resulted.

MS (ESP, m/e): 560 ([M]$^+$, 40%), 433 ([M-]$^+$, 10%), 374 ([M-I-CH(OH)CH$_2$OH]$^+$, 100%).

$^1$H NMR (DMSO-d$_6$): 5.20 (br. s, 4H), 3.73–3.94 (m, 1H), 3.58–3.62 (m, 2H), 3.26–3.35 (m, 4H).

e. 3,5-Diamino-2,4,6-triiodo-(2,3-diacetoxypropyl benzene

Acetylation of the product of Example 64d followed the general method in Example 24e. After work up the product was chromatographed on a short column of alumina with ethyl acetate as the eluent. Evaporation of the solvent gave a white crystalline residue in 70% yield.

$^1$H NMR (CDCl$_3$): 5.47–5.50 (m, 1H), 4.78 (br. s, 4H), 4.19–4.38 (m, 2H), 3.38–3.74 (m, 2H), 2.10 (s, 3H), 1.99 (s,3H).

f. 3,5-Bis-(2,2-dimethyl-1,3dioxolane-4-carbamido)-2,4,6-triiodo-(2,3-diacetoxypropyl)benzene Acylation of the product of Example 64e with 2,2-dimethyl-1,3-dioxolane-4-carboxylic chloride was effected according to the method in Example 29a. After workup, the crude product was purified by preparative HPLC and isolated in 43% yield.

MS (ESP, m/e): 901 ([M]$^+$, 100%).

g. 3,5-Bis-(2,3-dihydroxypropionylamino)-2,4,6-triiodo-(2,3-dihydroxypropyl)-benzene Hydrolysis and ketal cleavage of the product of Example 64f were performed according to the procedure of Example 29b. After workup the product was purified by preparative HPLC and isolated in 10% yield.

MS (ESP, m/e): 737 ([M]$^+$, 100%).

EXAMPLE 65

5-[N'-(2-Hydroxyethyl)-2-hydroxypropionylamino]-3-hydroxymethyl-N-(1,3,4-trihydroxybut-2-yl)-2,4,6-triiodobenzamide a. 5-[N-(2-Acetoxyethyl)-2-acetoxypropionylamino]-3-acetoxymethyl-N-(1,3,4-triacetoxybut-2-yl)-2,4,6-triiodobenzamide 5-(2-Acetoxypropionylamino)-3-acetoxymethyl-N-(1,3,4-triacetoxybut-2-yl)-2,4,6-triiodobenzamide (Example 37a) was N-alkylated using 2-bromoethyl acetate and cesium carbonate according to the procedure in Example 30a. The yield of isolated product was 82.4%.

MS (ESP, m/e): 1016 ([M]$^+$,100%).

$^1$H NMR (CDCl$_3$): 5.62 (s,2H), 5.40–5.60 (m, 1H), 4.56–5.24 (m,4H), 4.38 (t, 2H, J=7 Hz), 3.58–4.08 (m,3H), 3.52 (t,2H, J=7 Hz), 2.06, 2.09 (2s, 18H), 1.45, 1.69 (2d, 3H, $J_1$=$J_2$=7 Hz).

b. 5-[N'-(2-Hydroxyethyl)-2-hydroxypropionylamino]-3-hydroxymethyl-N-(1,3,4-trihydroxybut-2-yl)-2,4,6-triiodobenzamide The product in Example 65a was hydrolyzed according to the procedure in Example 24j. Preparative HPLC afforded the product in 58% yield.

MS (ESP, m/e): 764 ([M]$^+$, 100%).

$^1$H NMR (DMSO-d$_6$): 7.83, 7.85 (2d, 1H, $J_1$=$J_2$=5 Hz), 5.18 (s, 1H), 4.94 (s, 2H), 4.66–4.94 (m, 2H), 4.56 (s, 1H), 4.03–4.34 (m, 3H), 3.19–3.93 (m, 10H), 1.36, 1.39 (2d, 3H, $J_1$=$J_2$=7 Hz).

$^{13}$C NMR(DMSO-d$_6$): 170.2, 170.1, 169.7, 156.3, 150.6, 146.5, 146.4, 99.7, 99.3, 93.4, 92.5, 91.6, 90.6, 79.6, 79.2, 74.1, 72.5, 64.7, 62.5, 59.6, 45.9, 41,3, 18.3, 18.2.

EXAMPLE 66

5-[N'-(2,3-Dihydroxypropyl)-2,3-dihydroxypropionylamino]-3-hydroxymethyl-N-(2-hydroxyethyl)-2,4,6-triiodobenzamide a. 5-(2,3-Diacetoxypropionylamino)-3-acetoxymethyl-N-(2-acetoxyethyl)-2,4,6-triiodobenzamide The product in Example 52d was acetylated according to the general procedure in Example 24h. The resultant product was isolated in 88% yield.

MS (ESP, m/e): 844 ([M]$^+$, 100%).

b. 5-[N'-(2-Propenyl)-2,3-diacetoxypropionylamino]-3-acetoxymethyl-N-(2-acetoxyethyl)-2,4,6-triiodobenzamide 5-(2,3-Diacetoxypropionylamino)-3-acetoxymethyl-N-(2-acetoxyethyl)-2,4,6-triiodobenzamide (8.65 g, 10.3 mmol) was dissolved in dimethyl sulfoxide (10 ml) at room temperature. Cesium carbonate (3.88 g, 11.8 mmol) was added and after stirring at room temperature for 15 min, the mixture was cooled in an ice bath. Allyl bromide (2.10 g, 17.3 mmol) was added dropwise and the mixture was then stirred for 17 h at room temperature. The reaction mixture was transferred onto aqueous hydrochloric acid (0.1 M, 300 ml). The formed precepitate was filtered off, redissolved in methylene chloride (150 ml) and washed with water (5×100 ml). The organic phase was dried (Na$_2$SO$_4$), and the solvent evaporated. Yield: 8.73 g (96%).

MS (ESP, m/e): 885 ([M]$^+$, 100%).

$^1$H NMR (CDCl$_3$): 6.20–6.36 (m, 1H), 5.73–5.92 (m, 1H), 5.54 (d, 2H, J=5 Hz), 5.08–5.35 (m, 2H), 4.15–4.80 (m, 7H), 3.67–3.78 (m, 2H), 1.92, 1.95, 1.96, 2.06, 2.07, 2.08, 2.10, 2.12, 2.15 (9s, 12H).

c. 5-[N'-(2,3-Dihydroxypropyl)-2,3-diacetoxypropionylamino]-3-acetoxymethyl-N-(2-acetoxyethyl)-2,4,6-triiodobenzamide 5-[N'-(2-Propenyl)-2,3-diacetoxypropionylamino]-3-acetoxymethyl-N-(2-acetoxy-ethyl)-2,4,6-triiodobenzamide (8.73 g, 9.90 mmol) was dissolved in acetone (360 ml) and water (40 ml) and the solution was cooled in an ice-bath. Osmium tetroxide (110 mg, 0.43 mmol), and an excess of t-butylhydroperoxide was added. 4-Methyl-morpholine N-oxide (2.32 g, 19.8 mmol) was added and the mixture was stirred at room temperature for 24 h. The reaction was then quenched by addition of a saturated solution of sodium hydrogen sulphite (120 ml). The acetone was evaporated, and the residue was extracted with ethyl acetate (2×70 ml). The organic extracts were washed with water (50 ml), dried (NaSO$_4$), and the solvent was evaporated. The residue was chromatographed on a column of silica using a mixture of ethyl acetate/acetone (1/1) as the eluent yield: 5.82 g (64%).

MS (ESP, m/e): 919 ([M]$^+$, 100%).

$^1$H NMR (DMSO-d$_6$): 8.65–8.90 (m, 1H), 5.95–6.10 (m, 1H), 5.42–5.50 (br. s, 2H), 5.00–5.30 (s, 1H), 3.70–4.85 (m, 10H), 3.40–3,58 (m, 2H), 1.92, 2.00, 2.01, 2.06 (4s, 12H).

d. 5-[N'-(2,3-Dihydroxypropyl)-2,3-dihydroxypropionylamino]-3-hydroxymethyl-N-(2-hydroxyethyl)-2,4,6-triiodobenzamide Hydrolysis of the product in Example 66c was performed according to the general procedure given in Example 24j. Preparative HPLC afforded the product in 54% yield.

MS (ESP, m/e): 751 ([M]$^+$, 100%).

$^1$H NMR (DMSO-d$_6$): 8.18–8.58 (m, 1H), 6.38 (s, 1H), 5.13–5.28 (m, 1H), 4.80–5.14 (m, 3H), 4.46–4.83 (m, 3H), 3.38–4.45 (m, 6H), 3.15–3.38 (m, 6H).

$^{13}$C NMR (DMSO-d$_6$): 170.0, 169.7, 147.9, 145.3, 144.2, 108.6, 100.4, 98.8, 98.7, 97.9, 92.2, 81.9, 74.3, 69.2, 64.0, 63.8, 59.6, 59.2, 46.9, 41.9, 41.7 .

EXAMPLE 67

5-(hydroxyacetamido)-3-hydroxymethyl-N,N-bis-(2,3-dihydroxy-propyl)-2,4,6-triiodobenzamide a. 5-Amino -3-acetoxymethyl-N,N-bis-(2,3-dihydroxypropyl)-2,4,6-triiodo-benzamide 5-Amino-3-acetoxymethyl-2,4,6-triiodobenzoyl chloride (19.9 g, 32.9 mmol) was dissolved in dioxane (45 ml) and triethylamine (3.32 g, 32.9 mmol) was added. To this solution was added bis-(2,3-dihydroxypropyl)amine (5.43 g, 32.9 mmol), and the mixture was stirred at 90° C. for 17 h. After cooling to room temperature, acetonitrile (150 ml), water (70 ml), and a strongly acidic ion exchange resin (Amberlyst 15, 60 g) were added to bring the pH to 4. After stirring at room temperature for 20 min, the resin was filtered off and the filtrate was evaporated to dryness. The semicrystalline dark residue was filtered through a short column of silica using a mixture of methylene chloride and methanol (70/30) as the eluent. The solvent was evaporated and 22.4 g (93%) of a tan coloured crystalline product was obtained. This product was acetylated without further purification.

MS (ESP, m/e): 734 ([M]$^+$, 100%).

$^1$H NMR (DMSO-d$_6$): 5.21–5.76 (m, 4H), 4.48–5.20 (m,5H), 3.50–4.38 (m, 5H), 2.65–3.38 (m, 4H), 2.02, 2.05 (2s, 3H).

$^{13}$C NMR (DMSO-d$_6$): 171.7, 170.4, 170.2, 148.3, 148.1, 147.6, 145.1, 144.8, 87.7, 87.6, 82.3, 80.7, 80.5, 74.6, 70.2, 69.9, 69.4, 67.2, 67.1, 64.6, 63.7, 53.9, 53.7, 50.6, 50.4, 50.1, 49.9, 45.5, 21.0, 20.9, 20.5.

b. 5-Amino-3-acetoxymethyl-N,N-bis-(2,3-diacetoxypropyl)-2,4,6-triiodobenzamide

The product in Example 67a was acetylated according to the general procedure in Example 24h, and isolated in 60% yield.

MS (ESP, m/e): 902 ([M]$^+$, 100%).

$^1$H NMR (CDCl$_3$): 5.30–5.58 (m, 1H), 5.49 (s, 2H), 5.16–5.31 (m, 1H), 5.15 (s, 2H), 3.95–4.58 (m, 5H), 3.12–3.69 (m, 3H), 2.03, 2.06, 2.08, 2.10 (4s, 15H).

$^{13}$C NMR (CDCl$_3$): 171.7, 170.4, 170.3, 170.0, 169.8, 147.9, 147.8, 146.7, 141.1, 140.9, 140.7, 136.5, 88.9, 87.5, 81.0, 80.0, 79.7, 78.3, 70.1, 69.9, 69.8, 69.2, 68.4, 49.7, 48.9, 46.4, 46.0, 45.6, 21.5, 21.2, 21.0, 20.7, 20.6, 20.5, 20.4.

c. 5-Acetoxyacetamido-3-acetoxymethyl-N,N-bis-(2,3-diacetoxypropyl)-2,4,6-triiodobenzamide The compound in Example 67b was N-acylated using acetoxyacetyl chloride according to the procedure given in Example 24i. The product was isolated in 87% yield.

MS (ESP, m/e): 1002 ([M]$^+$, 100%).

$^1$H NMR (CDCl$_3$): 8.01, 8.48, 8.56 (3s, 1H), 5.56 (br.s, 2H), 5.08–5.48 (m, 2H), 4.78 (s, 2H), 3.84–4.66 (m, 4H), 2.88–3.80 (m, 4H), 2.06, 2.08, 2.10, 2.16, 2.25 (5s, 18H).

$^{13}$C NMR (CDCl$_3$): 171.6, 170.5, 170.3, 170.1, 170.0, 169.6,169.4, 165.6, 165.3, 160.9, 147.8, 146.2, 142.5, 142.1, 107.5, 98.2, 97.9, 96.9, 96.1, 70.1, 70.0, 69.5, 69.1, 68.8, 68.5, 63.5, 63.2, 62.7, 62.2, 50.1, 49.9, 48.9, 46.7, 46.4, 45.8, 45.7, 21.5, 21.3, 20.8, 20.7, 20.6, 20.4.

d. 5-Hydroxyacetamido-3-hydroxymethyl-N,N-bis-(2,3-dihydroxypropyl)-2,4,6-triiodobenzamide The product in Example 67c was hydrolyzed according to the general procedure given in Example 24j. After HPLC purification the product was isolated in 67% yield.

MS (ESP, m/e): 750 ([M]$^+$, 100%).

$^1$H NMR (DMSO-d$_6$): 9.73, 9.76, 9.82, 9.97 (4s, 1H), 5.65, 5.73 (2d, 1H, J$_1$=J$_2$=4 Hz), 5.21 (t, 1H, J=4 Hz), 4.99, 5.07 (2t, 1H, J$_1$=J$_2$=4 Hz), 4.93 (s, 2H), 4.02–4-65 (m, 3H), 3.99 (s, 2H), 3.70–3.87 (m, 2H), 2.90–3.50 (m, 8H).

$^{13}$C NMR (DMSO-d$_6$): 171.1, 171.0, 170.4, 148.5, 146.5, 146.4, 143.6, 143,5, 143.4, 106.7, 99.5, 99.3, 97.9, 74.6, 74.5, 70.6, 70.3, 69.9, 69.7, 69.4, 64.5, 64.4, 63.7, 63.6, 61.9, 54.0, 53.7, 53,5, 50.9, 50.3.

EXAMPLE 68

5-[N'-(2-Hydroxyethyl)-hydroxyacetamido]-3-hydroxymethyl-N,N-bis-(2,3-dihydroxypropyl)-2,4,6-tiiodobenzamide a. 5-[N'-(2-Acetoxyethyl)-acetoxyacetamido]-3-acetoxymethyl-N,N-bis-(2,3-diacetoxypropyl)-2,4,6-triiodobenzamide The product in Example 67c was N-alkylated using 2-bromoethyl acetate and cesium carbonate according to the procedure given in Example 25a. The product was isolated in 93% yield.

MS (ESP, m/e): 1090 ([M]$^+$, 100%).

$^1$H NMR (CDCl$_3$): 5.90 (s, 2H), 5.08–5.58 (m, 2H), 4.28–4.60 (m, 8H), 3.25 (m, 4H), 3,50 (t, 2H, J=6 Hz), 2.08, 2.09, 2.12, 2.13 (4s, 21H).

$^{13}$C NMR (CDCl$_3$): 170.5, 169.8, 166.4, 149.7, 147.4, 147.0, 144.7, 144.6, 109.8, 108.0, 99.6, 98.5, 97.6, 70.0, 68.9, 68.7, 63.8, 63,5, 62.6, 62.2, 61.8, 61.1, 49.1, 49.0, 48.7, 46.9, 28.7, 21,3, 21.0, 20.9, 20.7, 20.6.

b. 5-[N'-(2-Hydroxyethyl)-hydroxyacetamido]-3-hydroxymethyl-N,N-bis-(2,3-dihydroxypropyl)-2,4,6-triiodobenzamide The product from Example 68a was hydrolyzed according to the procedure given in Example 24j and, after HPLC purification, the compound was isolated in 72% yield.

MS (ESP, m/e): 795 ([M]$^+$, 100%).

$^1$H NMR (DMSO-d$_6$): 5.14–5.26 (m, 1H), 4.96–5.08 (m, 1H), 4.94 (s, 2H), 4.56–4.90 (m, 2H), 4.26–4.48 (m, 1H), 4.05 (br. s, 1H), 3.76–3.88 (m, 1H), 2.86–3.76 (m, $^{13}$C NMR (DMSO-d$_6$): 171.3, 171.2, 171.0, 170.8, 149.9, 149.7, 148.0, 147.9, 147.8, 146.0, 107.7, 107.6, 100.8, 100.5, 100.3, 100.1, 99.9, 74.8, 74.7, 70.6, 70.0, 69.3, 69.2, 64.4, 64.3, 63,5, 61.5, 61.4, 58.5, 58.3, 54.2, 54.1, 53.8, 51.7, 51.1, 50.6, 50.3.

EXAMPLE 69

5-(2-Hydroxypropionylamino)-3-hydroxymethyl-N,N-bis-(2,3-dihydroxypropyl)-2,4,6-triiodobenzamide a. 5-(2-Acetoxypropionylamino)-3-acetoxymethyl-N,N-bis-(2,3-diacetoxypropyl)-2,4,6-triiodobenzamide The product from Example 67b was acylated using 2-acetoxypropionyl chloride according to the procedure given in Example 27a. The product was isolated in 92% yield as a foam.

MS (ESP, m/e): 1016 ([M]$^+$, 100%).

$^1$H NMR (CDCl$_3$): 8.73, 8.80, 8.83, 8.89 (4s, 1H), 5.52 (s, 2H), 5.39 (q, 2H, J=7 Hz), 5.15–5.30 (m, 1H), 3.82–4.66 (m, 4H), 3.04–3.83 (m, 4H), 2.07, 2.08, 2.20 (3s, 18H), 1.57, 1.66 (2d, 3H, J$_1$=J2=6 Hz).

$^{13}$C NMR (CDCl$_3$): 171.7, 170.4, 170.3, 170.1, 169.8, 169.7, 169.6, 168.6, 168.5, 168.2, 161.0, 146.0, 143.2, 143.0, 142.8, 142.6, 142.2, 108.2, 107.2, 98.3, 98.2, 97.6, 97.4, 96.8, 95.8, 70.2, 70.0, 69.9, 69.4, 69.2, 68.8, 68.7, 68.2, 63,5, 62.6, 62.2, 50.2, 49.8, 46.7, 45.7, 21.4, 21.2, 21.1, 21.0, 20.7, 20.5, 20.4, 17.6, 17.5.

b. 5-(2-Hydroxypropionylamino)-3-hydroxymethyl-N,N-bis-(2,3-dihydroxypropyl)-2,4,6-triiodobenzamide The product from Example 69a was hydrolyzed according to the general procedure given in Example 24j. After two HPLC purifications the product was isolated in 27% yield.

MS (ESP, m/e): 764 ([M]$^+$, 100%).

$^1$H NMR (DMSO-d$_6$): 9.66, 9.68, 9.73, 9.88 (4s, 1H), 5.60–5.72 (m, 1H), 5.20 (t, 1H, J=5 Hz), 4.95–5.08 (m, 1H, J=5 Hz), 4.94 (s, 2H), 4.55–4.63 (m, 1H), 4.28–4.53 (2m, 1H), 4.00–4.23 (m, 2H), 3.70–3.90 (m, 2H), 2.89–3.53 (m, 9H), 1.37(d, 3H, J=6 Hz).

$^{13}$C NMR (DMSO-d$_6$): 172.5, 171.1, 148.4, 146.4, 146.3, 143,5, 143.4, 106.7, 99.2, 99.1, 97.8, 97.7, 74.6, 70.5, 70.3, 69.9, 69.8, 69.3, 67.6, 64.5, 64.4, 63.6, 53.9, 53.7, 50.5, 50.3, 21.0.

EXAMPLE 70

5-(3-Hydroxy-2-oxo-1-piperidinyl)-3-hydroxymethyl-N,N-bis-(2,3-dihydroxypropyl)-2,4,6-triiodobenzamide a. Tetrahydrofuran-2-carbonyl chloride Tetrahydro-2-furoic acid (75 g, 0.65 mol) and oxalyl chloride (205.6 g, 1.62 mol) were mixed and stirred at room temperature for 18 h. The volatiles were removed and the residue was distilled in vacuo to give 79 g (91%) of the product. B.p. 75–77° C. (23 mm Hg).

$^1$H NMR (CDCl$_3$): 4.73 (dd, 1H, J$_1$=8.6 Hz, J$_2$=5.3 Hz), 3.94–4.08 (m, 2H), 2.29–2.46 (m, 1H), 2.17–2.29 (m, 1H), 1.93–2.04 (m, 2H).

b. Benzyl tetrahydrofuran-2-carboxylate

To a cold solution of benzyl alcohol (57.2 g, 0.53 mol) in dry ether (1l) and pyridine (107 ml) tetrahydrofuran-2-carbonyl chloride (78.7 g, 0.58 mol) was added dropwise, and the solution stirred for further 45 min. at this temperature. The mixture was then filtered and the filtrate washed with diluted hydrochloric acid (0.1 M, 150 ml), water (2×70 ml) and sodium hydrogen carbonate (5%, 70 ml). After drying (NaSO$_4$) the solvent was evaporated and the residue distilled in vacuo to give 92 g (84%) of the product as a colourless oil. B.p. 118–120° C.

$^1$H NMR (CDCl$_3$): 7.30–7.40 (m, 5H), 5.20 (s, 2H), 4.46–4.54 (m, 1H), 3.87–4.08 (m, 2H), 1.82–2.32 (m, 4H).

c. Benzyl 2-acetoxy-5-chloropentanoate

Freshly fused zinc chloride (0.21 g, 1.57 mmol) and acetyl chloride (209 g, 2.7 mol) were mixed. Benzyl tetrahydrofuran carboxylate (91.6 g, 0.44 mol) was then added dropwise to this suspension. The mixture was heated to reflux temperature for 18 h with efficient stirring. The volatiles were distilled off and the residue was taken up in ether (1 l) and washed with aqueous sodium hydrogen carbonate (5%, ca 250 ml). The organic phase was dried (Na$_2$SO$_4$) and evaporated to give an oil which was chromatographed on a short column of silica gel using ethylacetate/heptane (1/4) as the eluent. Evaporation of the solvent gave a yellow oil, which was distilled in vacuo to give 106 g (85%) of the product.

B.p. 180–185° C. (0.8–0.9 mm Hg).

$^1$H NMR (CDCl$_3$): 7.34–7.37 (m, 5H), 5.19 (dd, 2H, J$_1$=12.5 Hz, J$_2$=7 Hz), 5.08 (dd, 1H, J$_1$=5 Hz, J$_2$=6 Hz), 3.53 (t, 2H, J=7 Hz), 2.14 (s, 3H), 1.97–2.09 (m, 2H), 1.80–1.92 (m,2H).

d. 2-Acetoxy-5-chloropentanoic acid

Benzyl 2-acetoxy-5-chloropentanoate (52.6 g, 0.19 mol) was dissolved in ethyl acetate (350 ml) and acetic acid (25 ml) and hydrogenated at 10 psi in a Parr apparatus in the presence of a Pd/C catalyst (5%, 2.5 g). After completion, the catalyst was filtered off and the volatiles were evaporated. The residue was dried in vacuo ( 1 mm Hg, 100° C.), and 35 g (98%) of the crude product was isolated and used without further purification.

$^1$H NMR (CDCl$_3$): 11.37 (s, 1H), 5.00–5.07 (m, 1H), 3.56 (t, 2H, J=6 Hz), 2.14(s, 3H), 1.86–2.08 (m, 4H).

e. 2-Acetoxy-5-chloropentanoyl chloride

Oxalyl chloride (114 g, 0.90 mol) was added to 2-acetoxy-5-chloropentanoic acid g, 0.37 mol). The mixture was stirred at room temperature for 15 h. The volatiles were evaporated and the oily residue was distilled in vacuo to give 75 g (96%) of product. B.p. 93–95° C. (2 mm Hg).

$^1$H NMR (CDCl$_3$): 5.17 (dd, 1H, J$_1$=5 Hz, J$_2$=8 Hz), 3.59 (t, 2H, J=6 Hz), 2.18 (s, 3H), 2.04–2.17 (m, 2H), 1.88–1.99 (m, 2H).

f. 5-(2-Acetoxy-5-chloropentanoylamino)-3-acetoxymethyl-N,N-bis-(2,3-dihydroxypropyl)-2,4,6-triiodobenzamide 5-Amino-3-acetoxymethyl-N,N-bis-(2,3-diacetoxypropyl)-2,4,6-triiodobenzamide, 6.85 mmol) was dissolved in dry N,N-dimethylacetamide (10 ml) and the mixture was cooled in an ice-bath. 2-Acetoxy-5-chloropentanoyl chloride (4.36 g, mmol) was then added dropwise. The mixture was stirred at room temperature for 24 h, and then added slowly to aqueous sodium hydrogen carbonate (5%, 600 ml) with efficient stirring. A precepitate was formed and filtered off, redissolved in methylene chloride (250 ml) which was washed with water (6×70 ml), dried Na$_2$SO$_4$) and concentrate in vacuo. The residue was chromatographed on a column of silica gel using heptane/ethyl acetate (3/7) as the eluent Yield: 7.30 g (97%).

MS (ESP, m/e): 1078 ([M]$^+$, 100%).

$^1$H NMR (CDCl$_3$): 5.55 (s, 2H), 5.39–5.49 (m, 1H), 5.16–5.34 (m, 6H), 3.60 (t, 2H, J=6 Hz), 3.15–3.80 (m, 4H), 2.07, 2.09, 2.11, 2.17, 2.26 (5s, 18H), 1.87–2.20 (m, 4H).

$^{13}$C NMR (CDCl3): 170.5, 170.3, 170.0, 169.7, 167.7, 148.0, 143.2, 142.6, 142.1, 107.2, 99.0, 98.3, 97.8, 96.7, 96.08 73.2, 73.1, 70.0, 69.6, 69.2, 68.9, 68.5, 63,5, 62.7, 62.3, 50.2, 49.9, 48.9, 44.4, 29.1, 29.0, 28.3, 28.2, 21,3, 21.1, 20.7, 20.6.

g. 5-(3-Acetoxy-2-oxo-1-piperidinyl)-3-acetoxymethyl-N,N-bis-(2,3-diacetoxy-propyl)-2,4,6-triiodobenzamide The product in Example 70f (7.30 g, 6.77 mmol) was dissolved in dimethyl sulfoxide (10 ml) at room temperature and cesium carbonate (2.20 g, 6.77 mmol) was added. The mixture was stirred at room temperature for 15 h, and was then added slowly into diluted aqueous hydrochloric acid (0.05 M, 150 ml). The precepitate formed was filtered off, redissolved in ethyl acetate (70 ml), which was washed with water (5×50 ml). After drying (Na$_2$SO$_4$) the solvent was evaporated to give 6.70 g (95%) of a crystalline product.

MS (ESP, m/e): 1042 ([M]$^+$, 100%).

$^1$H NMR (CDCl$_3$): 5.52 (s, 2H), 5.36–5.45 (m, 1H), 4.92–5.38 (m, 2H), 436–4.60 (m, 1H), 3.92–4.37 (m, 3H), 3.25–3.80 (m, 6H), 2.08, 2.09, 2.10, (4s, 18H), 1.87–2.30 (m, 4H).

$^{13}$C NMR (CDCl$_3$): 171.2, 171.1, 170.5, 170.1, 169.9, 169.8, 1 65.9, 165.5, 148.9, 147.5, 143.9, 143.7, 143.6, 105.2, 104.7, 98.3, 98.2, 98.0, 70.2, 69.7, 69.2, 69.1, 69.0, 68.8, 63.6, 63,5, 62.6, 62.4, 60.4, 50.1, 49.8, 49.5, 48.6, 48.2, 46.8, 46.7, 46.5, 45.9, 44.2, 26.7, 21.5, 21,3, 21.2, 21.0, 20.7, 20.6.

h. 5-(3-Hydroxy-2-oxo-1-piperidinyl)-3-hydroxymethyl-N,N-bis-(2,3-dihydroxypropyl)-2,4,6-triiodobenzamide The product in Example 70g was hydrolyzed according to the general procedure given in Example 24j. After HPLC purification the product was isolated in 51% yield.

MS (ESP, m/e): 790 ([M]$^+$, 100%).

$^1$H NMR (DMSO-d$_6$): 5.52 (s, 1H), 5.03, 5.12, 5.24 (3s, 2H), 4.91 (s, 2H), 4.42, 4.60 (2s, 3H), 3,58–4.11 (m, 4H), 2.82–3.56 (m, 10H), 1.75–2.20 (m, 3H).

$^{13}$C NMR (DMSO-d$_6$): 170.9, 170.8, 169.8, 149.1, 147.5, 147.3, 147.0, 146.9, 105.7, 104.8, 98.8, 98.7, 98.1, 98.0, 97.6, 74.3, 70.8, 69.9, 69.4, 69.3, 67.8, 64.5, 64.4, 63.4, 63.3, 54.0, 50.3, 48.4, 48.3, 28.8, 20.1, 19.9, 19.8.

EXAMPLE 71

3,5-Bis-(Hydroxyacetamido)-2,4,6-triiodo-(2,3-dihydroxypropyl)benzene a. 3,5-Bis-(Acetoxyacetamido)-2,4,6-triiodo-(2,3-diacetoxypropyl)benzene The product in Example 64e, 3,5-diamino-2,4,6-triiodo-(2,3-diacetoxypropyl)benzene was acylated using acetoxyacetyl chloride according to the general procedure in Example 24i. After chromatography on silica gel using methylene chloride/acetonitrile (3/1) as the eluent the product was isolated in 64% yield.

MS (ESP, m/e): 844 ([M]$^+$, 100%).

b. 3,5-Bis-(Hydroxyacetamido)-2,4,6-triiodo-(2,3-diacetoxypropyl)benzene

The product in Example 71a was hydrolyzed according to the general procedure given in Example 24j. After HPLC purification the product was isolated in 67% yield.

MS (ESP, m/e): 676 ([M]$^+$, 100%).

$^1$H NMR (DMSO-d$_6$): 9.83, 9.75 (2s, 2H), 5.60 (s, 4H), 4.65, 4.63 (2s, 4H), 3.98 (d, 2H), 3.82–3.96 (m, 1H), 3.38–3,50 (m, 2H).

EXAMPLE 72

5-Hydroxyacetamido-3-[N-(2-hydroxyethyl)-hydroxyacetamido]-2,4,6-triiodo-(2,3-dihydroxypropyl)benzene a. 5-Acetoxyacetamido-3-[N-(2-acetoxyethyl)-acetoxyacetamido]-2,4,6-triiodo-(2,3-diacetoxypropyl)benzene and 3,5-bis-[N,N'-(2-acetoxyethyl)-acetoxyacetamido]-2,4,6-triiodo-(2,3-diacetoxypropyl)benzene 3,5-Bis-(acetoxyacetamido)-2,4,6-triiodo-(2,3diacetoxypropyl)benzene, Example 71a, was alkylated using 2-bromoethyl acetate in the presence of cesium carbonate according to the general procedure given in Example 25a. The reaction product was purified by HPLC to give the two products.

5-Acetoxyacetamido-3-[N-(2-acetoxyethyl)-acetoxyacetamido]-2,4,6-triiodo-(2,3-diacetoxypropyl)benzene was isolated in 12% yield.

MS (ESP, m/e): 930 ([M]$^+$, 100%).

3,5-Bis-[N,N'-(2-acetoxyethyl)-acetoxyacetamido]-2,4,6-triiodo-(2,3-diacetoxypropyl)benzene was isolated in 33% yield.

MS (ESP, m/e): 1016 ([M]$^+$, 100%).

b. 5-Hydroxyacetamido-3-[N-(2-hydroxyethyl)-hydroxyacetamido]-2,4,6-triiodo-(2,3-dihydroxypropyl)benzene 5-Acetoxyacetamido-3-[N-(2-acetoxyethyl)-acetoxyacetamido]-2,4,6-triiodo-(2,3-diacetoxypropyl)benzene, Example 72a, was hydrolyzed according to the general procedure given in Example 24j. After HPLC purification the product was isolated in 71% yield.

MS (ESP, m/e): 720 ([M]$^+$, 100%).

$^1$H NMR (D$_2$O): 4.65 (s, 4H), 4.39 (s, 1H), 3.95–4.10 (m, 1H), 3.37–3.80 (m, 8H).

EXAMPLE 73

3,5-Bis-[N,N'-(2-hydroxyethyl)-hydroxyacetamido]-2,4,6-triiodo-(2,3-dihydroxypropyl)benzene The product from Example 72a, 3,5-bis-[N,N'-(2-acetoxyethyl)-acetoxyacetamido]-2,4,6-triiodo-(2,3-diacetoxypropyl)benzene was hydrolyzed according to the procedure given in Example 24j. HPLC purification afforded the product in 71% yield.

MS (ESP, m/e): 764 ([M]+, 100%).

¹H NMR (D₂O): 4.65 (s, 4H), 3.96–4.10 (m, 1H), 3.38–3.85 (m, 12H).

EXAMPLE 74

5-Hydroxyacetamido-3-[N-(2,3-dihydroxypropyl)-hydroxyacetamido]-2,4,6-triiodo-(2,3-dihydroxypropyl)benzene a. 5-Acetoxyacetamido-3-[N-(2,2-dimethyl-1,3-dioxolane-4-methyl)-acetoxyacetamido]-2,4,6-triiodo-(2,3-diacetoxypropyl)benzene and 3,5-bis-[N,N'-(2,2-dimethyl-1,3-dioxolane-4-methyl)-acetoxyacetamido]-2,4,6-triiodo-(2,3-diacetoxypropyl)benzene 3,5-Bis-(acetoxyacetamido)-2,4,6-triiodo(2,3-diacetoxypropyl)benzene, Example 71a was alkylated using 4-bromomethyl-2,2-dimethyl-1,3-dioxolane in the presence of cesium carbonate according to the procedure given in Example 26a. The reaction product was purified by HPLC on a column of silica gel using methylene chloride/acetonitrile (a 95/5 to 50/50 gradient) as the eluent to give the two products. 5-Acetoxyacetamido-3-[N-(2,2-dimethyl-1,3dioxolane-4-methyl)-acetoxyacetamido-2,4,6-triiodo-(2,3-diacetoxypropyl)benzene was isolated in 38% yield.

MS (ESP, m/e): 958 ([M]+, 100%).

¹H NMR (CDCl₃): 7.97, 8.00, 8.10 (3s, 1H), 5.45–5.65 (m, 1H), 4.10–4.62 (m, 6H), 3.27–4.05 (m, 5H), 1.95, 2.00, 2.10, 2.13, 2.15, 2.26 (6s, 12H), 1.27, 1.32 (2s, 6H).

3,5-Bis-[N,N'-(2,2-dimethyl-1,3dioxolane-4-methyl)-acetoxyacetamido]-2,4,6-triiodo-(2,3-diacetoxypropyl)benzene was isolated in 45% yield.

MS (ESP, m/e): 1072 ([M]+, 100%).

¹H NMR (CDCl₃): 5.45–5.62 (m, 1H), 2.98–5.05 (m, 1H), 1.93, 1.95, 2.11, 2.15 (4s, 12H), 1.20, 1.24, 1.27, 1.32, 1.56 (5s, 12H).

b. 5-Hydroxyacetamido-3-[N-(2,3-dihydroxypropyl)-hydroxyacetamido]-2,4,6-triiodo-(2,3-dihydroxypropyl)benzene 5-Acetoxyacetamido-3-[N-(2,3-diacetoxypropyl)-acetoxyacetamido]-2,4,6-triiodo-(2,3-diacetoxypropyl)benzene, Example 74a, was hydrolyzed according to the general procedure given in Example 24j. After HPLC purification the product was isolated in 73% yield.

MS (ESP, m/e): 751 ([M]+, 100%), 768 ([M+H₂]+, 12%).

EXAMPLE 75

3,5-Bis-[N,N'-(2,3-dihydroxypropyl)-hydroxyacetamido]-2,4,6-triiodo-(2,3-dihydroxypropyl)benzene 3,5-Bis-[N,N'-(2,3-diacetoxypropyl)-acetoxyacetamido]-2,4,6-triiodo-(2,3-diacetoxy-propyl)benzene, Example 74a, was hydrolyzed according to the general method given in Example 24j. The product was purified by HPLC and isolated in 37% yield.

MS (ESP, m/e): 825 ([M]+, 100%), 807 ([M-H₂O]+, 7%).

EXAMPLE 76

5-(2,3-Dihydroxypropionylamino)-3-[N-(2-hydroxyethyl)-2,3-dihydroxypropionylamino]-2,4,6-triiodo-(2,3-dihydroxypropyl)benzene a. 3,5-Bis-(2,3-diacetoxypropionylamino)-2,4,6-triiodo-(2,3-dihydroxypropyl)benzene 3,5-Bis-(2,3-dihydroxypropionylamino)-2,4,6-triiodo-(2,3-dihydroxypropyl)benzene (Example 64g) was acetylated according to the general method given in Example 24e. After aqueous workup, the product was chromatographed on a short column of alumina using ethyl acetate as the eluent. Evaporation of the solvent gave a white crystalline product in 90% yield.

MS (ESP, m/e): 986 ([M]⁻, 100%).

¹H NMR (CDCl₃): 8.24, 8.06 (2s, 2H), 5.60–5.67 (m, 2H), 5.48–5.62 (m, 1H), 4.59–4.71 (m, 2H), 4.41–4.51 (m, 2H), 4.31–4.39 (m, 1H), 4.15–4.23 (m, 1H), 3.75–3.95 (m, 1H), 3.45–3.64 (m, 1H), 2.24, 2.08, 1.98, 1.93 (4s, 18H).

5-(2,3-Diacetoxypropionylamino)-3-[N-(2-acetoxyethyl)-2,3-diacetoxypropionylamino]-2,4,6-triiodo-(2,3-diacetoxypropyl)benzene 3,5-Bis-(2,3-diacetoxypropionylamino)-2,4,6-triiodo-(2,3-diacetoxypropyl)benzene g, 0.67 mmol) was dissolved in dimethyl sulfoxide (6 ml) at room temperature. Cesium carbonate (0.42 g, 1.28 mmol) was added and the mixture was stirred, still at room temperature, for 0.5 h. The mixture was cooled in an ice bath and bromoethyl acetate (0.23 ml, 2.08 mmol) was added. The mixture was stirred at room temperature for 36 h and then transferred to aqueous hydrochloric acid (0.05 M, 50 ml). The formed precepitate was filtered off, redissolved in methylene chloride (100 ml) and washed with water (3×40 ml). The organic phase was dried (Na₂SO₄), and the solvent was evaporated. The sirup left was dissolved in ethyl acetate (25 ml) and filtered through a small pad of silica. The solvent was evaporated and the residue was purified by preparative HPLC to give two compounds:

5-(2,3-Diacetoxypropionylamino)-3-[N-(2-acetoxyethyl)-2,3-diacetoxypropionylamino]-2,4,6-triiodo-(2,3-diacetoxypropyl)benzene was isolated in 26% yield (0.18 g).

MS (ESP, m/e): 1074 ([M]+, 100%).

¹H NMR (CDCl₃): 8.35, 8.30, 8.09, 7.95 (4s, 1H), 5.27–5.88 (m, 3H), 3.49–4.92 (m, 12H), 2.27, 2.10, 2.01, 1.97, 1.94 (5s, 21H).

3,5-Bis-[N,N'-(2-acetoxyethyl)-2,3-diacetoxypropionylamino]-2,4,6-triiodo-(2,3-diacetoxypropyl)benzene was isolated in 18% yield (0.14 g).

MS (ESP, m/e): 1160 ([M]+, 100%).

¹H NMR(CDCl₃): 5.24–6.01 (m, 3H), 3.52–4.95 (m, 16H), 2.17, 2.12, 2.04, 1.98, 1.91 (5s, 24H).

5-(2,3-Dihydroxypropionylamino)-3-[N-(2-hydroxyethyl)-2,3-dihydroxypropionylamino]-2,4,6-triiodo-(2,3-dihydroxypropyl)benzene 5-(2,3-Diacetoxypropionylamino)-3-[N-(2-acetoxyethyl)-2,3-diacetoxypropionylamino]-2,4,6-triiodo-(2,3-diacetoxypropyl)benzene was hydrolyzed according to the general procedure given in Example 24j. After HPLC purification the product was isolated in 22% yield.

MS (ESP, m/e): 780 ([M]+, 100%).

EXAMPLE 77

3,5-Bis-[N,N'-(2-hydroxyethyl)-2,3-dihydroxypropionylamino]-2,4,6-triiodo-(2,3-dihydroxypropyl)benzene 3,5-Bis-[N,N'-(2-acetoxyethyl)-2,3-diacetoxypropionylamino]-2,4,6-triiodo-(2,3-diacetoxypropyl)benzene (Example 76b) was hydrolyzed according to the general method given in Example 24j. After HPLC purification the product was isolated in 40% yield.

MS (ESP, m/e): 824 ([M]+, 100%).

EXAMPLE 78

3,5-Bis-(2,3-dihydroxypropyloxy)-2,4-diiodobenzyl alcohol a. 2-Propenyl 3,5-bis-(2-propenyloxy)-benzoate 3,5-Dihydroxybenzoic acid (15.0 g, 97.3 mmol) and potassium carbonate (44.0 g, mol) were mixed in N,N-dimethylformamide (60 ml) and heated to 80° C. Allyl bromide (42.0 g, 0.35 mol) was added dropwise during 1 h and efficient stirring was continued for 24 h. The reaction mixture was then evaporated to a semisolid residue, which was treated with chloroform (500 ml) and filtered. The filtrate was washed with water (3×150 ml), dried ($Na_2SO_4$) and filtered through a short column of alumina. Evaporation of the solvent gave 23.1 g (87%) of the product as a colorless oil.

$^1$H NMR ($CDCl_3$): 7.22 (d, 2H, J=2 Hz), 6.69 (t, 1H, J=2 Hz), 5.95–6.12 (m, 3H), 5.34–5.47 (m, 3H), 5.23–5.33 (m, 3H), 4.80 (d, 2H, J=5 Hz), 4.55 (d, 4H, J=5 Hz).

b. 3,5-Bis-(2-propenyloxy)-benzyl alcohol

2-Propenyl-3,5-bis-(2-propenyloxy)-benzoate (23.1 g, 84.2 mmol) was dissolved in dry diethyl ether (250 ml) and added dropwise at 0° C. to a suspension of lithium aluminium hydride (3.45 g, 91.0 mmol) in dry diethyl ether (200 ml). The mixture was stirred at room temperature for 16 h and ethyl acetate (5 ml) was added slowly followed by water (10 ml) and diluted aqueous hydrochloric acid (2 M, 4 ml) to bring pH to 4. The phases were separated and the aqueous phase was extracted with diethyl ether (50 ml). The combined organic phases washed with water (50 ml), dried ($Na_2SO_4$), and the solvent was evaporated to give 18.4 g (99%) of the product as a colorless oil.

$^1$H NMR ($CDCl_3$): 6.52 (d, 2H), J=2 Hz), 6.41 (t, 1H, J=2 Hz), 5.96–6.11 (m. 2H), 5.43 (d, 1H, J=2 Hz), 5.37 (d, 1H, J=2 Hz), 5.29 (d, 1H, J=2 Hz), 5.26 (d, 1H, J=2 Hz), 4.60 (s, 2H), 4.49, 4.51 (dd, 4H, $J_1$=$J_2$=5 Hz), 2.40 (s, 1H).

c. 3,5-Bis-(2-propenyloxy)-benzyl acetate 3,5-Bis-(2-propenyloxy)-benzyl alcohol was acetylated according to the general procedure given in Example 24h. The crude product was isolated in 95% yield and used without further purification.

$^1$H NMR ($CDCl_3$): 6.51 (d, 2H, J=2 Hz), 6.45 (t, 1H, J=2 Hz), 5.96–6.11 (m, 2H), 5.44 (d, 1H, J=2 Hz), 5.37 (d, 1H, J=2 Hz), 5.30 (d, 1H, J=2 Hz), 5.26 (d, 1H, J=2 Hz), 5.02 (s, 2H), 4.51 (d, 4H, J=5 Hz), 2.10 (s, 3H).

d. 3,5-Bis-(23-dihydroxypropyloxy)-benzyl acetate 3,5-Bis-(2-propenyloxy)-benzyl acetate (20.8 g, 79.4 mmol) was dissolved in acetone (400 ml) and water (40 ml) and the solution was cooled in an ice-bath. Osmium tetroxide (80 mg, 0.31 mmol) and an excess of t-butylhydroperoxide was added. 4-Methylmorpholine N-oxide (37.2 g, 0.318 mol) was added portionwise, and the mixture was stirred at room temperature for 20 h. The reaction was quenched by addition of a solution of sodium hydrogen sulphite (10%, 20 ml), and the solution was concentrated in vacuo to a small volume. Water (50 ml) and methanol (75 ml) were added and the solution was treated with an acidic ion exchange resin (Amberlyst 15) to bring pH to 4. The ion exchange resin was filtered off and the solution was evaporated to an oil. Yield: 24 g (92%).

$^1$H NMR ($CD_3COCD_3$): 6.55 (d, 2H, J=2 Hz), 6.50 (t, 1H, J=2 Hz), 5.02 (s, 2H), 4.00–4.17 (m, 3H), 3.90, 3.93, 3.97 (3s, 4H), 3.52–3.70 (m, 8H), 2.03 (s, 3H).

e. 3,5-Bis-(2,3-dihydroxypropyloxy)-benzyl alcohol 3,5-Bis-(2,3-dihydroxypropyloxy)-benzyl acetate was hydrolyzed according to the general procedure given in Example 24j. The product was isolated as a semisolid in 96% yield.

$^1$H NMR (DMSO-$d_6$): 6.44 (d, 2H, J=2 Hz), 6.31 (t, 1H, J=2 Hz), 4.39 (s, 2H), 3.88–4.30 (m, 7H), 3.69–3.83 (m, 2H), 3.41 (d, 2H, J=5 Hz).

f. 3,5-Bis-(2,3-dihydroxypropyloxy)-2,4-diiodobenzyl alcohol 3,5-Bis-(2,3-dihydroxypropyloxy)-benzyl alcohol (8.50 g, 29.8 mmol) was dissolved in water (40 ml) and conc. hydrochloric acid (12 M, 2 ml) was added to bring the solution to pH to 1–2. A 70% (w/w) solution of potassium iododichloride (33.5 g, 98.9 mmol) was added dropwise with efficient stirring at room temperature. The mixture was stirred at 70° C. for 16 h, and after cooling to room temperature, the mixture was filtered. The filtrate was evaporated to a semisolid residue, water (50 ml) was added and the filtrate was evaporated again to a semisolid residue. This procedure was repeated twice, before water (70 ml) and diluted aqueous sodium hydrogen sulphite solution (10%, 7 ml) were added. The solution was treated with a strongly basic ion exchange resin (Amberlite IRA 400) to adjust pH of the solution to 11–12. The resin was filtered off and the solution was treated with a strongly acid ion exchange resin (Amberlyst 15) to adjust pH of the solution to 2. This resin was also filtered off and the solution was again treated with the strongly basic ion exchange resin (Amberlite IRA 400) to bring pH to 6–7. The resin was filtered off and the solution was evaporated to a white powder, which was purified by HPLC to give 12.4 g (77%) of the product.

$^1$H NMR (DMSO-$d_6$): 6.62 (s, 1H), 4.89 (s, 2H), 4.85 (br s, 5H), 3.90–4.05 (m, 4H), 3.73–3.84 (m, 2H), 3.43–3.59 (m, 4H).

EXAMPLE 79

N,N'-Bis-(2,3,4-trihydroxybutanoyl)-3,5-diamino-2,4,6-triiodobenzyl alcohol a. 2,3,4-Triacetoxybutanoyl bromide 2,3,4-Triacetoxybutanoyl chloride (39.9 g, 0.142 mol), prepared according to the liteature procedure Glattfeld, J. and Kribben, B., J.Am. Chem. Soc. 61 (1939) 1720) was mixed with lithium bromide (30.9 g, 0.356 mol) in methylene chloride (400 ml) and stirred at ambient temperature for 24 h. The mixture was filtered, the solid was washed with additional methylene chloride (50 ml) and the filtrate was evaporated at ambient temperature to give 45 g (97%) of the crude product as an oil.

$^1$H NMR ($CDCl_3$): 5.58–5.80 (m, 1H), 5.35–5.45 (m, 1H), 4.15–4.55 (m, 2H), 2.06, 2.08, 2.11, 2.23 (4s, 9H).

b. N,N'-Bis-(2,3,4-triacetoxybutanoyl)-3,5-diamino-2,4,6-triiodobenzyl acetate 3,5-Diamino-2,4,6-triiodobenzyl acetate (10.0 g, 17.9 mmol) was dissolved in dry N,N-dimethylacetamide (60 ml), and added dropwise with efficient stirring to 2,3,4-triacetoxybutanoyl bromide (34.7 g, 0.107 mol) cooled to 0° C. After complete addition, the mixture was stirred at ambient temperature for 2.5 h. The mixture was slowly poured into an aqueous solution of $NaHCO_3$ (5%, 700 ml). A semicrystalline precipitate was formed, filtered off and dissolved in ethyl acetate (300 ml). This solution was washed with a diluted solution of $NaHCO_3$ (5%, 70 ml), three times with aqueous HCl (0.5 M, 70 ml) and at last twice with a solution of NaCl (5%, 70 ml). The organic phase was dried ($NaSO_4$) and the solvent was evaporated to a semicrystalline residue, which was purified on a column of silica with methylene chloride/ethyl acetate (1:1) as the eluent. After evaporation of the solvent the residue was further purified by preparative HPLC to give 9.4 g (50%) of the product.

MS (ESP, m/e): 1046 ([M]$^+$, 100%).

¹H NMR (CDCl₃): 8.06 (s, 2H), 5.71–5.78 (m, 2H), 5.62–5.70 (m, 2H), 5.58 (s,2H), 4.34–4.47 (m, 2H), 4.11–4.25 (m, 2H), 2.06, 2.11 (2s, 21H).

c. N,N'-Bis-(2,3,4-trihydroxybutanoyl)-3,5-diamino-2,4,6-triiodobenzyl alcohol.

N,N'-Bis-(2,3,4-triacetoxybutanoyl)-3,5-diamino-2,4,6-triiodobenzyl acetate (8.7 g, 8.35 mmol) was dissolved in methanol (40 ml) and sodium hydroxide (2.8 g, 70 mmol) dissolved in water (10 ml) was added dropwise, with efficient stirring at ambient temperature. After 5 min additional water (30 ml) was added and after 30 min the mixture was treated with a strongly acidic ion exchange resin (Amberlyst 15) to bring pH of the solution to 2–3. The resin was filtered off and the filtrate was treated with a weakly basic ion exchange resin (Amberlyst A-21) to bring pH to 6. The resin was filtered off and the filtrate evaporated to a oil, which was purified by preparative HPLC to give 3.5 g (56%) of the product.

MS (ESP, m/e): 748 ([M]⁺, 100%), 766 ([M+H₂O]⁺, 20%).

EXAMPLE 80

5-[N'-(2,3,4-Trihydroxybutanoyl)amino]-3-hydroxymethyl-N-(2,3-dihydroxypropyl)-2,4,6-triiodobenzamide a. 5-[N'-(2,3,4-Triacetoxybutanoyl)amino]-3-acetoxymethyl-N-(2,3-diacetoxypropyl)-2,4,6-triiodobenzamide 5-Amino-3-acetoxymethyl-N-(2,3-diacetoxypropyl)-2,4,6-triiodobenzamide (30.0 g, 40.3 mmol) was dissolved in dry N,N-dimethylacetamide (50 ml) and added dropwise to 2,3,4-triacetoxybutanoyl bromide (26.0 g, 0.93 mol) at 0° C. The mixture was stirred at ambient temperature for 5 h, and then added slowly to an aqueous solution of NaHCO₃ (5%, 500 ml). A semi-crystalline precipitate was formed, filtered off and dissolved in ethyl acetate (200 ml). The organic phase was washed three times with diluted HCl (5%, 80 ml) and then twice with water (80 ml). After drying (Na₂SO₄) the solvent was evaporated to a semisolid residue. The residue was purified on a column of silica using methylene chloride/acetonitrile (4:1–3:2) as the eluent. The solvent was evaporated and the residue was further purified by preparative HPLC to give 13.8 g (35%) of the product.

MS (ESP, m/e): 988 ([M]⁺, 100%).

b. 5-[N'-(2,3,4-Trihydroxybutanoyl)amino]-3-hydroxymethyl-N-(2,3-dihydroxypropyl)-2,4,6,-triiodobenzamide 5-[N'-(2,3,4-Triacetoxybutanoyl)amino]-3-acetoxymethyl-N-(2,3-diacetoxypropyl)-2,4,6-triiodobenzamide (13.8 g, 14.0 mmol) was hydrolysed using sodium hydroxide (4.0 g, 0.10 mol) according to the procedure given in Example 79c. The product was isolated in 68% yield after purification.

MS (ESP, m/e): 736 ([M]⁺, 100%).

EXAMPLE 81

5-[N'-(2,3,4-Trihydroxybutanoyl)-amino]-3-hydroxymethyl-N-(1,3,4-trihydroxybut-2-yl)-2,4,6-triiodobenzamide a. 5-[N'-(2,3,4-Triacetoxybutanoyl)-amino]-3-acetoxymethyl-N-(1,3,4-triacetoxybut-2-yl)-2,4,6-triiodobenzamide 5-Amino-3-acetoxymethyl-N-(1,3,4-triacetoxybut-2-yl)-2,4,6-triiodobenzamide (20 g, 24.5 mmol) was acylated with 2,3,4-triacetoxybutanoyl bromide (15.9 g, 49.0 mmol) according to the procedure given in example 80a. The yield was 45%.

MS (ESP, m/e): 1060 ([M]⁺, 100%).

¹H NMR (CDCl₃): 8.14 (s, 1H), 6.28 (d, 1H, J=6 Hz), 5.77 (d, 1H, J=5 Hz), 5.66–5.74 (m, 1H), 5.57 (s, 2H), 5.45–5.55 (m, 1H), 4.65–4.77 (m, 1H), 4.12–4.48 (m, 6H), 2.27, 2.32 (2s, 3H), 2.07, 2.11, 2.13 (3s, 18H).

b. 5-[N'-(2,3,4-Trihydroxybutanoyl)amino]-3-hydroxymethyl-N-(1,3,4-trihydroxybut-2-yl)-2,4,6-triiodobenzamide 5-[N'-(2,3,4-Triacetoxymethyl)-amino]-3-acetoxymethyl-N-(1,3,4-triacetoxybut-2-yl)-2,4,6-triiodobenzamide (9.11 g, 8.6 mmol) was hydrolysed using sodium hydroxide (2.89, 72.2 mmol) according to the procedure given in example 79c. The yield was 59%.

MS (ESP, m/e): 766 ([M]⁺, 100%).

EXAMPLE 82

Viscosity

The viscosities in aqueous solution at 20° C. for various of the compounds described above were determined as given in Table 1 below.

TABLE 1

| Example | Iodine Concentration mgI/mL | Viscosity mPas |
|---|---|---|
| 5 | 435 | 13 |
| 7 | 361 | 8.0 |
| 8 | 370 | 8.3 |
| 9 | 384 | 18 |
| 10 | 381 | 11 |
| 11 | 407 | 16 |
| 13 | 398 | 12 |
| 14 | 373 | 12 |
| 15 | 348 | 7.8 |
| 15 | 394 | 14 |
| 15 | 446 | 22 |
| 15 | 537 | 75 |
| 24 | 430 | 15 |
| 26 | 385 | 13 |
| 27 | 412 | 14 |
| 28 | 404 | 15 |
| 30 | 391 | 21 |
| 32 | 403 | 18 |
| 33 | 370 | 16 |
| 35 | 394 | 15 |
| 36 | 382 | 15 |
| 37 | 458 | 30 |
| 39 | 372 | 15 |

The viscosities in aqueous solution at 20° C. for some further compounds described above were determined and are listed in Table 2. Table 2 also gives calculated values for viscosity in mPas for concentration of 400 mg I/ml and 300 mg I/ml (at 20° C.).

TABLE 2

| Example | Concentration mgI/ml | Viscosity 20° C. | Viscosity at 400 mgI/ml (CALCULATED) | Viscosity 350 mgI/ml (CALCULATED) |
|---|---|---|---|---|
| 7 | 361 | 8 | 11.5 | |
| 8 | 370 | 8.3 | 11.0 | |
| 14 | 373 | 12.0 | 15.8 | |
| 10 | 381 | 11 | 13.3 | |
| 13 | 398 | 12 | 12.2 | |
| 15 | 384 | 15 | 17.8 | |
| 11 | 409 | 17 | 15 | |
| 9 | 407 | 16 | 14.8 | |
| 15 | 394 | 14 | 14.9 | |
| 15 | 291 | 5.4 | | |
| 37 | 458 | 30 | | 15.6 |

TABLE 2-continued

| Example | Concentration mgI/ml | Viscosity 20° C. | Viscosity at 400 mgI/ml (CALCULATED) | Viscosity 350 mgI/ml (CALCULATED) |
|---|---|---|---|---|
| 37 | 398 | 16 | | |
| 5 | 435 | 13 | 10.0 | 6.9 |
| 5 | 512 | 29 | | |
| 25 | 419 | 15 | 12.6 | |
| 25 | 500 | 37 | | |
| 39 | 372 | 15 | 20.4 | 12.0 |
| 41 | 508 | 40 | 12.0 | |
| 42 | 488 | 34 | 12.8 | |
| 43 | 488 | 42 | 14.2 | |
| 44 | 481 | 24 | 10.8 | |
| 45 | 483 | 32 | 13.9 | |
| 46 | 474 | 41 | 16.4 | |
| 47 | 447 | 28 | 16.4 | |
| 49 | 380 | 11 | 13.2 | |
| 52 | 514 | 29 | 9.8 | |
| 55 | 429 | 28 | 19.4 | |
| 64 | 419 | 16 | 13.0 | 8.3 |
| 32 | 403 | 18 | 17.4 | |
| 24 | 430 | 15 | 11.3 | |
| 26 | 385 | 13 | 15.1 | 9.4 |
| 27 | 412 | 14 | 12.5 | |
| 28 | 404 | 15 | 14.6 | 9.2 |
| 30 | 391 | 21 | 23.3 | 13.4 |
| 33 | 370 | 16 | 22.9 | |
| 35 | 394 | 15 | 15.5 | 9.6 |
| 36 | 382 | 15 | 17.7 | 10.6 |
| 62 | 353 | 9 | 14.3 | |
| 67 | 407 | 18 | 16.2 | |
| 69 | 417 | 21 | 17.0 | |
| 70 | 361 | 16 | 27.8 | |
| 71 | 455 | 14 | 8.8 | 6.0 |
| 68 | 450 | 31 | 19.1 | |
| 72 | 432 | 15 | 11.0 | 7.2 |
| 73 | 396 | 10 | 10.4 | 6.7 |
| 75 | 359 | 16 | 28.4 | 14.6 |
| 74 | 399 | 16 | 15.8 | 9.3 |
| 65 | 413 | 21 | 17.8 | 10.4 |
| 66 | 401 | 15 | 15.2 | 9.3 |
| 78 | low solubility | | | |
| 79 | 379 | 14.4 | 17.2 | 10.4 |
| 80 | 444 | 23 | 14.8 | 9.4 |
| 81 | 376 | 16.2 | 21.5 | 12.2 |

Viscosity data has also been measured and calculated at 37° C. for some for these Examples and these are listed in Table 3.

TABLE 3

| Example | Concentration mgI/ml | Viscosity 37° C. | Viscosity at 350 mgI/ml (CALCULATED) |
|---|---|---|---|
| 79 | 379 | 6.9 | 5.9 |
| 80 | 444 | 11 | 5.2 |
| 81 | 376 | 8.9 | 6.1 |

EXAMPLE 83
(3,5-Dinitrobenzaldehyde)

To a solution of oxalylchloride (26 ml, 0.30 mol) in $CH_2Cl_2$ (600 ml) DMSO (43 ml, 0.60 mol) was added, maintaining the temperature between −50° C. and −65° C. To the reaction solution was then added 3,5-dinitrobenzyl alcohol (50g), in THF (100 ml), maintaining the temperature between −50° C. and −65° C. The reaction mixture was stirred at −65° C. for 30 minutes and then triethylamine (170 ml) was added at −50° C. and −65° C. The reaction temperature was then adjusted to room temperature and $H_2O$ (800 ml) was added. The organic phase was washed with sat. $NaHCO_3$ (500 ml), 5 times with diluted HCl (300 ml) and finally brine. The organic phase was then dried over $MgSO_4$ and the volatile solvents were removed at reduced pressure. The crude product was then triturated with heptane, which gave 45.8 g (89%) of 3,5-dinitrobenzaldehyde.

$^1$H NMR ($CDCl_3$, 300 MHz) δ ppm: 10.22 (s, 1H), 9.30 (d, 1H), 9.05 (t, 2H).

EXAMPLE 84
(3,5-Dinitro-O-trimethylsilylmandelonitrile)

To a mixture of 3,5-dinitrobenzaldehyde (16.0 g, 81.6 mmol) and $CH_2Cl_2$ (16 ml) $Zn(CN)_2$ (30 mg, 0.26 mmol) and then trimethylsilylcyanide (12 ml, 90.0 mmol) were added at 0° C. under an argon atmosphere. The mixture was stirred over night at room temperature. The solvent and the remaining trimethylsilylcyanide were removed at reduced pressure, which gave 23.4g (97%) of 3,5-dinitro-O-trimethylsilylmandelonitrile.

$^1$H-NMR ($CDCl_3$, 300 MHz) δ ppm: 9.09 (t, 1H), 8.68 (d, 2H), 5.70 (s, 1H), 0.35 (s, 9H).

EXAMPLE 85
(3,5-Dinitromandeloamide)

3,5-dinitro-O-trimethylsilylmandelonitrile (5.0 g, 16.9 mmol) and $BF_3$-acetic acid complex (30 ml) were dissolved in $H_2O$ (5 ml) at room temperature. The reaction temperature was raised to 115° C. immediately and stirred for 10 minutes. The reaction solution was then cooled to 0° C. $H_2O$ (100 ml) and EtOAc (200 ml) were added. The organic phase was washed with sat $NaHCO_3$ (100 ml) and brine (100 ml). Drying over $MgSO_4$ was followed by removal of solvents at reduced pressure. The residue was crystallized from isopropylacetate. The crystalline residue was left for preparative HPLC, which gave 2.2 g (54%) of 3,5-dinitromandeloamide.

$^1$H-NMR (DMSO-$d_6$, 300 MHz) δ ppm: 8.74 (d, 1H), 8.68 (t, 2H), 7.69 (s, 1H), 7.43 (s, 1H), 6.76 (d, 1H), 5.23 (d, 1H).

EXAMPLE 86
(2,4,6-Triiodo-3,5-dinitromandeloamide)

3,5-Dinitromandeloamide (5.0 g, 20.8 mmol), $PtO_2$ (50 mg, 0.22 mmol) and concentrated HCl (5 ml) were added to MeOH (100 ml) and $H_2O$ (10 ml). After hydrogenation for 1.5 hours, the catalyst was filtered off and the remaining solution was added to $LiICl_2$ (70% in $H_2O$, 24.3 g, 83.2 mmol) in $H_2O$ (50 ml). The reaction mixture was stirred for 15 minutes at room temperature. A brown precipitate was formed. The reaction was terminated with sat. $NaHSO_3$ (20 ml) and the precipitate was filtered off and washed several times with $H_2O$ and finally ether, yielding 9.2 g (79%) of 2,4,6-triiodo-3,5-diaminomandeloamide. $^1$H-NMR (DMSO-$d_6$, 300 MHz) δ ppm: 7.37 (s, 1H), 7.15 (s, 1H), 5.65 (s, 1H).

EXAMPLE 87
(O-Acetyl-2,4,6-triiodo-3,5-diaminomandeloamide)

To 2,4,6-Triiodo-3,5-diaminomandeloamide (1.21 g, 2.165 mmol) and dimethylaminopyridine (14 mg) in 40 ml pyridine was added acetic anhydride (1.33 ml). The solution was stirred for 2 hours and 20 minutes and then the volatile substances were removed at reduced pressure $H_2O$ (40 ml) was added and the solid was filtered off and washed with water. The crude material was sonicated for 10 minutes in 2:3 $CH_3CN/H_2O$ (25 ml). The solid was filtered off and washed twice with 2:3 $CH_3CN/H_2O$ (2 ml), yielding 0.86 g (64%) of O-acetyl-2,4,6-triiodo-3,5-diaminomandeloamide.

$^1$H-NMR (DMSO-$d_6$, 300 MHz) δ ppm: 7.49 (s, 1H), 7.40 (s, 1H), 6.74 (s, 1H), 5.25 (s, 4H), 2.06 (s, 3H).

EXAMPLE 88
(O-Acetyl-N,N'-bis(acetoxyacetyl)-3,5-diamino-2,4,6-triiodomandeloamide and O-Acetyl-N-(2,3-diacetoxypropionyl)-N'-acetoxyacetyl-3,5-diamino-2,4,6-triiodomandeloamide)

To O-acetyl-2,4,6-triiodo-3,5-diaminomandeloamide (530 mg, 0.88 mmol) in N,N'-dimethylacetamide (DMAC) (5 ml) was added acetoxyacetylbromide (204 mg, 1.13 mmol) at 0° C. under argon atmosphere. After 8 minutes 2,3-diacetoxypropionylbromide (478 mg, 1.89 mmol) was added and the reaction solution stirred for a total time of 1 hour and then poured into an equivalent amount of NaHCO$_3$ in H$_2$O. The solution was saturated with NaCl and extracted three times with EtOAc (50 ml). The combined EtOAc phases were dried over Na$_2$SO$_4$ and the solvent was removed at reduced pressure. The residue was left for preparative HPLC, which gave 375 mg (49%) of O-Acetyl-N-(2,3-diacetoxypropionyl)-N'-acetoxyacetyl-3,5-diamino-2,4,6-triiodomandeloamide (A) and 140 mg (20%) of O-Acetyl-N,N'-bis(acetoxyacetyl)-3,5-diamino-2,4,6-triiodomandeloamide (B). MS (ESP+, m/e): (A), 873 (M), 890 (M+H$_2$O), 895 (M+Na). (B), 801 (M), 818 (M+H$_2$O), 823 (M+Na).

$^1$H-NMR (CD$_3$CN, 300 MHz) δ ppm: (B) 8.70 (s, 2H), 6.89 (m, 2H), 6.32 (m, 2H), 4.72 (s, 4H), 2.17 (m, 9H).

EXAMPLE 89
(O-Acetyl-N,N'-bis(acetoxyacetyl)-3,5-diamino-2,4,6-triiodomandeloamide and O-Acetyl-N-(2R,3S,4-triacetoxybutyryl)-N'-acetoxyacetyl-3,5-diamino-2,4,6-triiodomandeloamide)

To O-acetyl-2,4,6-triiodo-3,5-diaminomandeloamide (660 mg, 1.10 mmol) in DMAC (6 ml) was added acetoxyacetylbromide (253 mg, 1.42 mmol) at 0° C. under argon atmosphere. After 7 minutes.2R,3S,4-triacetoxybutyrylbromide (765 mg, 2.35 mmol) was added and the reaction solution stirred for 30 minutes at 0° C. and 55 minutes at room temperature. The reaction solution was poured into sat. NaHCO$_3$ and then extracted three times with EtOAc (50 ml). The combined EtOAc phases were dried over Na$_2$SO$_4$ and the solvent was removed at reduced pressure. The residue was left for preparative HPLC, which gave 360 mg (35%) of O-Acetyl-N-(2R,3S,4-triacetoxybutyryl)-N'-acetoxyacetyl-3,5-diamino-2,4,6-triiodomandeloamide(A) and 200 mg (23%) of O-Acetyl-N,N'-bis(acetoxyacetyl)-3,5-diamino-2,4,6-triiodomandeloamide(B). MS (ESP+, m/e): (A), 945 (M), 962 (M+H$_2$O), 967 (M+Na). (B), see example 88.

EXAMPLE 90
(O-Acetyl-N-(2,2-bis(acetoxymethyl)-acetyl)-N'-acetoxyacetyl-3,5-diamino-2,4,6-triiodomandeloamide)

To O-acetyl-2,4,6-triiodo-3,5-diaminomandeloamide (100 mg, 0.16 mmol) in DMAC (1 ml) was added acetoxyacetylbromide (28 µl, 0.24 mol) at 0° C. under argon atmosphere. After 1 hour 2,2-bis(acetoxymethyl)-acetylbromide (160 µl) was added and the reaction solution stirred for 40 minutes at 0° C. The reaction solution was poured into sat NaHCO$_3$ and then extracted three times with EtOAc (50 ml). The combined EtOAc phases were dried over Na$_2$SO$_4$ and the solvent was removed at reduced pressure. The residue was left for preparative HPLC, which gave 30 ng (21%) of O-Acetyl-N-(2,2-bis(acetoxymethyl)-acetyl)-N'-acetoxyacetyl-3,5-diamino-2,4,6-triiodomandeloamide. MS (ESP+, m/e): 887 (M), 904 (M+H$_2$O), 909 (M+Na).

EXAMPLE 91
(O,N,N'-Triscrotonyl-3,5-diamino-2,4,6-triiodomandeloamide

To crotonylbromide (2.41 g, 16.2 mmol) was added 2,4,6-Triiodo-3,5-diaminomandeloamide (1.5 g, 2.69 mmol) in DMAC (15 ml) at 0° C. under argon atmosphere. The reaction solution was stirred for 2.5 hours and the volatile material was removed at reduced pressure. Diluted NaHCO$_3$ (40 ml) and CH$_2$Cl$_2$ (70 ml) were added to the residue and the aqueous phase was extracted with further CH$_2$Cl$_2$ (30 ml). The combined organic phases were washed with diluted HCl (50 ml) and twice with H$_2$O (50 ml). After drying over Na$_2$SO$_4$ and removal of the solvent at reduced pressure, the formed crude product was left for preparative HPLC, which gave 1.15 g (58%) of O,N,N'-triscrotonyl-3,5-diamino-2,4,6-triiodomandeloamide. MS (ESP+, m/e): 763 (M), 780 (M+H$_2$O), 785 (M+Na).

EXAMPLE 92
(O,N,N'-Tris(2,3-dihydroxybutyryl)-3,5-diamino-2,4,6-triiodomandeloamide)

To O,N,N'-triscrotonyl-3,5-diamino-2,4,6-triiodomandeloamide (0.42 g, 0.55 mmol) in acetone/H$_2$O (8 ml) was added N-methylmorpholine N-oxide (0.39 g, 3.31 mmol) and OsO$_4$ (0.02 g, 0.079 mmol) added at room temperature. After 2 hours H$_2$O (4 ml) was added and the mixture was stirred overnight. To the reaction mixture was added sat. NaHSO$_3$ (0.2 ml) and the volatile material was removed at reduced pressure. The residue was taken up in MeOH/H$_2$O (1:3, 15 ml) and Amberlyst 15 was added until the pH reached 2–3. The resin was filtered off and Amberlyst A 26 was added until the pH reached 6–7. The resin was filtered off and the solvent removed at reduced pressure. The residue was left for preparative HPLC, which gave 0.33 g (69%) of O,N,N'-tris(2,3-dihydroxybutyryl)-3,5-diamino-2,4,6-triiodomandeloamide.

MS (ESP+, m/e): 865 (M).

EXAMPLE 93
(O,N,N'-tris(2,3-Diacetoxypropionyl)-3,5-diamino-2,4,6-triiodomandeloamide)

To 2,3-Diacetoxypropionylbromide (26.5 g, 98.4 mmol) was added 2,4,6-Triiodo-3,5-diaminomandeloamide (9.2 g, 16.4 mmol) in DMAC (100 ml) at 0° C. under argon atmosphere. The reaction solution was stirred for 1 hour at room temperature and then added to diluted NaHCO$_3$ (300 ml) and EtOAc (300 ml). The aqueous phase was extracted twice with EtOAc (250 ml) and the combined organic phases were washed with brine (200 ml). After drying over MgSO$_4$ and removal of the solvent at reduced pressure, the residue was dissolved in isopropylacetate (20 ml) and added to ice cooled isopropylether (200 ml). The formed precipitate was filterd off and left for preparative HPLC, which gave 14.0 g (79%) of O,N,N'-tris(2,3-Diacetoxypropionyl)-3,5-diamino-2,4,6-triiodomandeloamide. MS (ESP+, m/e): 1075 (M), 1093 (M+H$_2$O), 1097 (M+Na), 1162 (M+DMAC).

EXAMPLE 94
(O,N,N'-Tris(2R,3S,4-triacetoxybutyryl)-3,5-diamino-2,4,6-triiodomandeloamide)

To 2R,3S,4-triacetoxybutyrylbromide (3.15 g, 9.7 mmol) was added 2,4,6-Triiodo-3,5-diaminomandeloamide (0.676 g, 1.2 mmol) in DMAC (10 ml) at 0° C. under argon atmosphere. The reaction solution was stirred for 2 hours at room temperature and then added to diluted NaHCO$_3$ (100 ml) and EtOAc (100 ml). The aqueous phase was extracted twice with EtOAc (50 ml) and the combined organic phases were washed with brine (50 ml). After drying over MgSO$_4$ and removal of the solvent at reduced pressure, the residue was left for preparative HPLC, which gave 250 mg (16%) of O,N,N'-tris(2R,3S,4-triacetoxybutyryl)-3,5-diamino-2,4,6-triiodomandeloamide. MS (ESP+, m/e): 1165 (M-I), 1307 (M+H$_2$O).

EXAMPLE 95

(O,N,N'-Tris(2,4-diacetoxybutyryl)-3,5-diamino-2,4,6-triiodomandeloamide

To 2,4-diacetoxybutyrylbromide (4.37 g, 16.4 mmol) was added 2,4,6-Triiodo-3,5-diaminomandeloamide (1.0 g, 1.79 mmol) in DMAC (6 ml) at 0° C. under argon atmosphere. The reaction solution was stirred for 2.5 hour at room temperature and then added to sat. NaHCO$_3$ (60 ml) and EtOAc (100 ml) The aqueous phase was extracted twice with EtOAc (50 ml) and the combined organic phases were washed 3 times with brine (50 ml). After drying over MgSO$_4$ and removal of the solvent at reduced pressure, the residue was left for preparative HPLC, which gave 670 mg (33%) of O,N,N'-tris(2,4-diacetoxybutyryl)-3,5-diamino-2,4,6-triiodomandeloamide.

EXAMPLE 96

(O,N,N'-Tris(2,2-bis(acetoxymethyl)-acetyl)-3,5-diamino-2,4,6-triiodomandeloamide To 2,2-bis(acetoxymethyl)-acetylbromide (4.30 g, 16.1 mmol) was added 2,4,6-Triiodo-3,5-diaminomandeloamide (0.9 g, 1.61 mmol) in DMAC (5 ml) at 0° C. under argon atmosphere. The reaction solution was stirred for 2 hours at room temperature and then added to sat. NaHCO$_3$ (60 ml) and EtOAc (100 ml). The aqueous phase was extracted twice with EtOAc (50 ml) and the combined organic phases were washed 3 times with brine (50 ml). After drying over MgSO$_4$ and removal of the solvent at is reduced pressure, the residue was left for preparative HPLC, which gave 620 mg (34%) of O,N,N'-tris(2,2-bis(acetoxymethyl)-acetyl)-3,5-diamino-2,4,6-triiodomandeloamide. MS (ESP+, m/e): 1117 (M), 1135 (M+H$_2$O).

General Procedure for Hydrolysis of Polyacylated Compounds

The polyacylated compound was dissolved in a mixture of methanol and water containing NaOH (1 M, 1.2 mol-equivalents/acylated hydroxy group). After 1 hour Amberlyst 15 was added until the pH reached 2–3. The resin was filtered off Amberlyst A 21 was added until the pH reached 6–7. The resin was filtered off and the solvents removed at reduced pressure. The residue was left for preparative HPLC.

EXAMPLE 97

(N,N'-Bis(hydroxyacetyl)-3,5-diamino-2,4,6-triiodomandeloamide)

O-Acetyl-N,N'-bis (acetoxyacetyl)-3,5-diamino-2,4,6-triiodomandeloamide (290 mg, 0.36 mmol) gave 210 mg (86%) of N,N'-bis(hydroxyacetyl)-3,5-diamino-2,4,6-triiodomandeloamide.

$^1$H-NMR (DMSO-d$_6$, 300 MHz) δ ppm: 9.76 (m, 2H)r 7.42 (s, 1H), 7.26 (m, 1H), 6.64 (m, 1H), 5.83 (d, 1H), 5.57 (m, 2H), 3.99 (s, 4H). MS(ESP+, m/e): 675 (M), 692 (M+H$_2$O), 697 (M+Na).

EXAMPLE 98

(N-(2,3-Dihydroxypropionyl)-N'-hydroxyacetyl-3,5-diamino-2,4,6-triiodomandeloamide)

O-Acetyl-N-(2,3-diacetoxypropionyl)-N'-acetoxyacetyl-3,5-diamino-2,4,6-triiodomandeloamide (375 mg, 0.43 mmol) gave 250 mg (82%) of N-(2,3-Dihydroxypropionyl)-N'-hydroxyacetyl-3,5-diamino-2,4,6-triiodomandeloamide.

$^1$H-NM (DMSO-d$_6$, 300 MHz) δ ppm: 9.75 (m, 2H), 7.41 (s, 1H), 7.24 (m, 1H), 6.64 (m, 1H), 5.83 (d, 1H), 5.72 (m, 1H), 5.57 (m, 1H), 4.78 (m, 1H), 4.05 (m, 1H), 3.99 (s, 2H), 3.81 (m, 1H), 3.58 (m, 1H). MS (ESP+, m/e): 705 (M), 723 (M+H$_2$O), 727 (M+Na).

EXAMPLE 99

(N,N'-Bis(2,3-Dihydroxypropionyl)-3,5-diamino-2,4,6-triiodomandeloamide)

O,N,N'-Tris(2,3-Diacetoxypropionyl)-3,5-diamino-2,4,6-triiodomandeloamide (43.5 g, 40.4 mmol) gave 18.4 g (62%) of N,N'-Bis(2,3-Dihydroxypropionyl)-3,5-diamino-2,4,6-triiodomandeloamide.

$^1$H-NM (DMSO-d$_6$, 300 Hz) δ ppm: 9.70 (m, 2H), 7.39 (s, 1H), 7.23 (m, 1H), 6.62 (m, 1H), 5.82 (d, 1H), 5.70 (m, 2H), 4.77 (m, 2H), 4.05 (m, 2H), 3.77 (m, 2H), 3.57 (m, 2H). MS (ESP+, m/e): 735 (M) 752 (M+H$_2$O ), 756 (M+Na).

EXAMPLE 100

(N-(2R,3S,4-Trihydroxybutyryl)-N'-hydroxyacetyl-3,5-diamino-2,4,6-triiodomandeloamide)

O-Acetyl-N-(2R,3S,4-triacetoxybutyryl)-N'-acetoxyacetyl-3,5-diamino-2,4,6-triiodomandeloamide (360 mg, 0.38 mmol) gave 250 mg (90) of N-(2R,3S,4-Trihydroxybutyryl)-N'-hydroxyacetyl-3,5-diamino-2,4,6-triiodomandeloamide. $^1$H-NMR (DMSO-d$_6$, 300 MHz) δ ppm: 9.72 (m, 2H), 7.41 (s, 1H), 7.25 (m, 1H), 6.63 (m, 1H). 5.83 (d, 1H), 5.58 (m, 1H), 5.23 (m, 1H), 4.59 (s, 1H), 4.43 (m, 1H), 4.08 (s, 1H), 3.99 (s, 2H), 3.90 (m, 1H), 3.50 (m, 1H), 3.40 (m, 1H).

MS (ESP+, m/e): 757 (M+Na)

EXAMPLE 101

(N,N'-Bis(2,3-dihydroxybutyryl)-3,5-diamino-2,4,6-triiodomandeloamide)

O,N,N'-Tris(2,3-dihydroxybutyryl)-3,5-diamino-2,4,6-triiodomandeloamide (1.19 g, 1.38 mmol) gave 100 mg (10%) of N,N'-Bis(2,3-dihydroxybutyryl)-3,5-diamino-2,4, 6-triiodomandeloamide.

$^1$H-NMR (DMSO-d$_6$, 300 MHz) δ ppm: 9.68 (m, 2H), 7.39 (s, 1H), 7.23 (m, 1H), 6.68 (m, 1H), 5.84 (d, 1H), 5.43 (m, 2H), 4.51 (s, 2H), 3.97 (m, 2H), 3.78 (s, 2H), 1.18 (d, 6H). MS (ESP+, m/e): 753 (M), 780 (M+H$_2$O), 785 (M+Na).

EXAMPLE 102

N,N'-Bis(2,4-dihydroxybutyryl)-3,5-diamino-2,4,6-triiodomandeloamide)

O,N,N'-Tris(2,4-diacetoxybutyryl)-3,5-diamino2,4,6-triiodomandeloamide (0.67 g, 0.60 mmol) gave 430 mg (93%) of N,N'-Bis(2,4-dihydroxybutyryl)-3,5-diamino-2,4,6-triiodomandeloamide.

$^1$H-NMR (DMSO-d$_6$, 300 MHz) δ ppm: 9.65 (m, 2H), 7.39 (s, 1H), 7.23 (m, 1H), 6.63 (m, 1H), 5.83 (d, 1H), 5.57 (m, 2 H), 5.23 (m, 1H), 4.47 (m, 2H), 4.12 (m, 2H), 3.59 (m, 4H), 2.00 (m, 2H), 1.76 (m, 2H). MS (ESP+, m/e): 763 (M), 780 (M+H$_2$O), 785 (M+Na).

EXAMPLE 103

(N,N'-Bis(2,2-bis(hydroxymethyl)-acetyl)-3,5-diamino-2,4, 6-triiodomandeloamide)

O,N,N'-Bis(2,2-bis(acetoxymethyl)-acetyl)-3,5-diamino-2,4,6-triiodomandeloamide (620 mg, 0.56 mmol) gave 182 mg (43%) of N,N'-Bis(2,2-bis(hydroxymethyl)-acetyl)-3,5-diamino-2,4,6-triiodomandeloamide.

$^1$H-NMR (DMSO-d$_6$, 300 MHz) δ ppm: 9.90 (m, 2H), 7.39 (s, 1H), 7.24 (m, 1H), 6.59 (m, 1H), 5.82 (d, 1H), 4.57 (s, 4H), 3 82 (m, 4H), 3.67 (m, 4H), 2.68 (m, 2H).

EXAMPLE 104
(N,N'-Bis(2R,3S,4-trihydroxybutyryl)-3,5-diamino-2,4,6-triiodomandeloamide)

O,N,N-Tris(2R,3S,4-triacetoxybutyryl)-3,5-diamino-2,4, 6-triiodomandeloamide (250 mg, 0.20 mmol) gave 120 mg (75%) of N,N'-Bis(2R,3S,4-trihydroxybutyryl)-3,5-diamino-2,4,6-triiodomandeloamide.

$^1$H-NMR (DMSO-$d_6$, 300 MHz) δ ppm: 9.69 (m, 2H), 7.41 (s, 1H), 7.25 (m, 1H), 6.63 (m, 1H), 5.84 (d, 1H), 5.22 (m, 2H), 4.58 (m, 2H), 4.44 (m, 2H), 4.09 (m, 2H), 3.91 (m, 2H), 3.51 (m, 2H), 3.39 (m, 2H).

EXAMPLE 105
(O-Acetyl-N-(2R,3R,4-triacetoxybutyryl)-N'-acetoxyacetyl-3,5-diamino-2,4,6-triiodomandeloamide)

O-Acetyl-2,4,6-triiodo-3,5-diaminomandeloamide (31.9 g, mmol) was reacted first with acetoxyacetyl bromide (14.1 g, 79.5 mmol) and then with 2R,3R,4-triacetoxybutyryl bromide (43.1 g, 0.13 mol) according to the procedure in example 89. The amount of product isolated was 22.3 g (44%)

MS (ESP+, m/e): 945 (M), 962 (M+$H_2O$)

EXAMPLE 106
(N-(2R,3R,4-Trihydroxybutyryl)-N'-hydroxyacetyl-3,5-diamino-2,4,6-triiodomandeloamide O-Acetyl-N-(2R,3R,4-triacetoxybutyryl)-N'-acetoxyacetyl-3,5-diamino2,4,6-triiodomandeloamide (16.8 g, 17.8 mmol) was hydrolyzed, according to the general method above in Example 96 to give 12.4 g (95%) of product.

MS (ESP+, m/e): 735 (M), 743 (M+$H_2O$).

EXAMPLE 107
(5-Amino-3-acetoxymethyl-2,4,6-triiodobenzoic acid)

5-Amino-3-hydroxymethyl-2,4,6-triiodobenzoic acid (140.5 g, 0.26 mol) was dissolved in pyridine (450 ml) and dimethylaminopyridine (0.10 g) was added. To this solution, with efficient stirring and cooling in an ice-bath was added dropwise acetic anhydride (300 ml). After addition the reaction mixture was allowed to reach ambient temperature and after 4 h the mixture was evaporated to dryness. The brown residue was triturated with acetone (3×150 ml), filtered and pumped dry. Isolated 141 g (93%) of a yellow powder.

MS (ESP+, m/e); 587 (M).

$^1$H-NMR (DMSO-$d_6$, 300 MHz) δ ppm: 5.43 (br. s, 2H), 5.35 (s, 2H), 3.45 (br. s, 1H), 2.03 (s, 3H).

EXAMPLE 108
(5-[N-(2,3-Diacetoxypropionyl)amino]-3-acetoxymethyl-2, 4,6-triiodobenzoic acid)

5-Amino-3-acetoxymethyl-2,4,6-triiodobenzoic acid (141.0 g, 0.24 mol) was dissolved in N,N-dimethylacetamide (250 ml) and added slowly, with efficient stirring and cooling in an ice-bath, to 2,3-diacetoxypropionyl bromide. The temperature was then allowed to reach ambient temperature and after 5 h the reaction mixture was concentrated to ca. ⅓ of its volume in high vacuo, and below 60° C. The oily residue was slowly added to a well stirred solution of water (2.5, pH=2). The solid residue was dissolved in ethyl acetate (1.0 l) and the solution was washed with acidic water (2×1.0l, pH=2) and neutral water (1.0 l). The organic-phase was then extracted with a solution of NaHCO$_3$ (10%, ca 1,5 l) until pH of the aqueous phase reached 8. The aqueous phase was then acidified slowly with conc. hydrochloric acid (ca. 50 ml) to pH=2, and extracted with ethyl acetate (2×0.7 l). The organic phases were treated with activated charcoal (3 g), dried (MgSO$_4$) and the solvent evaporated to give a light brown foam. This foam was dissolved in acetone (70 ml), toluene (ca. 150 ml) was added until the solution became turbid, and the solution was evaporated in vacuo on a rotatory evaporator at a temperature ≦30° C. to ca. ¼ of its volume. The precipitate formed was filtered off. The filtercake was dissolved again in acetone (70 ml) and the procedure repeated once giving after drying a nearly white powder of weight 160 g (88%).

$^1$H-NMR (CDCl$_3$, 300 MHz) δ ppm: 8.05 & 8.24 (2 s, 1H), 6.50 (br s, 1H), 5.67 (m, 1H), 5.56 (s, 2H), 4.72 (m, 1H), 4.52 (m, 1H), 2.28 (s, 3H), 2.11 (s, 3H).

EXAMPLE 109
(5-[N-(2,3-Diacetoxypropionyl)amino]-3-acetoxymethyl-2, 4,6-triiodobenzoyl chloride)

5-[N-(2,3-Diacetoxypropionyl)amino]-3-acetoxymethyl-2,4,6-triiodobenzoic acid (160 g, 0.21 mol) was suspended in acetonitrile (180 ml). Thionyl chloride (61 ml, 0.84 mol) was added and one drop of N,N-dimethylformamide and the mixture was heated to 55° C. with efficient stirring. After 2.5 h the mixture was evaporated to an oil, which was dissolved in methylene chloride (1.0 l) The organic solution was washed with water (2×200 ml) and then stirred for 10 min. with a diluted solution of NaHCO$_3$ (2%, 200 ml) The phases were separated and the organic phase dried (MgSO$_4$), the solvent evaporated to give a solid residue, which was taken up in ethyl acetate (250 ml) and filtered through a pad of silica. After evaporation of solvent and drying under vacuum there was 141 g (86%) of a foam.

$^1$H-NMR (DMSO-$d_6$, 300 MHz) δ ppm: 7.99 (s, 1H), 5.68 (m, 1H), 5.57 (s, 2H), 4.72 (m, 1H), 4.51 (m, 1H), 2.27 (s, 3H), 2.12 (s, 6H).

EXAMPLE 110
5-[N-(2,3-Dihydroxypropionyl)amino]-3-hydroxymethyl-2, 4,6-triiodo-N-(2,3-dihydroxypropyl)benzamide 5-[N-(2,3-Diacetoxypropionyl)amino]-3-acetoxymethyl-2,4,6-triiodobenzoyl chloride (7.71 g, 9.9 mmol), 2,3-dihydroxypropylamine (1.48 g, 16.2 mmol), lithium bromide (90 mg, 1 mmol) and triethylamine (2.27 ml, 16.2 mmol) were mixed in tetrahydro-furan (55 ml) at ambient temperature. The temperature was increased to 65° C. and held there for 26 h with efficient stirring, and the mixture was then evaporated to dryness. The residue was dissolved in a mixture of water and methanol (6:1, 70 ml) and treated with a strongly basic anion exchange resin (Dowex 1×8) for 2.5 h. The resin was filtered off, the solution diluted with further water (50 ml) and treated with a strongly acidic cation exchange resin (Amberlyst 15) to bring the pH of the solution to 5.5–6.0. The resin was filtered off and the solution was treated with activated charcoal (0.35 g), filtered and evaporated to a light yellow to white solid residue. This was triturated with acetonitrile (20 ml) for 12 h, giving 5.8 g (70%) of a white crystalline residue.

MS (ESP+, m/e): 706 (M).

EXAMPLE 111
(5-(2,2-Dimethyl-1,3-dioxolane-4-carbamido)-3-hydroxymethyl-N-(2,2-dimethyl-1,3-dioxolane-4-methyl)-2,4,6-triiodobenzamide)

5-(2,3-Dihydroxypropionyl)amino-3-hydroxymethyl-2,4, 6-triiodo-N-(2,3-dihydroxypropyl)benzamide (26.0 g, 36.8 mmol), acetone (470 ml), 2,2-dimethoxypropane (50 ml) and a strongly acidic ion exchange resin (Amberlyst 15) were all mixed and stirred at ambient temperature until a clear solution was formed (ca. 1 h) The resin was filtered off, the filtrate was then filtered through a pad of dry NaHCO$_3$ and then evaporated to give an oil. Trituration with diisopropyl ether (80 ml) left a white precipitate which was filtered off giving 28.3 g (98%).

$^1$H-NMR (CDCl$_3$, 300 MHz) δ ppm: 8.35 (s, 1H), 6.37 (m, 1H), 5.19 (s, 2H), 4.66 (t, 1H), 4.36 (m, 2H), 4.10 (m, 1H), 3.82 (m, 2H), 3.44 (m, 2H), 1.51 (s, 3H), 1.45 (s, 3H), 1.39 (s, 3H), 1.33 (s, 3H).

EXAMPLE 112

(5-(2,2-Dimethyl-1,3-dioxolane-4-carbamido)-3-formyl-N-(2,2-dimethyl-1,3-dioxolane-4-methyl)-2,4,6-triiodobenzamide)

5-(2,2-Dimethyl-1,3-dioxolane-4-carbamido)-3-hydroxymethyl-N-(2,2-dimethyl-1,3-dioxolane-4-methyl)-2,4,6-triiodobenzamide (82.6 g, 0.11 mol), pyridinium chloro-chromate (40.1 g, 0.19 mol) and molecular sieves (4 A, powder, 80.2 g) were all mixed in methylene chloride (3.2 l) and stirred well at ambient temperature. After 2.5 h the mixture was filtered and the filtrate stirred with a solution of NaHCO$_3$ (10%, 2 l) for 1 h. The phases were separated, the aqueous phase washed with further methylene chloride (2×0.5. l). The organic phases were back extracted with water (1.0 l) and then filtered through a pad of silica. The solvent was evaporated and the residue pumped in vacuo to give 59.5 g (72%) of a slightly green powder.

$^1$H-NMR (CDCl$_3$, 300 Mz) δ ppm: 9.53 (s, 1H), 8.44 (s, 1H), 6.41 (s, 1H), 4.66 (t, 1H), 4.39 (m, 2H), 4.10 (m, 1H), 3.81 (m, 2H), 3.48 (m, 2H), 1.67 (s, 3H), 1.46 (s, 3H), 1.42 (s, 3H), 1.33 (s, 3H).

EXAMPLE 113

(5-(2,2-Dimethyl-1,3-dioxolane-4-carbamido)-3-(O-trimethylsilyl-cyanomethyl)-N-(2,2-dimethyl-1,3-dioxolane-4-methyl)-2,4,6-triiodobenzamide)

5-(2,2-Dimethyl-1,3-dioxolane-4-carbamido)-3-formyl-N-(2,2-dimethyl-1,3-dioxo-lane-4-methyl)-2,4,6-triiodobenzamide (58.4 g, 74.5 mmol), trimethylsilyl cyanide (40 ml, 0.32 mol) and a catalytic amount of zinc iodide (100 mg, 0.31 mmol) were all mixed and stirred at ambient temperature for 6 h. The mixture was then evaporated to dryness and pumped in high vacuo over night. The yield seem to be quantitative (according to NMR) and the product (60.4 g) was used directly in next step.

$^1$H-NMR (DMSO-d$_6$, 300 MHz) δ ppm; 8.31 (s, 1H), 6.41 (s, 1H), 5.91–6.20 (m, 1H), 4.68 (m, 1H), 4.38 (m, 2H), 4.12 (t, 1H), 3.83 (m, 2H), 3.47 (m, 2H), 1.66,1.69 (2s, 3H), 1.47,1.45 (2s, 6H), 1.35,1.25 (2s, 3H), 0.27 (br s, 9H).

EXAMPLE 114

(5-(2,3-Dihydroxypropionyl)amino-3-N-(2,3-dihydroxypropyl)carbamido-2,4,6-triiodomandeloamide and 5-(2,3-dihydroxypropionyl)amino-3-carbamido-2,4,6-triiodomandeloamide)

The reaction product from Example 113 (60.4 g) was treated with conc. hydrochloric acid (100 ml) for 5 h. The mixture was first evaporated to ⅓ of its volume, then diluted with water (700 ml), neutralized with a basic ion exchange resin (Amberlite A) to pH=7, evaporated to dryness and then left for preparative HPLC purification. 22.5 g (40.3% over two steps) of 5-(2,3-dihydroxypropionyl)amino-3-N-(2,3-dihydroxypropyl)carbamido-2,4,6-triiodomandeloamide was isolated.

MS (ESP+, m/e): 749 (M), 767 (M+H$_2$O).

$^1$H-NMR (DMSO-d$_6$, 300 MHz) δ ppm 9.71 (s, 1H), 8.48 (m, 1H), 7.41,7.24 (2s, 2H), 6.57 (s, 1H), 5.74 (d, 2H), 4.79 (s, 1H), 4.68 (d, 1H), 4.45 (m, 1H), 4.06 (m, 1H), 3.39–3.78 (m, 5H), 3.13–3.26 (m, 2H).

There was also isolated 1.4 g of 5-(2,3-dihydroxypropionyl)amino-3-carbamido-2,4,6-triiodomandeloamide.

MS (ESP+, m/e): 675 (M).

$^1$H-NMR (DMSO-d$_6$, 300 MHz) δ ppm: 9.68 (s, 1H), 7.93,7.83 (2s, 1H), 7.56 (s, 1H), 7.39 (s, 1H), 7.22 (s, 1H), 6.57 (m, 1H), 4.78 (s, 1H), 4.06 (m, 1H), 3.77 (m, 1H), 3.57 (m, 1H).

EXAMPLE 115

(5-(2,3-Diacetoxypropionyl)amino-2,4,6-triiodo-1,3-dibenzyl acetate)

To 2,3-diacetoxypropionylbromide (10.5 g, 41.6 mmol) in a flask was added 5-amino-2,4,6-triiodo-1,3-dibenzyl acetate (9.0 g, 14.6 mmol) dissolved in DMAC (15 ml) with cooling in an ice-bath. The temperature was allowed to reach ambient temperature with efficient stirring. After 4 h. the mixture was added slowly to a well stirred aqueous solution of NaHCO$_3$ (5%, 100 ml). A light tan colored precipitate was formed and filtered off. The filtercake was dissolved in methylene chloride (40 ml) and applied to a column of alumina. After elution and evaporation of the solvent there was 9.6 g (84%) of a white compound.

$^1$H-NMR (CDCl$_3$, 300 MHz) δ ppm. 7.96 (s, 1H), 5.68 (m, 5H), 4.73 (m, 1H), 4.52 (m, 1H), 2.27 (s, 3H), 2.12 (s, 6H), 2.10 (s, 3H).

MS (ESP+, m/e): 787 (M), 804 (M+H$_2$O)

EXAMPLE 116

(5-(2,3-Dihydroxypropionyl)amino-2,4,6-triiodo-1,3-dibenzyl alcohol)

5-(2,3-Diacetoxypropionyl)amino-2,4,6-triiodo-1,3-dibenzyl acetate (6.76 g, 8.59 mmol) was dissolved in methanol (100 ml) and sodium hydroxide (1.38 g, 34.3 mmol) dissolved in water (5 ml) was added dropwise with stirring. After 1.5 h the mixture was diluted with water (60 ml) and then treated with a strongly acidic ion exchange resin (Amberlyst 15 ca. 45 g) to bring pH to neutral. The resin was filtered off and the filtrate evaporated to dryness leaving a crystalline product of 5.58 g (quantitative yield).

MS (ESP+, m/e): 619 (M).

EXAMPLE 117

(5-(2,2-Dimethyl-1,3-dioxolane-4-carbamido)-2,4,6-triiodo-1,3-dibenzyl alcohol 5-(2,3-Dihydroxypropionyl)amino-2,4,6-triiodo-1,3-dibenzyl alcohol (10.4 g, 13.2 mmol) was suspended in acetone (270 ml) and conc. sulfuric acid (3 ml) was added. The mixture was stirred for 40 h at ambient temperature until a clear solution was formed. The mixture was concentrated to ca 70–80 ml and diluted with a solution of NaHCO$_3$ (5%, 100 ml), and the resulting solution was extracted with ethyl acetate (2×100 ml) The organic phases were dried (NaSO$_4$) and the solvent evaporated to give 7.1 g (82%) of a white crystalline product.

$^1$H-NMR, (CDCl$_3$, 300 MHz) δ ppm: 8.38 (s, 1H), 5.24 (s, 4H), 4.66 (t, 1H), 4.35 (m, 2H), 1.67 (s, 3H), 1.46 (s, 3H).

MS (ESP+, m/e): 659 (M) 676 (M+H$_2$O).

EXAMPLE 118

(5-(2,2-Dimethyl-1,3-dioxolane-4-carboxamido)-2,4,6-triiodo-1,3-dibenzaldehyde)

5-(2,2-Dimethyl-1,3-dioxolane-4-carboxamido)-2,4,6-triiodo-1,3-dibenzyl alcohol (1.40 g, 2.12 mmol), pyridinium chlorochromate (1.78 g, 8.27 mmol) and molecular sieves (4 A powder, 4.0 g) were all nixed in methylene chloride (40 ml), refluxed for 4 h and then stirred over night at 45° C. The mixture was filtered and worked up as described above in example 112. After work up there was 0.80 g (58%) of a light yellow crystalline product.

$^1$H-NMR (CDCl$_3$, 300 MHz) δ ppm. 9.61 (s, 2H), 8.32 (s, 1H), 4.71 (m, 1H), 4.40 (m, 2H), 1.69 (s, 3H), 1.47 (s, 3H).

MS (ESP+, m/e): 655 (M), 672 (M+H$_2$O).

EXAMPLE 119
(5-(2,2-Dimethyl-1,3-dioxolane-4-carboxamido)-2,4,6-triiodo-1,3-bis(O-trimethyl-silylcyanomethyl)-benzene)

5-(2,2-Dimethyl-1,3-dioxolane-4-carboxamido)-2,4,6-triiodo-1,3-dibenzaldehyde (0.12 g, 0.18 mmol), trimethyl-silyl cyanide (2.0 ml, 1.5 mmol) and a catalytic amount of zinc iodide (0.02 g, 0.06 mmol) were all mixed and stirred at ambient temperature for 24 h The mixture was then evaporated to dryness and pumped in high vacuo for 10 h. The crude product (0.16 g), was used directly in next step without purification.

$^1$H-NMR (CDCl$_3$, 300 MHz) δ ppm: 6.59 (m, 3H), 4.61 (m, 1H), 4.12 (m, 2H), 0.09 (s, 9H), 0.05 (s, 9H).

EXAMPLE 120
(5-(2,3-Dihydroxypropionyl)amino-2,4,6-triiodo-1,3-bis)hydroxy-carbamidomethyl)benzene)

5-(2,2-Dimethyl-1,3-dioxolane-4-carbamido)-2,4,6-triiodo-1,3-bis-(O-trimethylsilyl-cyanomethyl)benzene was treated and worked up according to the procedure in example 114. The product was isolated in 7% yield.

MS (ESP+, m/e): 705 (M), 723 (M+H$_2$O).

EXAMPLE 121
Determination of Viscosity

The apparatus consisted of a thermostated 10 μl graduated sample syringe connected to a conical shaped 100 μl sample vial. The syringe needle as well as a probe for temperature measurements (±0.2° C.) was inserted through an airtight septum at the top of the vial. Through the septum was also inserted a small tubing connected to an air syringe via a PTFE tubing.

To determine viscosity, 15≧75 μl of the sample liquid was placed at the bottom of the sample vial. The liquid was forced up into the sample syringe by a slight over pressure generated manually by the air syringe. When the syringe was almost filled, the over pressure was released so the liquid, forced only by gravity, could flow freely out from the syringe back into the vial. The time for the liquid surface to pass between the marks of e.g. 5 and 10 μl in the syringe was measured The viscosity is calculated as follows:

$$\eta_S = \eta_R * (d_S/d_R) * (t_S/t_R)$$

η$_S$=Viscosity of the sample

η$_R$=Viscosity of a reference sample with known viscosity and with similar composition as the sample e.g. Iohexol or Iodixanol d$_S$=Density of sample solution d$_R$=Density of reference solution t$_S$=Average time for sample surface to pass between two marks in the syringe t$_R$=Corresponding time for reference sample The results of these determinations of viscosity for various of the present Examples and two commercially available X-ray contrast media are shown in Table 1' below. In all cases, the values refer to concentrations of 350 mgI/ml at a temperature of 20° C.

TABLE 1

| Example | Viscosity (mPas) |
|---|---|
| 97 | 6.9 |
| 98 | 6.9 |
| 99 | 7.4 |
| 100 | 9.7 |
| 101 | 13.4 |
| 102 | 15.0 |
| 103 | 11.8 |
| 104 | 17.0 |
| 106 | 8.8 |
| 113 | 7.5 |
| 114 | 10.1 |
| Iohexol[1] | 20.4 |
| Iomeprol[2] | 15.4 |

[1]Data from M. J. Kern, R. A. Roth, F. V. Aguirre, G. Beauman, R. Vogel: American Heart Journal, Vol 123 (1), 160–165, 1992.
[2]Data from A. Gallotti, F. Uggeri, A. Favilla, M. Cabrini, C. de Haen: European Journal of Radiology, Vol 18 (suppl 1), S1–S12, 1994.

What is claimed is:

1. A compound of formula $C_6R_6$ wherein three non-adjacent R groups are iodine and the remaining R groups are non-ionic, hydrophilic moieties, said compound being water soluble at 20° C. to a concentration of at least 350 mgI/ml and which in aqueous solution at 20° C. at a concentration of 350 mgI/ml has a viscosity no greater than 13.8 mPas, wherein the hydrophilic moieties are M or M$_1$, wherein each M$_1$ independently represents a —CHOHCON(R$_1$)$_2$ group wherein each R$_1$, which may be the same or different, is a hydrogen atom, an OH group or a C$_{1-6}$ alkoxy or optionally hydroxylated C$_{1-5}$ alkyl group, at least one R group being an M$_1$ moiety and each M independently is a non-ionic hydrophilic moiety.

2. A compound as claimed in claim 1 wherein both R$^1$ groups are hydrogen atoms.

3. A compound as claimed in claim 1 wherein the M groups are straight chain or branched C$_{1-10}$-alkyl groups with one or more CH$_2$ or CH moieties replaced by oxygen or nitrogen atoms and substituted by one or more groups selected from oxo, hydroxy, amino, carboxyl derivative, and oxo substituted sulphur and phosphorus atoms.

4. A compound as claimed in claim 1 wherein the M groups are groups selected from
—CONH—CH$_2$CH$_2$OH,
—CONH—CH$_2$CHOHCH$_2$OH,
—CONH—CH(CH$_2$OH)$_2$,
—CON(CH$_2$CH$_2$OH)$_2$,
—CONH$_2$,
—CONHCH$_3$,
—OCOCH$_3$,
—N(COCH$_3$)H,
—N(COCH$_3$)C$_{1-3}$-alkyl,
—N(COCH$_3$)-mono, bis or tris-hydroxy C$_{1-4}$-alkyl,
—N(COCH$_2$OH)-mono, bis or tris-hydroxy C$_{1-4}$-alkyl,
—NH(CO)-(mono, bis or trisphydroxy C$_{1-4}$-alkyl),
—N(mono-, bis or trisphydroxy C$_{1-4}$-alkyl)CO-(mono-, bis- or trishydroxy C$_{1-4}$ alkyl),
—N(COCH$_2$OH)$_2$,
—CON(CH$_2$CHOHCH$_2$OH)(CH$_2$CH$_2$OH),
—CONH—C(CH$_2$OH)$_3$ and
—CONH—CH(CH$_2$OH)(CHOHCH$_2$OH).

5. A compound as claimed in claim 1 wherein the M groups are straight chain or branched C$_{1-10}$-alkyl groups with one or more CH$_2$ or CH moieties replaced by oxygen or nitrogen atoms and substituted by one or more groups selected from the group consisting of oxo, hydroxy, amino, carboxyl derivative, and oxo substituted sulphur and phosphorus atoms.

6. A compound as claimed in claim 1 wherein the M groups are groups selected from the group consisting of
—CONH—CH$_2$CH$_2$OH,
—CONH—CH$_2$CHOHCH$_2$OH,
—CONH—CH(CH$_2$OH)$_2$,
—CON(CH$_2$CH$_2$OH)$_2$,
—CONH$_2$,
—CONHCH$_3$,
—OCOCH$_3$,
—N(COCH$_3$)H,
—N(COCH$_3$)C$_{1-3}$-alkyl,
—N(COCH$_3$)-mono, bis or tris-hydroxy C$_{1-4}$-alkyl,
—N(COCH$_2$OH)-mono, bis or tris-hydroxy C$_{1-4}$-alkyl,
—NH(CO)-(mono, bis or trishydroxy C$_{1-4}$-alkyl),
—N(mono-, bis or trishydroxy C$_{1-4}$ alkyl)CO-(mono-, bis- ortrishydroxy C$_{1-4}$ alkyl),
—N(COCH$_2$OH)$_2$,
—CON(CH$_2$CHOHCH$_2$OH)(CH$_2$CH$_2$OH),
—CONH—C(CH$_2$OH)$_3$ and
—CONH—CH(CH$_2$OH)(CHOHCH$_2$OH).

7. A compound of formula, I

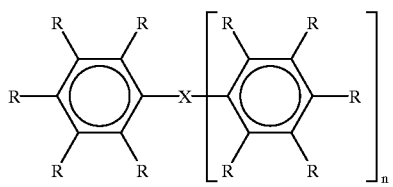

(I)

wherein n is 0 or 1, and where n is 1 each C$_6$R$_5$ moiety may be the same or different; X denotes a bond or a group providing a 1 to 7 atom chain linking two C$_6$R$_5$ moieties or, where n is 0, X denotes a group R; each group R is a hydrogen atom, an iodine atom or a hydrophilic moiety M or M$_1$, two or three non-adjacent R groups in each C$_6$R$_5$ moiety being iodine and at least one R group in each C$_6$R$_5$ moiety being an M or M$_1$ moiety; each M which may be the same or different, is a non-ionic hydrophilic moiety; and each M$_1$ independently represents a —CHOHCON(R$_1$)$_2$ group wherein each R$_1$, which may be the same or different, is a hydrogen atom, an OH group or a C$_{1-6}$ alkoxy or optionally hydroxylated C$_{1-5}$ alkyl group; at least one R group in the molecule being an M$_1$ moiety; and isomers thereof.

8. A compound as claimed in claim 7 wherein n=0.

9. A compound as claimed in claim 8 wherein 3 non-adjacent R groups are iodine and 2 R groups are M groups.

10. A compound as claimed in claim 9 wherein the 2 M groups are different.

11. A compound as claimed in claim 7 wherein at least one of the R$_1$ groups is a hydrogen atom.

12. A compound as claimed in claim 11 wherein both R$_1$ groups are hydrogen atoms.

13. A compound as claimed in claim 7 wherein the M groups are straight chain or branched C$_{1-10}$-alkyl groups with one or more CH$_2$ or CH moieties replaced by oxygen or nitrogen atoms and substituted by one or more groups selected from oxo, hydroxy, amino, carboxyl derivative, and oxo substituted sulphur and phosphorus atoms.

14. A compound as claimed in claim 13 wherein the M groups are hydroxy or polyhydroxyalkyl groups attached to the phenyl group by an amide linkage.

15. A compound as claimed in claim 7 of formula II'

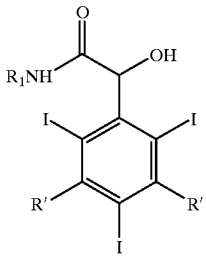

(II')

wherein each group R' is a hydrophilic moiety M or M$_1$ as defined in claim 7 and R$_1$ is as claimed in claim 7.

16. A compound as claimed in claim 15 wherein R$_1$ is hydrogen.

17. A compound as claimed in claim 15 wherein each group R' is a hydroxy or polyhydroxyalkyl group attached to the phenyl group by an amide linkage.

18. A compound as claimed in claim 17 wherein at least one R' groups is a C$_{2-4}$ polyhydroxyalkyl group attached to the phenyl group by an amide linkage.

19. A compound as claimed in claim 7 selected from the group consisting of (N-(2R,3S,4-trihydroxybutyryl)-N'-hydroxyacetyl-3,5-diamino-2,4,6-triiodomandeloamide), (N-(2R,3R,4-trihydroxybutyryl)-N'-hydroxyacetyl-3,5-diamino-2,4,6-triiodomandeloamide) and (5-(2,3-dihydroxypropionyl)-amino-3-N-(2,3-dihydroxypropyl)carbamido-2,4,6-triiodomandeloamide).

20. A diagnostic composition comprising a compound of formula I as claimed in claim 7 together with at least one physiologically tolerable carrier or excipient.

21. A method of generating an enhanced image of at least part of a human or non-human animal body which comprises administering to said body a compound of formula I as claimed in claim 7 and generating an image of at least part of said body to which said compound distributes.

22. A diagnostic composition comprising a compound as claimed in claim 1 together with at least one physiologically tolerable carrier or excipient.

23. In a method of X-ray imaging involving administration of a non-ionic contrast agent, the improvement comprising using as said agent a compound as claimed in claim 1.

24. A compound as claimed in claim 8 wherein three non-adjacent R groups are iodine the remaining R groups are M or M$_1$ moieties, said compound being water soluble at 20° C. to a concentration of at least 350 mgI/ml and which in aqueous solution at 20° C. at a concentration of 350 mg I/ml has a viscosity no greater than 13.8 mPas.

25. A compound as claimed in claim 8 wherein three non-adjacent R groups are iodine and the remaining R groups are M or M$_1$ moieties, said compound being water soluble at 20° C. to a concentration of at least 400 mgI/ml and which in aqueous solution at 20° C. at a concentration of 400 mg I/ml has a viscosity no greater than 30.0 mPas.

* * * * *